United States Patent [19]
Selten et al.

[11] Patent Number: 6,051,431
[45] Date of Patent: Apr. 18, 2000

[54] SELECTION MARKER GENE FREE RECOMBINANT STRAINS: A METHOD FOR OBTAINING THEM AND THE USE OF THESE STRAINS

[75] Inventors: Gerardus Cornelius Maria Selten, Berkel en Rodenrijs; Bart Willem Swinkels; Robertus Franciscus Maria Van Gorcom, both of Delft, all of Netherlands

[73] Assignee: DSM N.V., Netherlands

[21] Appl. No.: 08/987,067

[22] Filed: Dec. 8, 1997

Related U.S. Application Data

[60] Continuation of application No. 08/467,261, Jun. 6, 1995, abandoned, which is a division of application No. 08/279,980, Jul. 22, 1994, abandoned.

[51] Int. Cl.$^7$ .......................... C12N 15/87; C12N 15/74; C12N 15/75
[52] U.S. Cl. .......................... 435/465; 435/479; 435/483; 435/485; 435/488
[58] Field of Search ................................. 435/465, 479, 435/483, 485, 835, 839, 942, 488

[56] References Cited

U.S. PATENT DOCUMENTS

| | | | |
|---|---|---|---|
| 5,665,585 | 9/1997 | Torkkeli et al. | 435/203 |
| 5,766,918 | 6/1998 | Petre et al. | 435/228 |
| 5,795,760 | 8/1998 | Berka et al. | 435/189 |

FOREIGN PATENT DOCUMENTS

| | | | |
|---|---|---|---|
| 0 238 023 A2 | 9/1987 | European Pat. Off. . | |
| 0 463 706 A1 | 7/1990 | European Pat. Off. . | |
| 0 420 358 A1 | 4/1991 | European Pat. Off. . | |
| 506190 | 9/1992 | European Pat. Off. | 435/320.1 |

OTHER PUBLICATIONS

Jacobson, G.K., Mutations, Chapter 5b, pp. 279–304, in Rehm, H.–J., et al., ed., Biotechnology A Comprehensive Treatise in 8 Volumes, vol. 1, Microbial Fundamentals, Verlag Chemie, Deerfield Beach, Florida, 1981.

Kelly, J.M., et al., "Transformation of *Aspergillus niger* by the amdS gene of *Aspergillus nidulans*," *The EMBO Journal* (1985) 4(2):475–479.

Christensen, T., et al., "High Level Expression of Recombinant Genes in *Aspergillus oryzae*," *Bio/Technology* (Dec. 1988) 6:1419–1422.

Beri, R.K., et al., "Transformation of *Penicillium chrysogenum* using the *Aspergillus nidulans* amdS gene as a dominant selective marker," *Current Genetics* (1987) 11:639–641.

Penttilä, M., et al., "A versatile transformation system for the cellulolytic filamentous fungus *Trichoderma reesei*," *Gene* (1987) 61:155–164.

Tilburn, J., et al., "Transformation by integration in *Aspergillus nidulans*," *Gene* (1983) 26:205–221.

Sambrook, J, et al., Molecular cloning: a laboratory manual, 2$^{nd}$ ed. Cold Spring Harbor Laboratory Press 1989.

Gouka, R.J., et al., "Cloning of the nitrate–nitrite reductase gene cluster of *Penicillium chrysogenum* and use of the niaD gene as a homologous selection marker," *Journal of Biotechnology* (1991) 20:189–200.

Ito, H., et al., "Transformation of Intact Yeast Cells Treated with Alkali Cations," *Journal of Bacteriology* (1983) 153(1):163–168.

Yelton, M.M., et al., "Transformation of *Aspergillus nidulans* by using trpC plasmid," *Proc Natl Acad Sci USA* (Mar. 1984) 81:1470–1474.

Kolar, M., et al., "Transformation of *Penicillium chrysogenum* using dominant selection markers and expression of an *Escherichia coli* lacZ fusion gene," *Gene* (1988) 62:127–134.

Fujimura, H., et al., "Simplified Isolation of Chromosomal and Plasmid DNA from Yeasts," *BioTechniques* (1993) 14(4):538–539.

Corrick, C.M., et al., "The nucleotide sequence of the amdS gene of *Aspergillus nidulans* and the molecular characterization of 5' mutations," *Gene* (1987) 53:63–71.

Van Hartingsveldt, W., et al., "Cloning, characterization and overexpression of the phytase–encoding gene (phyA) of *Aspergillus niger*," *Gene* (1993) 127:87–94.

Auffray, C., et al., "Purification of Mouse Immunoglobulin Heavy–Chain Messenger RNAs from Total Myeloma Tumor RNA," *Eur J Biochem* (1980) 107:303–314.

Cove, D.J., "The Induction and Repression of Nitrate Reductase in the Fungus *Aspergillus nidulans*," *Biochimica et Biophysica Acta* (1966) 113:51–56.

Yanisch–Perron, C., et al., "Improved M13 phage cloning vectors and host strains: nucleotide sequences of the M13mp18 and pUC19 vectors," *Gene* (1985) 33:103–119.

Verdoes, J.C., et al., "Glucoamylase overexpression in *Aspergillus niger*: molecular genetic analysis of strains containing multiple copies of the glaA gene," *Transgenic Research* (1993) 2:84–92.

Saiki, R.K., et al., "Primer–Directed Enzymatic Amplification of DNA with a Thermostable DNA Polymerase," *Science* (Jan. 1988) 239:487–491.

Punt, P.J., et al., "Transformation of Aspergillus based on the hygromycin B resistance marker from *Escherichia coli*," *Gene* (1987) 56:117–124.

(List continued on next page.)

*Primary Examiner*—John S. Brusca
*Assistant Examiner*—William Sandals
*Attorney, Agent, or Firm*—Morrison & Foerster LLP

[57] ABSTRACT

The present invention discloses a selection marker free system which can be used to introduce genetic modifications in bacteria, yeasts and fungi. The system can be employed to introduce or delete desired genes or DNA fragments in the genome of the indicated host species without leaving any undesired DNA i.e. the selection marker used for selection of transformants or other DNA used for cloning. In this way strains have been developed containing only desired genes introduced at desired chromosomal sites. Similarly, desired DNA fragments have been deleted or replaced at desired sites.

25 Claims, 59 Drawing Sheets

OTHER PUBLICATIONS

Reiss, B., et al., "Protein fusions with the kanamycin resistance gene from transposon Tn5," *The EMBO Journal* (1984) 3(13): 3317–3322.

Bennetzen, J.L., et al., "The Primary Structure of the *Saccharomyces cerevisiae* Gene for Alcohol Dehydrogenase I," *The Journal of Biological Chemistry* (Mar. 25, 1982) 257(6):3018–3025.

Nagata, S., et al., Polypeptide chain elongation factor 1α (EF–1α) from yeast: nucleotide sequence of one of the two genes for EF–1α from *Saccharomyces cerevisiae*, *The EMBO Journal* (1984) 3(8):1825–1830.

Das, S., et al., "A High–Frequency Transformation System for the Yeast *Kluyveromyces lactis*," *Current Genetics* (1982) 6:123–128.

Don, R.H., et al., "Touchdown' PCR to circumvent spurious priming during gene amplification," *Nucleic Acids Research* (Jul. 25, 1991) 19(14):4008.

van den Berg, J.A., et al., "Kluyveromyces as a Host for Heterologous Gene Expression: Expression and Secretion of Prochymosin," *Bio/Technology* (Feb. 1990) 8:135–139.

Sreekrishna, K., et al., "Transformation of *Kluyveromyces lactis* with the kanamycin (G418) resistance gene of Tn903," *Gene* (1984) 28:73–81.

Breunig, K.D., "Glucose repression of LAC gene expression in yeast is mediated by the transcriptional activator LAC9," *Mol Gen Genet* (1989) 216:422–427.

Hynes, M.J., et al., "The Genetic Analysis of Regulation of Amidase Synthesis in *Aspergillus nidulans*," *Molec Gen Genetics* (1970) 108:107–116.

Rothstein, R.J., "[12] One–Step Gene Disruption in Yeast," in, Cloning of Genes Into Yeast Cells, Methods in Enzymology, vol. 101, pp. 202–211, Academic Press, Inc., 1983, New York.

Freese, E., et al., "Growth and Sporulation of *Bacillus subtilis* Mutants blocked in the Pyruvate Dehydrogenase Complex," *Journal of Bacteriology* (Sep. 1969) 99(3):745–756.

Grundy, F.J., et al., "Identification of genes involved in utilization of acetate and acetoin in *Bacillus subtilis*," *Molecular Microbiology* (1993) 10(2):259–271.

Part of pAB6-1
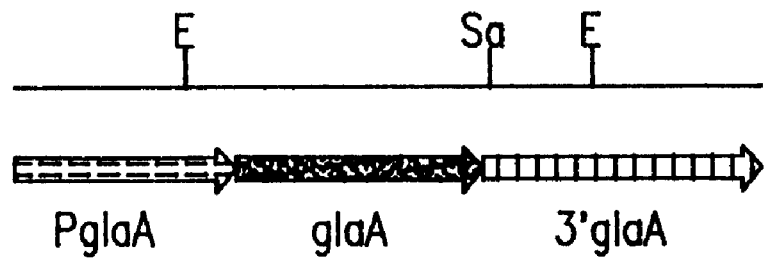
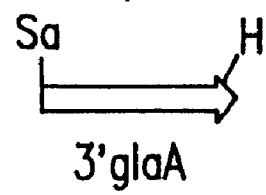
FIG. 7a

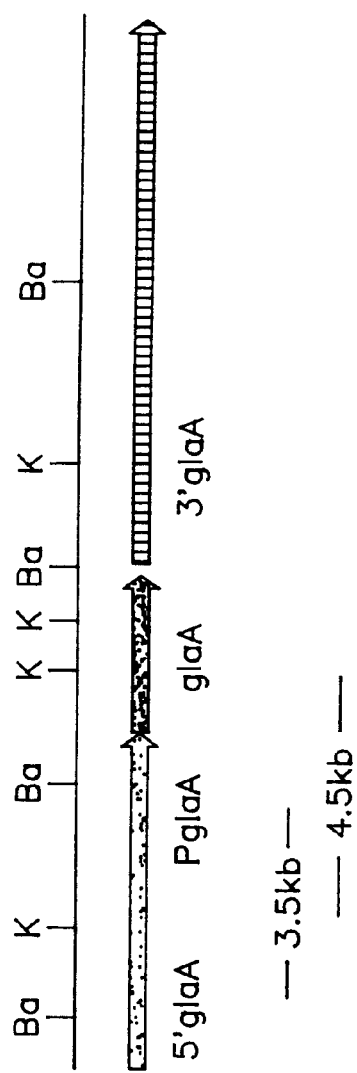
FIG. IIa
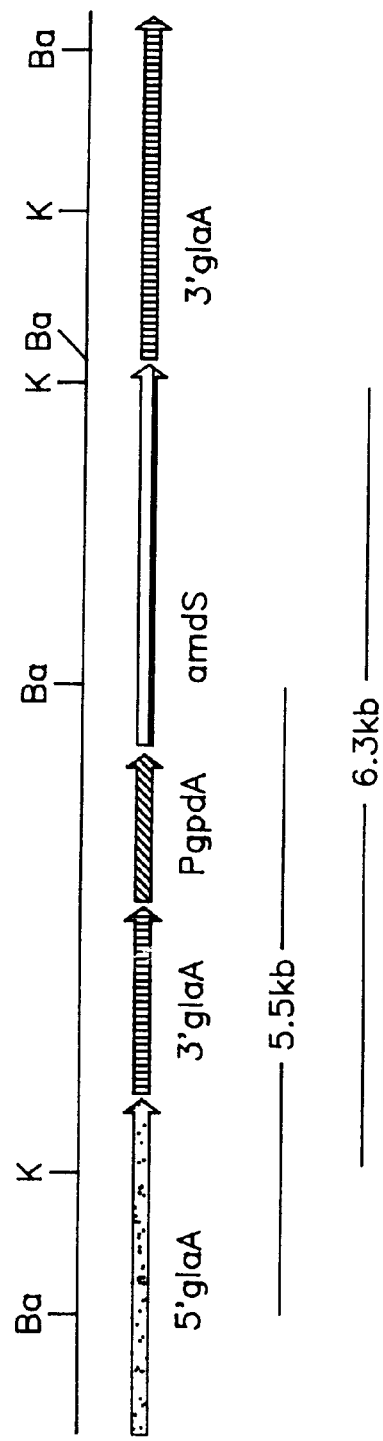
FIG. IIb

5' AGCTTGACGTCTACGTATTAATGCGGCCGCT            3'
3'         ACTGCAGATGCATAATTACGCCGGCGAAGCT   5'

5' AATTGGGGCCCAGCGTCC 3'
3' CCCCGGGTCGCAGGTTAA 5'

SELECTION MARKER GENE FREE RECOMBINANT STRAINS: A METHOD FOR OBTAINING THEM AND THE USE OF THESE STRAINS

This application is a continuation of U.S. Ser. No. 08/467,261 filed Jun. 6, 1995, now abandoned, which is a divisional of U.S. Ser. No. 08/279,980 filed Jul. 22, 1994, now abandoned.

TECHNICAL FIELD

The present invention discloses selection marker gene free recombinant strains, a method for obtaining these strains and the use of these strains. Furthermore, the method of the present invention is used for performing strain improvement.

BACKGROUND OF THE INVENTION

There is an increasing social concern about the use of recombinant DNA technology. One of the promising application areas of recombinant DNA technology is strain improvement. Starting from the early days of fermentative production processes there has been a demand for the improvement of the productivity of the strains used for production.

Classical strain improvement programs for industrially employed microorganisms are primarily based on random mutagenesis followed by selection. Mutagenesis methods have been described extensively; they include the use of UV light, NTG or EMS as mutagens. These methods have been described extensively for example in "Biotechnology: a comprehensive treatise in 8 vol." Volume I, Microbial fundamentals, Chapter 5b, Verlag Chemie GmbH, Weinheim, Germany.

Selection methods are generally developed around a suitable assay and are of major importance in the discrimination between wild type and mutant strains.

It has turned out that these classical methods are limited in their potential for improvement. Generally speaking consecutive rounds of strain improvement yield diminishing increases in yield of desired products. This is at least partially due to the random character of the mutagenesis methods employed. Apart from desired mutations these methods also give rise to mutations which are undesirable and which may negatively influence other characteristics of the strains.

In view of these drawbacks it can be understood that the use of recombinant DNA methods was hailed as a considerable improvement. In general, recombinant DNA methods used in strain improvement programs aim at the increased expression of desired gene products.

The gene products may be proteins that are of interest themselves, on the other hand it is also possible that the encoded gene products serve as regulatory proteins in the synthesis of other products.

Strains can be improved by introducing multiple copies of desired protein encoding genes into specific host organisms. However, it is also possible to increase expression levels by introducing regulatory genes.

Genes are introduced using vectors that serve as vehicles for introduction of the genes. Such vectors may be plasmids, cosmids or phages. The vector may be capable of expression of the genes in which case the vector generally is self-replicating. The vector may however also only be capable of integration. Another characteristic of the vector is that, when the expression product cannot be selected easily based on altered phenotypic properties, the vector is equipped with a marker that can easily be selected for.

Vectors have not been isolated from all known microorganisms either since no vector could be found in the organism or since available vectors from other organisms, could be used with little or no modification. The same applies to selection marker genes.

Widespread use and the subsequent spreading of specific marker genes has recently become debatable. This is especially due to the finding that the use of antibiotics and antibiotic selection markers gives rise to an undesired spread of strains that have become antibiotic resistant. This necessitates the continued development of novel ever more potent antibiotics.

It is therefore not surprising that there is a general tendency in large scale production to use recombinant microorganisms containing no antibiotic resistance genes or more generally as little as possible of foreign DNA.

Ideally the transformed microorganism would contain only the desired gene(s), fragments thereof or modifications in the gene and as little as possible or no further remnants of the DNA used for cloning.

SUMMARY OF THE INVENTION

The present invention discloses a selection marker gene that can easily be deleted again from the recombinant host organism. The deletion of the said marker gene is based on dominant selection.

The marker is used in species so diverse as bacteria, filamentous fungi and yeasts.

The advantageous activity of the selection markers used herein is based on the following two step principle:

a) the gene is integrated into the genome of the host organism and recombinant cells are selected, b) the transformed cell is grown on a substrate, which is converted by the marker gene encoded activity to a product that is lethal to the cell.

Selected cells will be recombinant and will have deleted the selection marker gene.

In general terms the present invention discloses cells, that may be animal or plant cells, and microorganisms that have a modification in the genome characterized in that the alteration is introduced using the amdS gene or the cDNA derived therefrom.

An example of a selection marker gene that can be used in this way is the acetamidase gene. Preferably, this gene is obtainable from filamentous fungi, more preferably from Aspergilli, most preferably from *Aspergillus nidulans*.

The invention further shows the introduction, deletion or modification of desired heterologous or homologous genes or DNA elements in the host organisms of choice using the acetamidase (amdS) gene as a marker. Subsequently the amdS gene is deleted. Preferably, the amdS and the desired genes are introduced site-specifically.

The invention discloses a vector containing:

a) a desired DNA fragment destined for introduction into the host genome, b) optionally a DNA sequence that enables the vector to integrate (site-specifically) into the genome of the host strain, c) a gene encoding an acetamidase (e.g. the amdS gene from *A. nidulans*) between DNA repeats.

The invention further discloses host organisms transformed with the said vector.

The invention further discloses selection marker gene free recombinant microorganisms.

Specifically, the invention discloses organisms containing site-specifically introduced genes without any further foreign DNA being present. The method is therefore also suited for repeated modifications of the host genome, e.g. the sequential introduction of multiple gene copies at predetermined loci.

The invention provides a method for obtaining selection marker gene free recombinant strains comprising the following steps:

a) integration into the genome of the strain of a desired DNA fragment and a selection marker, b) selection of the recombinants, c) deletion of the selection marker preferably using internal recombination between selection marker flanking repeats, d) counter-selection based on the absence of the selection marker.

Although this is the preferred method for obtaining selection marker gene free recombinant strain, the invention also provides modifications of this method, for example:

The desired DNA fragment and the selection marker may be present on two different DNA molecules which are co-transformed. The selection marker does not necessarily integrate into the genome of the strain but may be present on an episomal DNA molecule which can be cured.

The present invention further illustrates that this marker gene can be deleted from the genome of the transformed organisms without leaving a trace i.e. DNA used for cloning.

The present invention discloses the use of the amdS gene from Aspergillus as a marker in bacteria and yeast.

The invention discloses also the use of the amdS gene for deleting a desired gene from the chromosome of a 'host' organism. Such modification techniques may be applied to filamentous fungi, yeasts and bacteria. In specific embodiments the following strains are employed Aspergilli, Trichoderma, Penicillium, Bacilli, *E. coli*, Kluyveromyces and Saccharomyces.

The method of the present invention provides recombinant strains with genomic modifications obtained by repeating the procedure with the same or other vectors.

BRIEF DESCRIPTION OF THE DRAWINGS

Abbreviations used in the figures:

Restriction enzymes and restriction sites:

A=ApaI; Ba=BamHI; B=BglII; Bs=BssHII; E=EcoRI; H=HindIII; K=KpnI; N=NdeI; N=NotI; Ps=PstI; P=PvuII; Sa=SalI; Sc=ScaI; S=SmaI; Sn=SnaBI; Spe=SpeI; Sp=SphI; Ss=SstII; Xb=XbaI; X=XhoI.

Other:

T.=LAC4 terminator sequence

Figure 1:
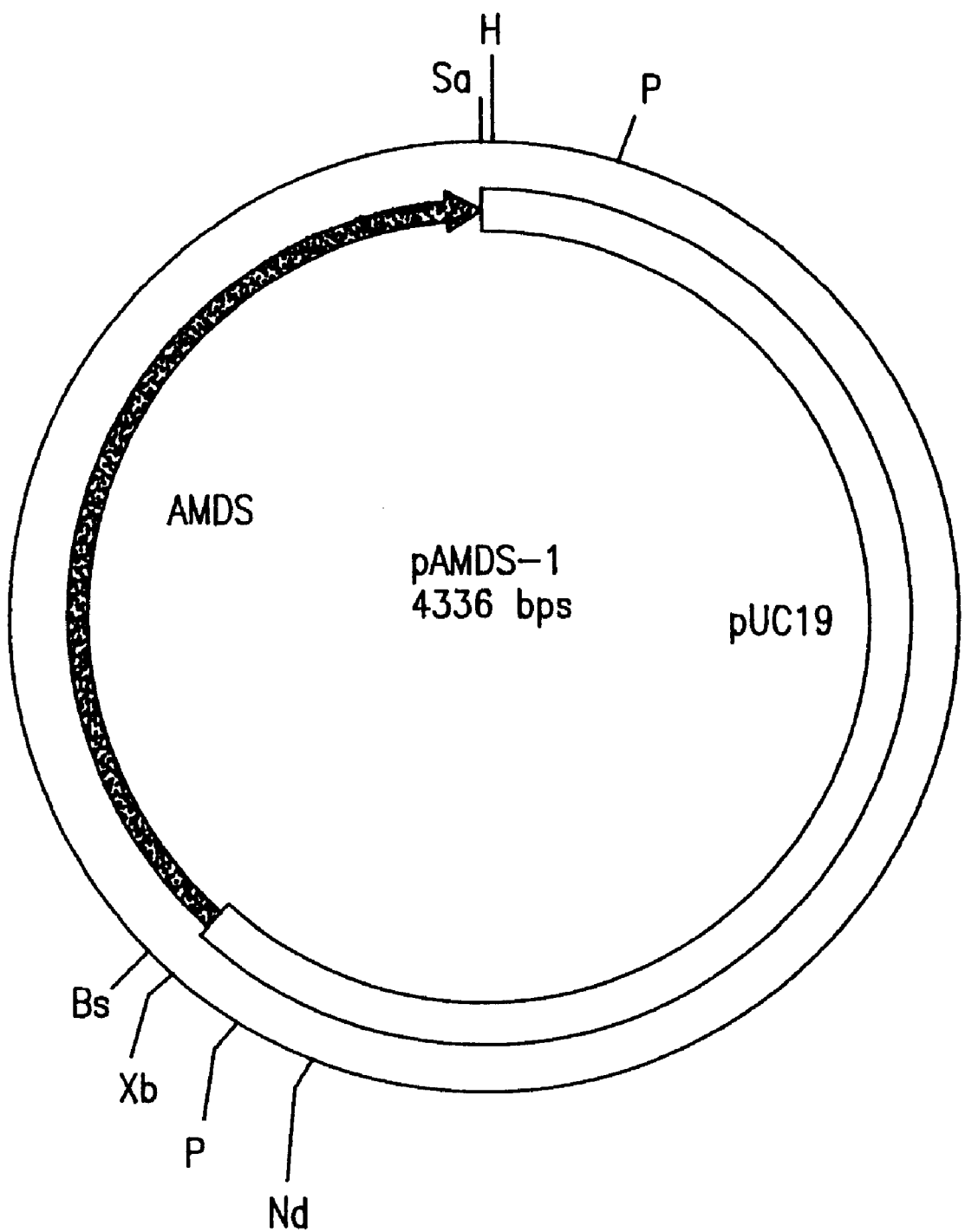

FIG. 1: shows the restriction map of plasmid pamdS-1. This plasmid contains the cDNA of the amdS gene from *A. nidulans*.

Figure 2:
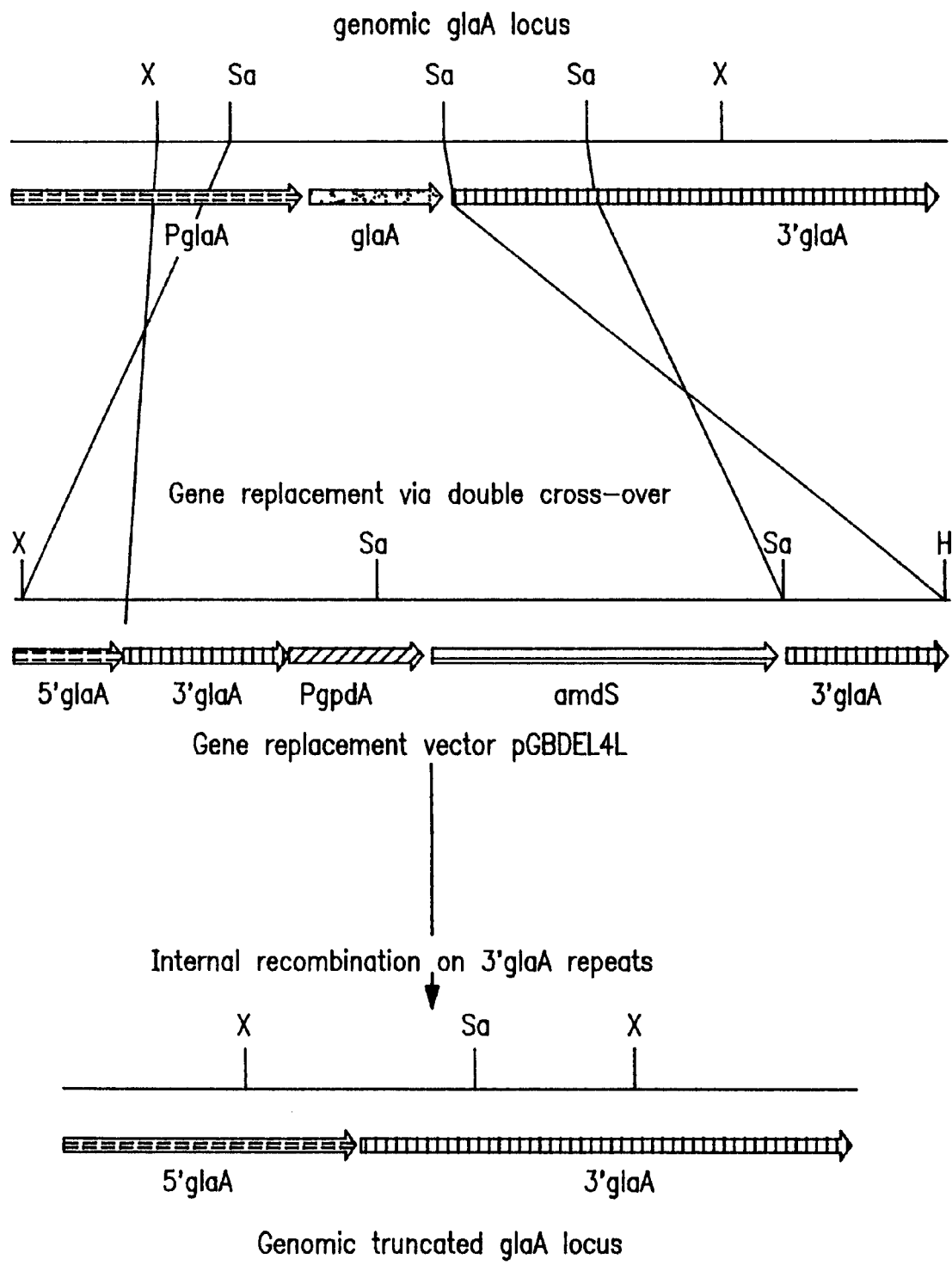

FIG. 2: shows schematically the marker gene free deletion of the glaA locus from *A. niger* using the gene replacement vector pGBDEL4L. The essential part of the gene replacement vector pGBDEL4L contains the amdS gene under control of the gpdA promoter cloned between repeats (3'-non-coding region of the glaA gene).

FIGS. 3–9: show schematically the construction pathway of pGBDEL4L as further outlined in Example 1.

FIG. 10

A. KpnI digests of pGBDEL4L transformants #41 (lane 1), #24 (lane 2), #23 (lane 3) and #19 (lane 4) and the host strain *A. niger* CBS 513.88 (lane 5) and BamHI digests of pGBDEL4L transformants #41 (lane 6), #24 (lane 7), #23 (lane 8), #19 (lane 9) and the host strain *A. niger* CBS 513.88 (lane 10), probed with $^{32}$P-labelled glaA promoter fragment and xylanase probe.

B. KpnI digests of GBA-102 (lane 1) and the GBA-102 strains after fluoracetamide selection: GBA-107 (lane 2) and GBA-108 (lane 3) and BamHI digests of GBA-102 (lane 4) and the GBA-102 strains after fluoracetamide selection: GBA-107 (lane 5) and GBA-108 (lane 6), probed with $^{32}$P-labelled glaA promoter fragment and, xylanase probe.

FIG. 11:

A. Schematic presentation of BamHI and KpnI fragment lengths of the wild-type glaA locus in *Aspergillus niger* CBS 513.88.

B. Schematic presentation of BamHI and KpnI fragment lengths of the truncated glaA locus in transformant #19 (=GBA-102).

C. Schematic presentation of BamHI and KpnI fragment lengths of the truncated glaA locus in GBA-102 transformants after removal of the amdS gene (=GBA-107 and GBA-108).

FIG. 12:

A: shows schematically the integration of the glaA gene into the 3' non-coding region of truncated glaA locus of *A. niger* GBA-107.

B: shows the result of the internal recombination between the 3' glaA repeats, flanking the amdS gene.

FIGS. 13–24: show schematically the construction pathway of the integration vector pGBGLA30 as further outlined in Example 2.

Figure 25:
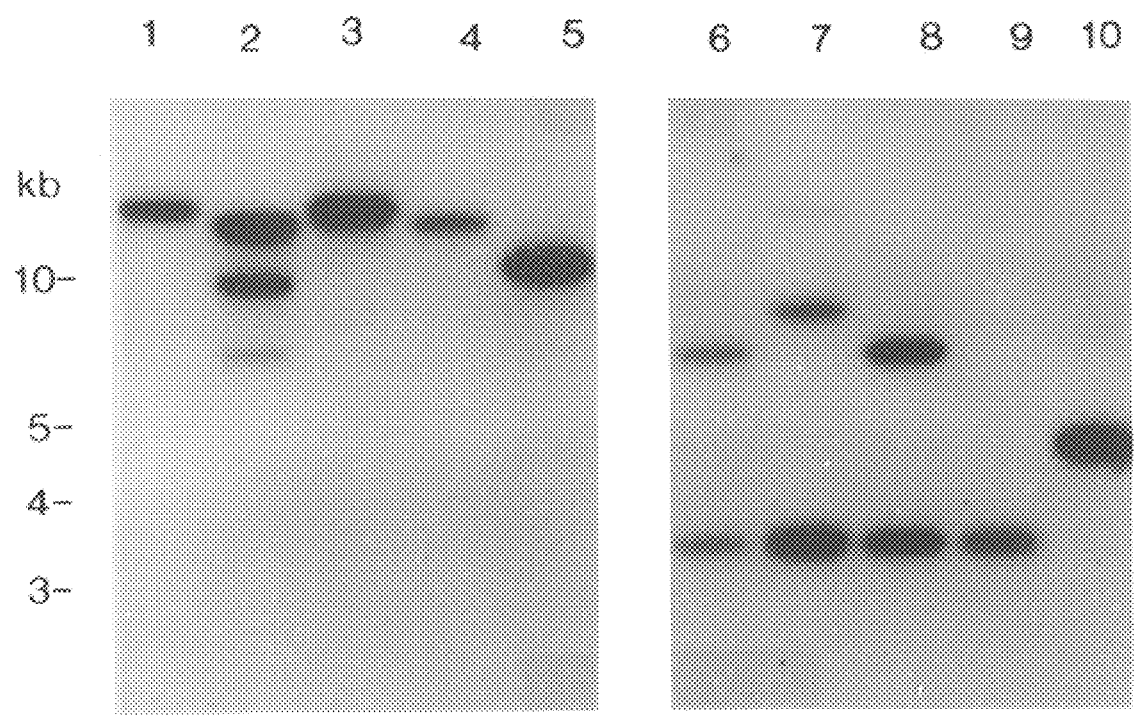

FIG. 25: BglII digests of pGBGLA30 transformants #107-9 (lane 1), #107-7 (lane 2) and #107-5 (lane 3), the host strain *A. niger* GBA-107 (lane 4) and the parental strain *A. niger* CBS 513.88 (lane 5) and KpnI digests of pGBGLA30 transformants #107-9 (lane 6), #107-7 (lane 7) and #107-5 (lane 8), the host strain *A. niger* GBA-107 (lane 9) and the parental strain *A. niger* CBS 513.88 (lane 10), probed with $^{32}$P-labelled glaA promoter fragment.

FIG. 26:

A: Schematic presentation of the KpnI and BglII fragment lengths of the wild-type glaA locus in *Aspergillus niger* CBS 513.88.

B: Schematic presentation of the KpnI and BglII fragment lengths of the truncated glaA locus in *Aspergillus niger* GBA-107.

C: Schematic presentation of the KpnI and BglII fragment lengths of the truncated glaA locus with a single copy pGBGLA30 integrated into the glaA 3'-non-coding region as in transformants #107-5 (=GBA-119) and #107-9 (=GBA-122).

D: Schematic presentation of the KpnI and BglII fragment lengths of the truncated glaA locus in GBA-119 and GBA-122 transformants after removal of the amdS gene (=GBA-120, GBA-121, GBA-123 and GBA-124).

FIG. 27:

A: BglII digests of *A. niger* CBS 513.88 (lane 10), GBA-107 (lane 9), GBA-119 (lane 8) and the GBA-119 strains after fluoracetamide selection: #AG5-7 (=GBA-120) (lane 5), #AG5-5 (=GBA-121) (lane 6) and #AG5-6 (lane 7); GBA-122 (lane 4) and the GBA-122 strains after fluoracetamide selection: #AG9-1 (=GBA-123) (lane 3), #AG9-2 (lane 2) and #AG9-4 (=GBA-124) (lane 1), probed with $^{32}$P-labelled 3" glaA non-coding fragment.

B: KpnI digests of *A. niger* CBS 513.88 (lane 10), GBA-107 (lane 9), GBA-119 (lane 8) and the GBA-119 strains after fluoracetamide selection: #AG5-7 (=GBA-120) (lane 5), #AG5-5 (=GBA-121) (lane 6) and #AG5-6 (lane 7);

GBA-122 (lane 4) and the GBA-122 strains after fluoracetamide selection: #AG9-1 (=GBA-123) (lane 3), #AG9-2 (lane 2) and #AG9-4 (=GBA-124) (lane 1), probed with $^{32}$P-labelled 3" glaA non-coding fragment.

Figure 28:
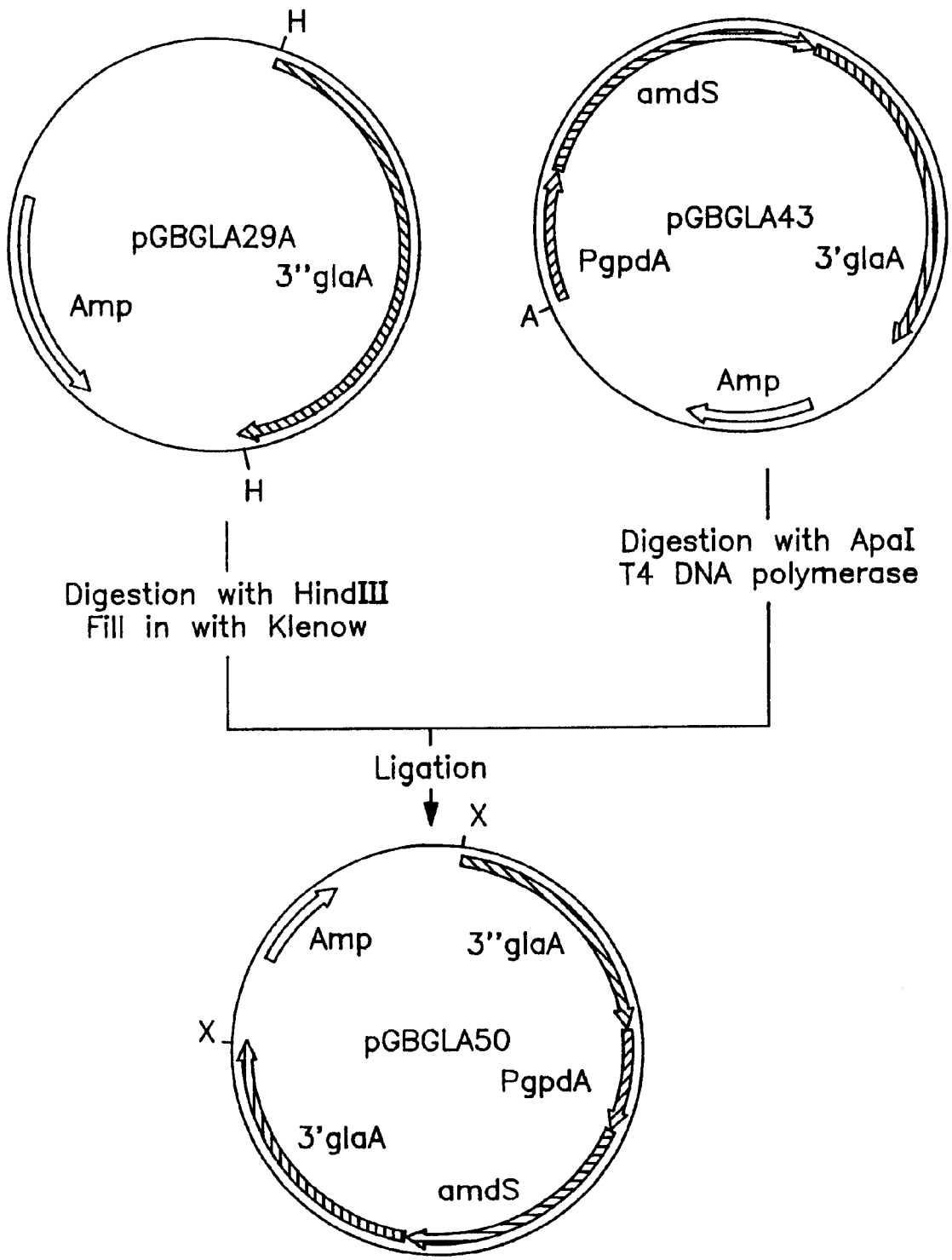

FIG. 28: shows schematically the construction pathway of pGBGLA50.

FIGS. 29–33: show schematically the construction pathway of pGBGLA53.

Figure 34:
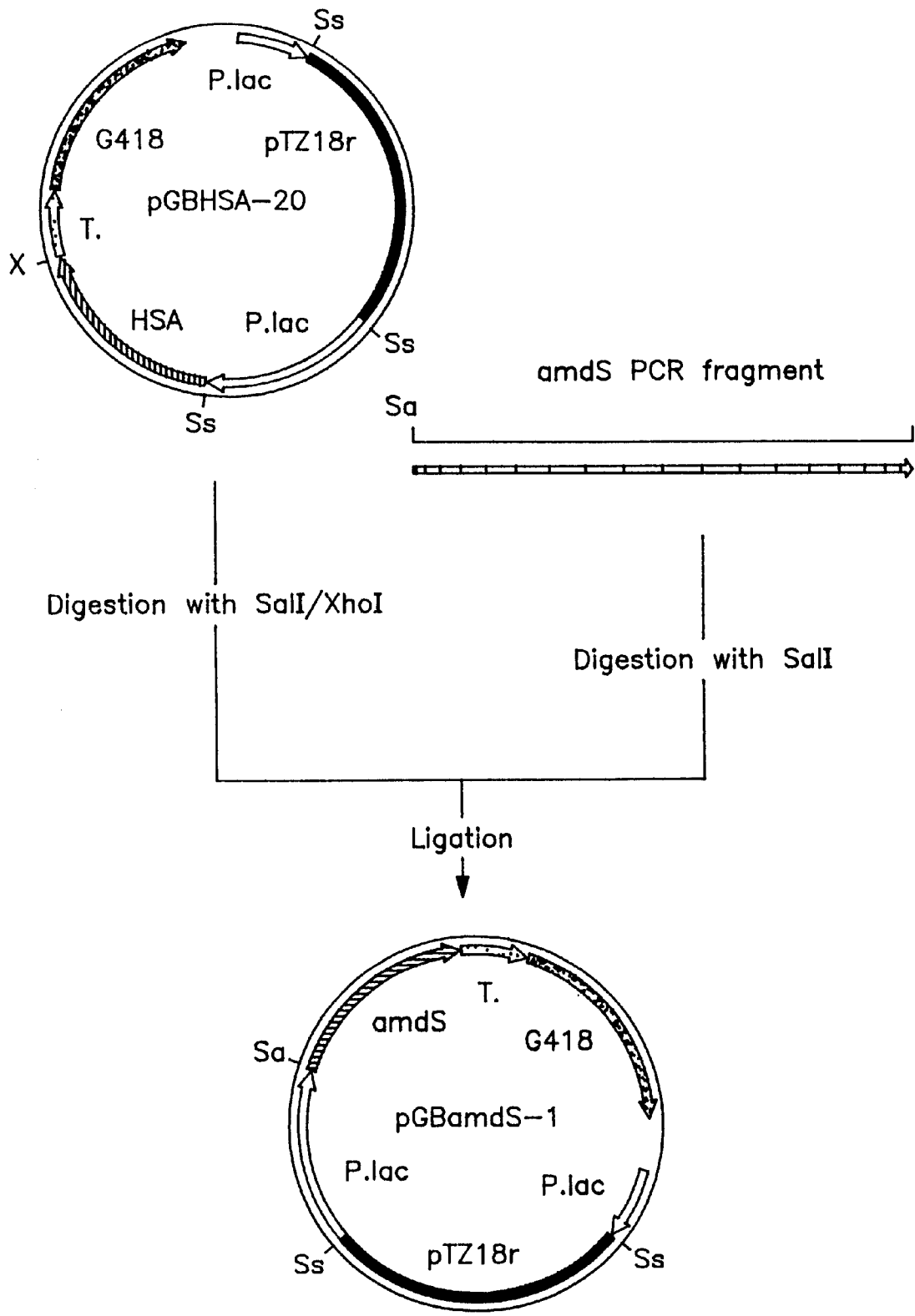

FIG. 34: shows schematically the construction of pGBamdS1.

Figure 35:
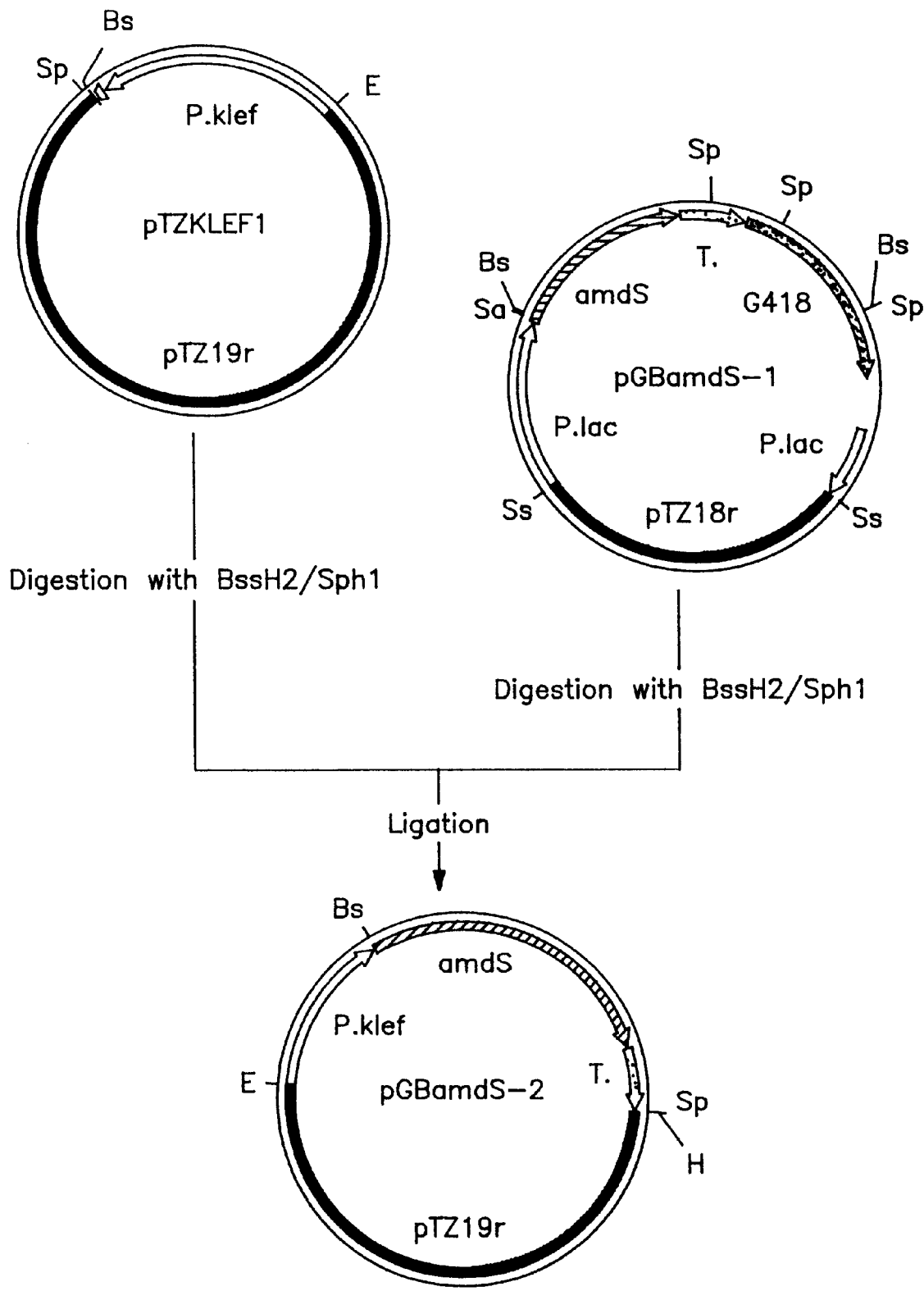

FIG. 35: shows schematically the construction of pGBamdS2.

Figure 36:
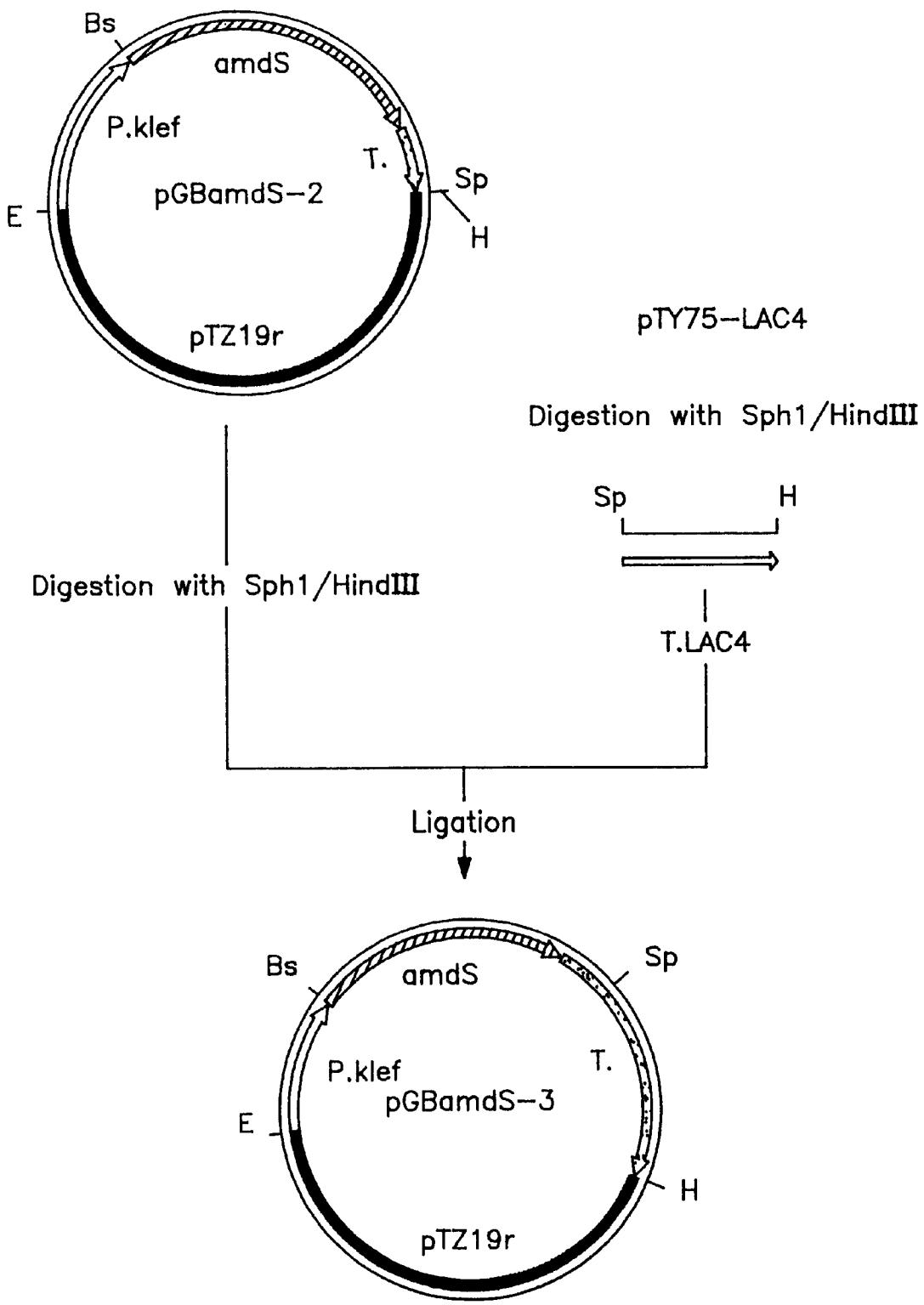

FIG. 36: shows schematically the construction of pGBamdS3.

Figure 37:
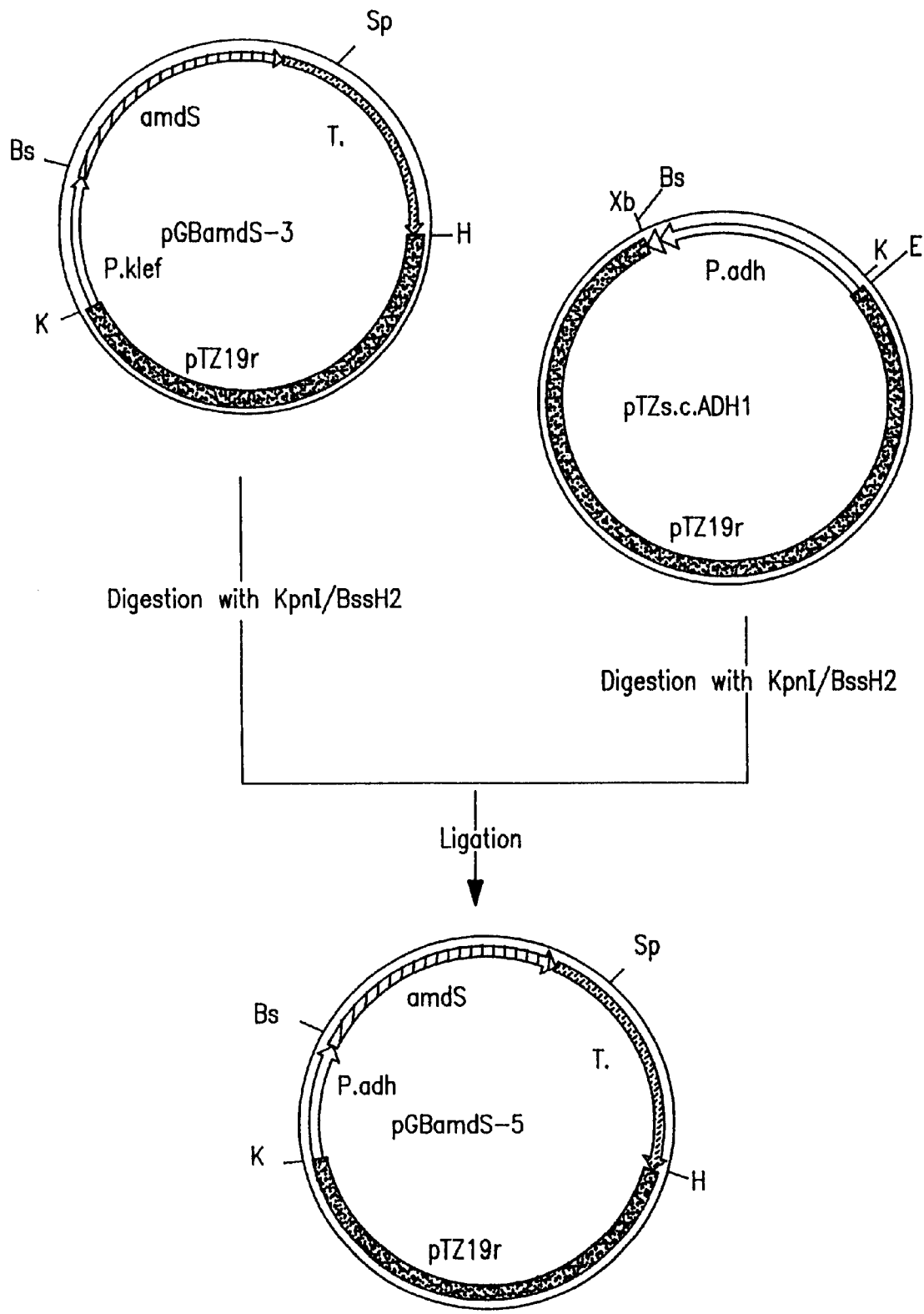

FIG. 37: shows schematically the construction of pGBamdS5.

Figure 38:
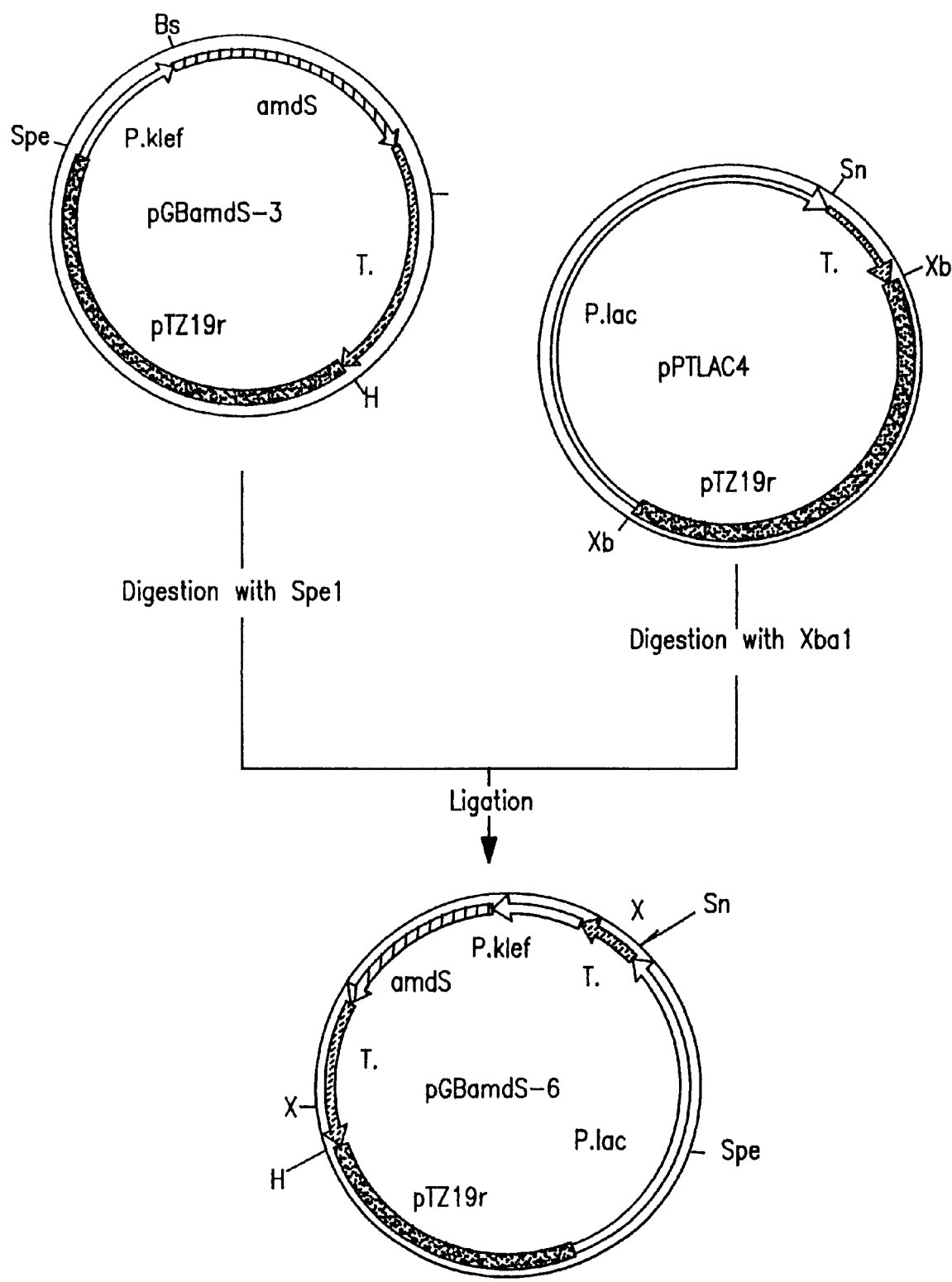

FIG. 38: shows schematically the construction of pGBamdS6.

Figure 39:
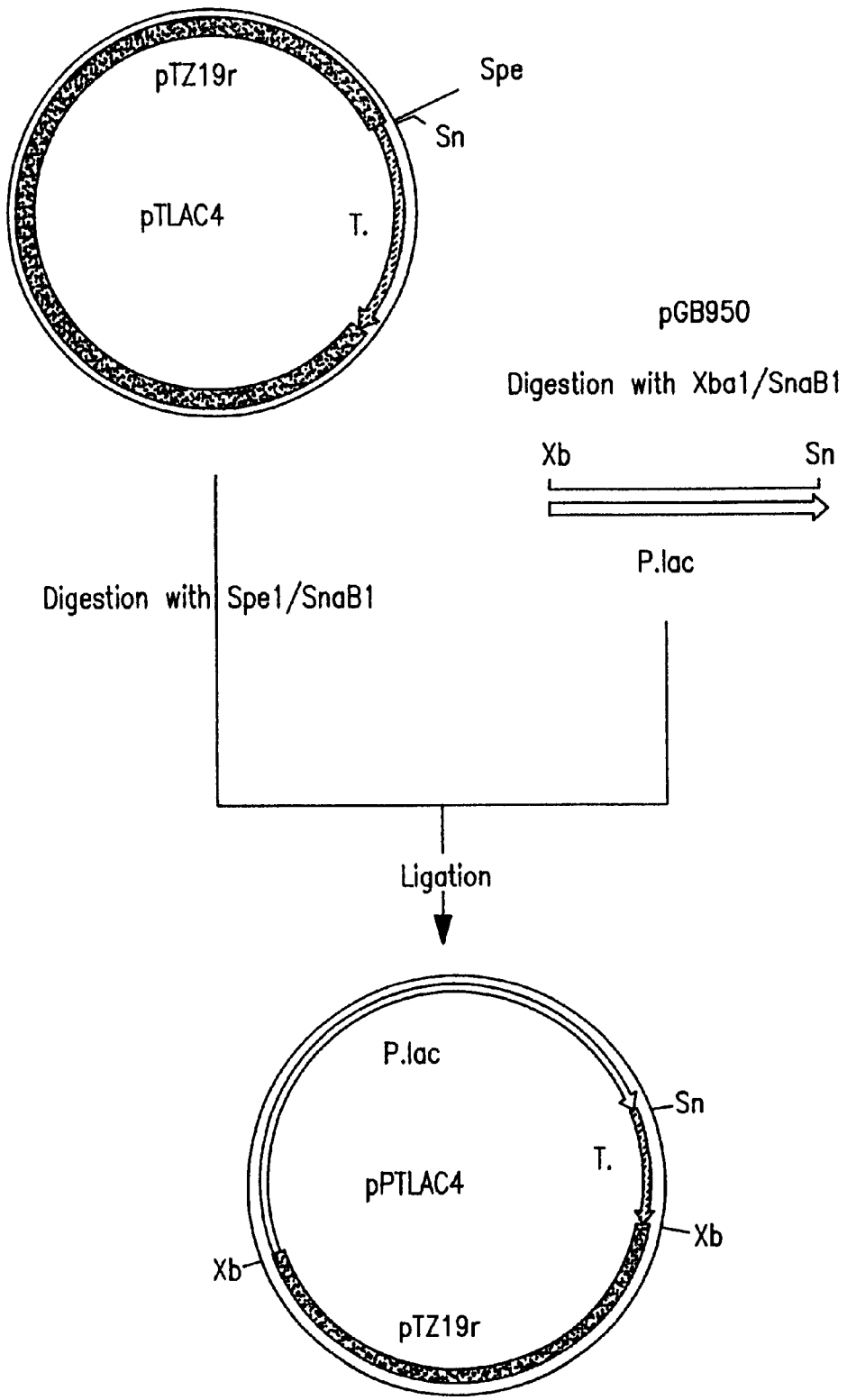

FIG. 39: shows schematically the construction of pPT-LAC4 which was used in the construction of pGBamdS6.

Figure 40:
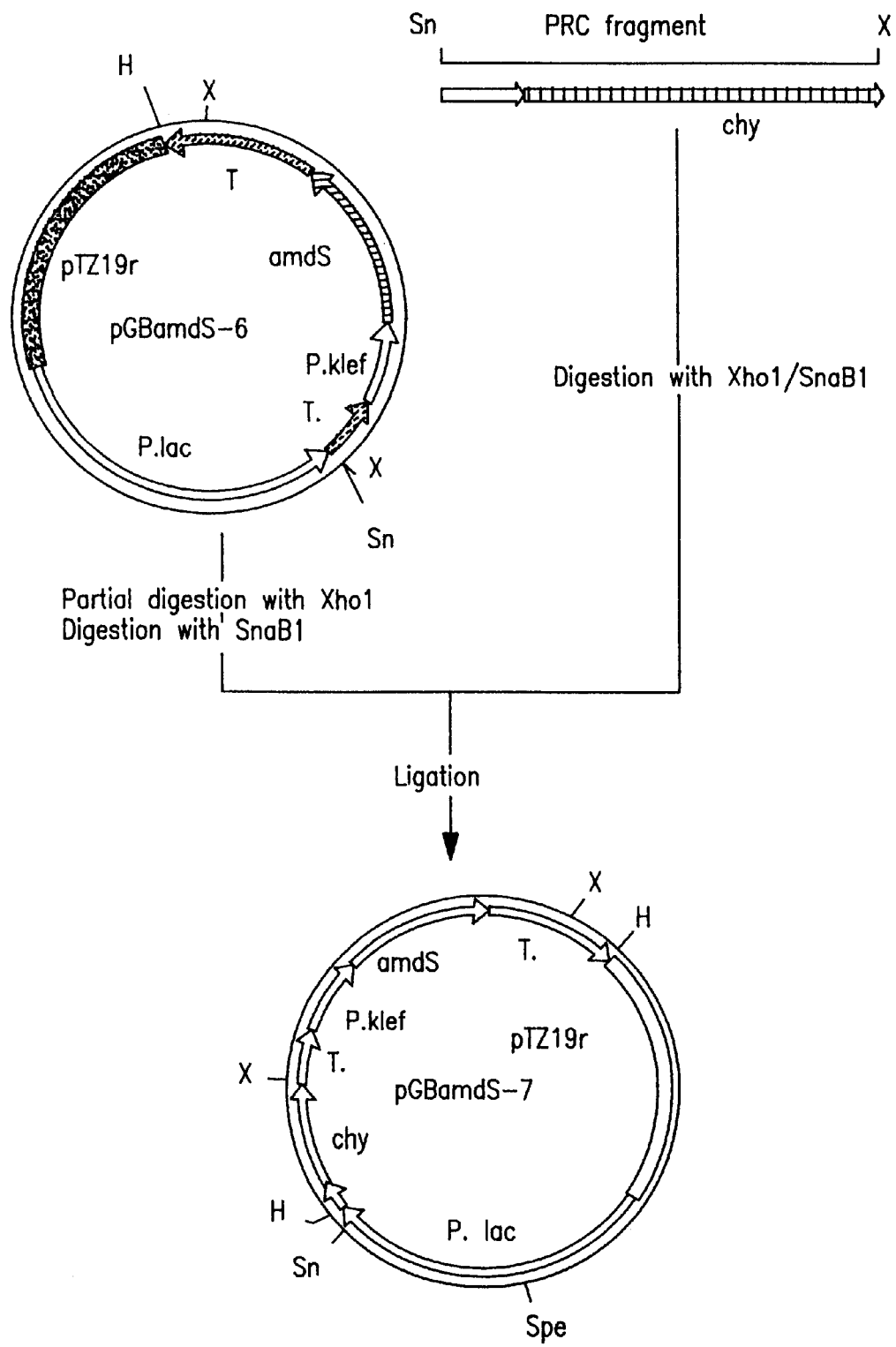
Figure 4I:
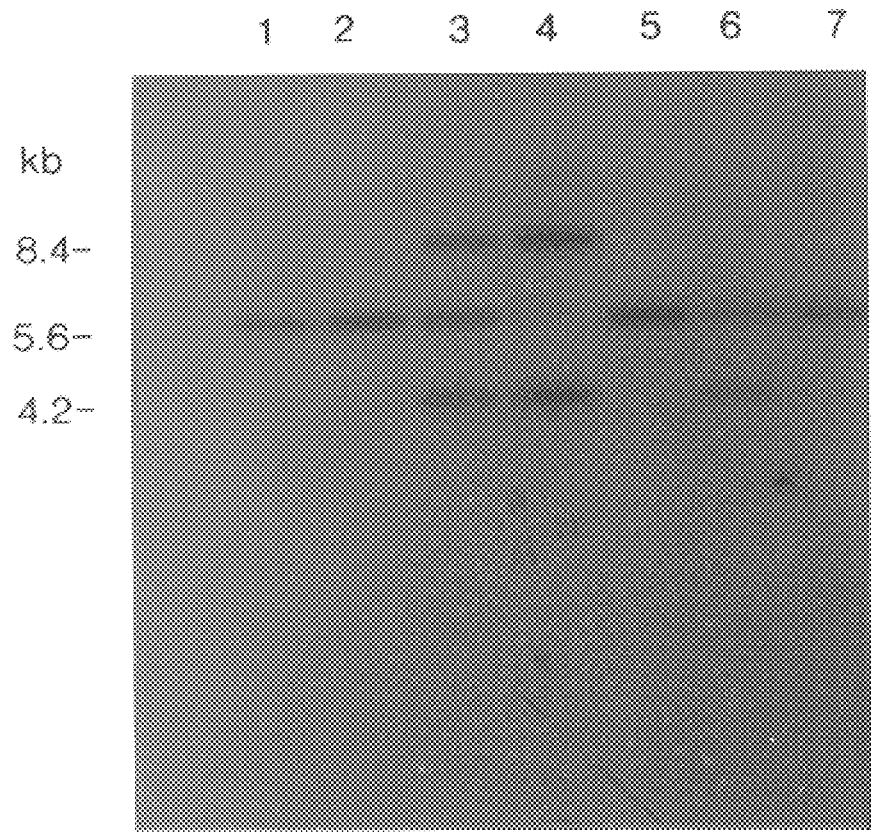

FIG. 40: shows schematically the construction of pGBamdS7.

FIG. 41: HindIII digests of K. lactis CBS 683 (lane 1), K. lactis CBS 2360 (lane 2), the K. lactis CBS 683/pGBamdS1 transformants KAM-1 (lane 3), the K. lactis; CBS 2360/ pGBamdS1 transformant KAM-2 (lane 4) and the KAM-1 strains after fluoracetamide selection (lane 5,6) probed with a 32p labelled LAC4 promoter fragment.

FIG. 42:

A: BamHI digests of K. lactis CBS 683/pGBamdS3 transformants (lanes 1–3) probed with a $^{32}$P-labelled LAC4 terminator fragment.

B: BamHI digests of K. lactis CBS 683/pGBamdS5 transformants (lanes 1–5) and the host strain K. lactis CBS 683 (lane 6) probed with a $^{32}$P-labelled LAC4 terminator fragment.

Figure 43:
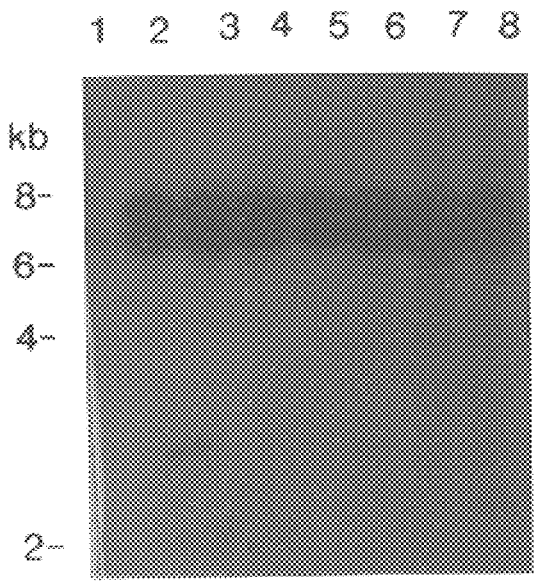

FIG. 43: BamHI digests of S. cerevisiae D273-10B (lane 1) and S. cerevisiae D273-10B/pGBamdS5 transformants (lanes 2-8) probed with a $^{32}$P-labelled amdS fragment.

Figure 44:
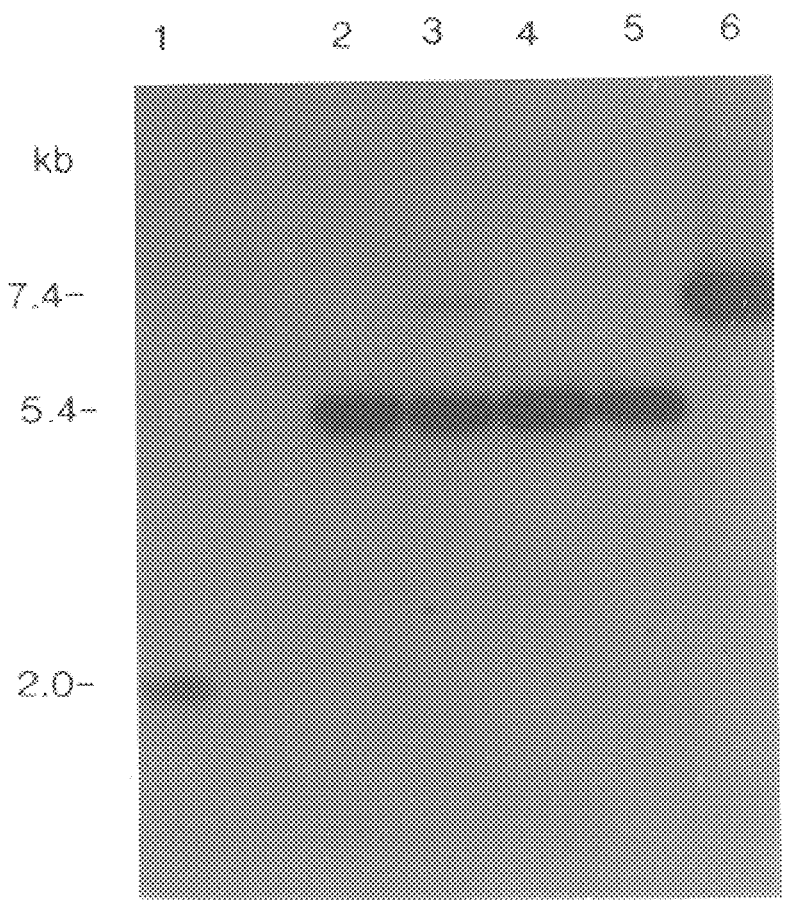

FIG. 44: HindIII digests of K. lactis CBS 2360 (lane 1), the K. lactis CBS 2360/pGBamdS6 transformant (lane 6) and strains from the K. lactis CBS 2360/pGBamdS6 transformant after fluoracetamide selection (lanes 2–5) probed with a $^{32}$P-labelled LAC4 terminator fragment.

Figure 45:
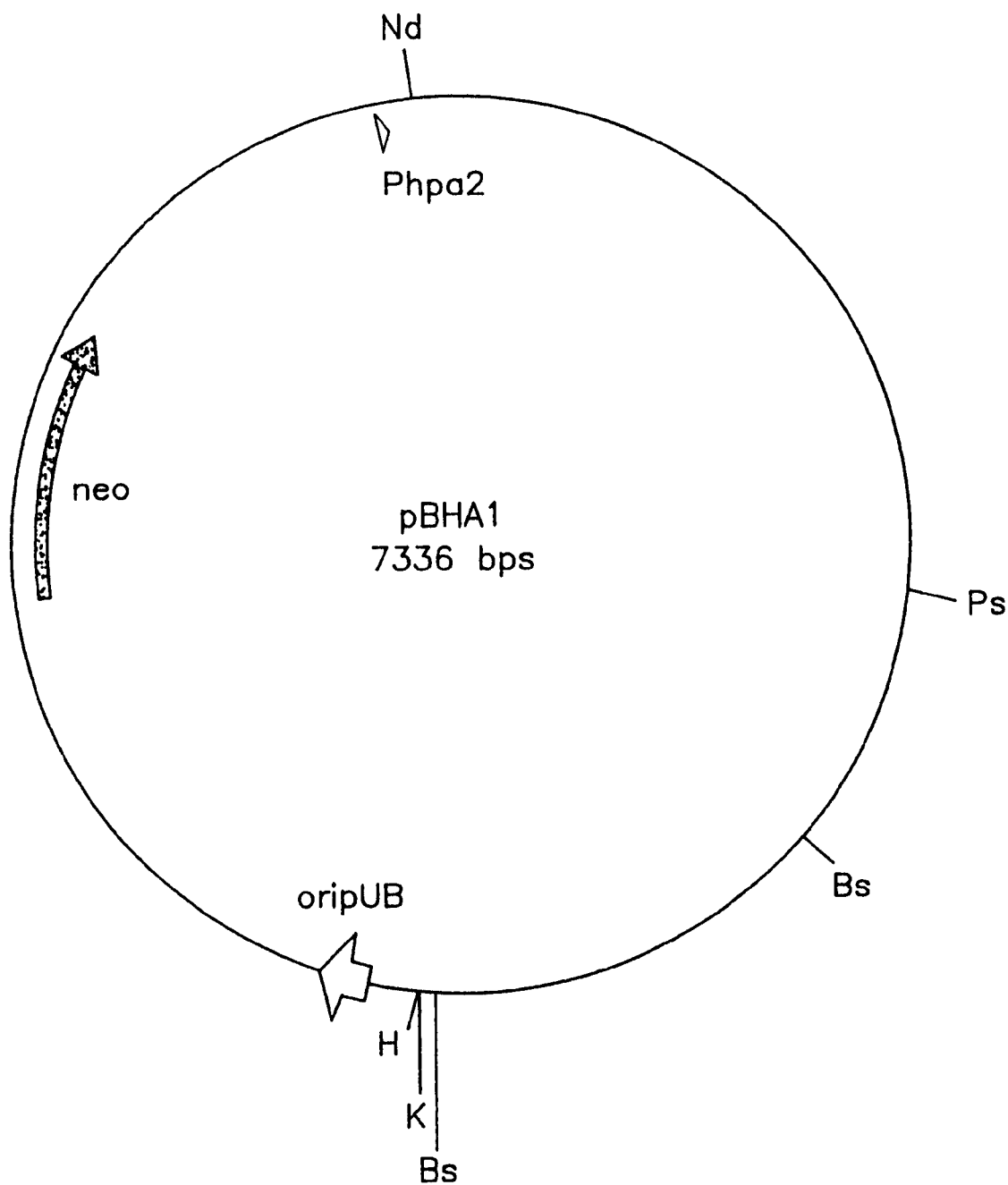

FIG. 45: restriction map of the Bacillus plasmid pBHA1.

Figure 46:
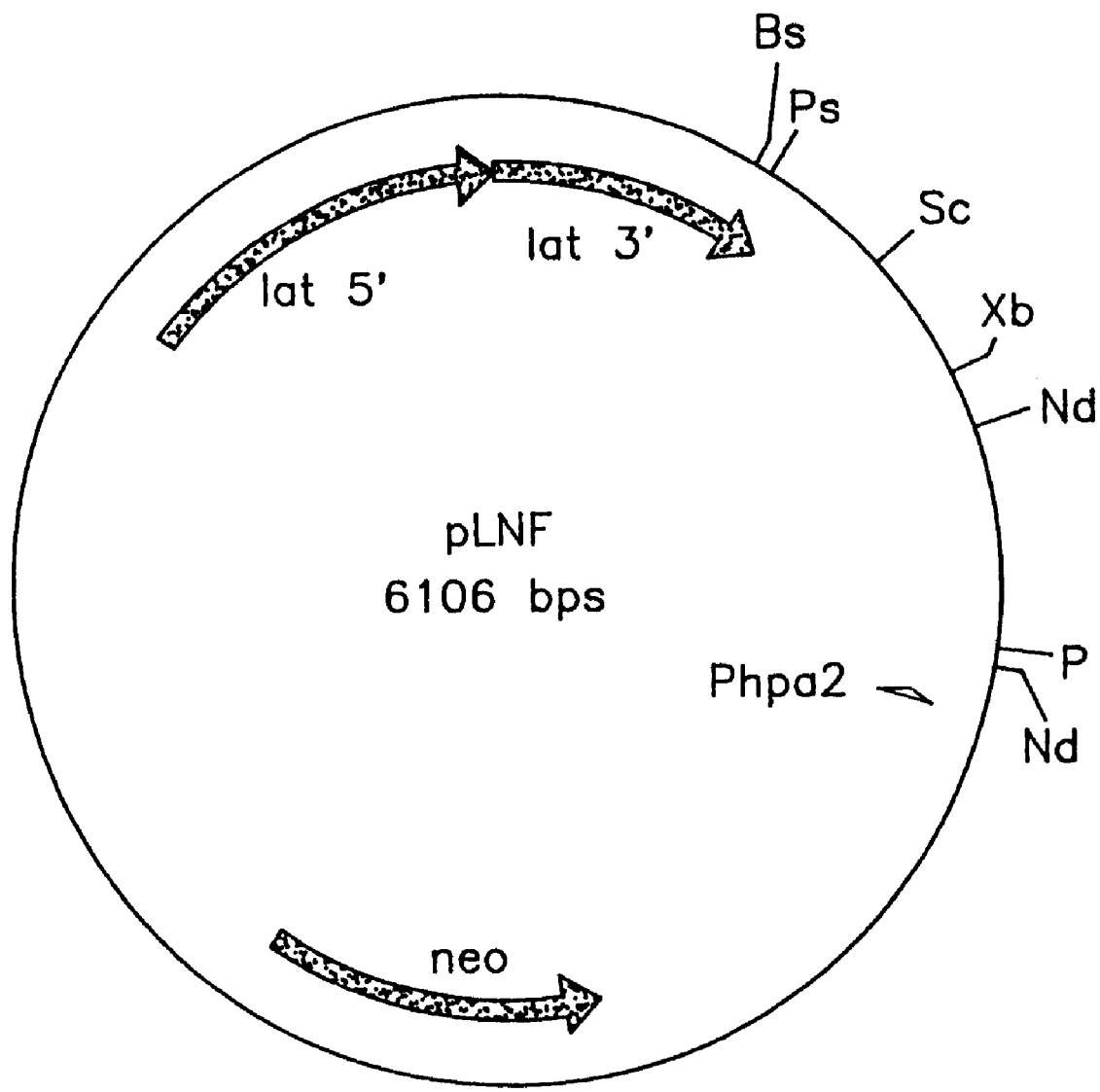

FIG. 46: restriction map of the Bacillus plasmid pLNF.

Figure 47:
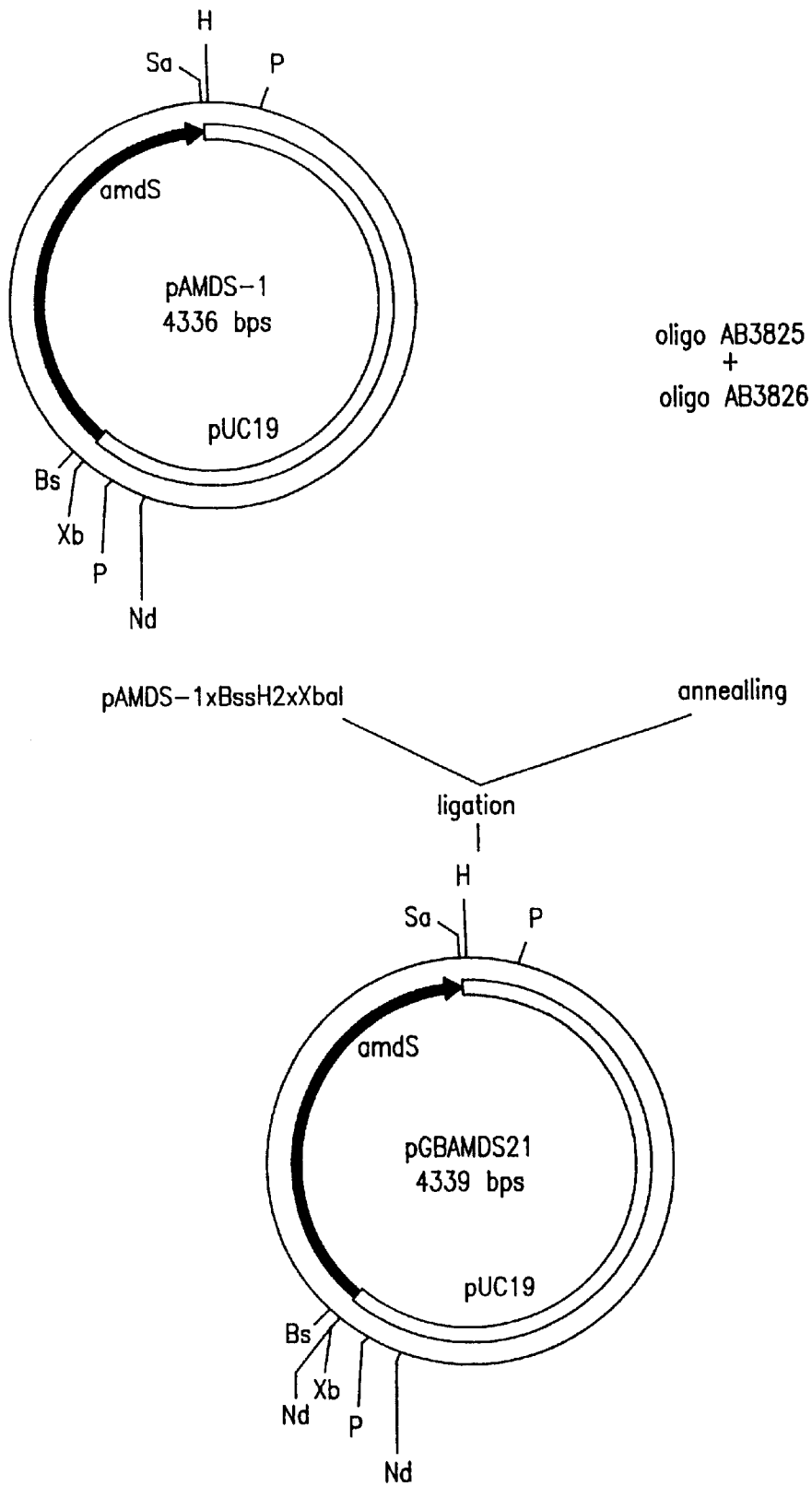

FIG. 47: shows schematically the construction of pGBamdS21.

Figure 48:
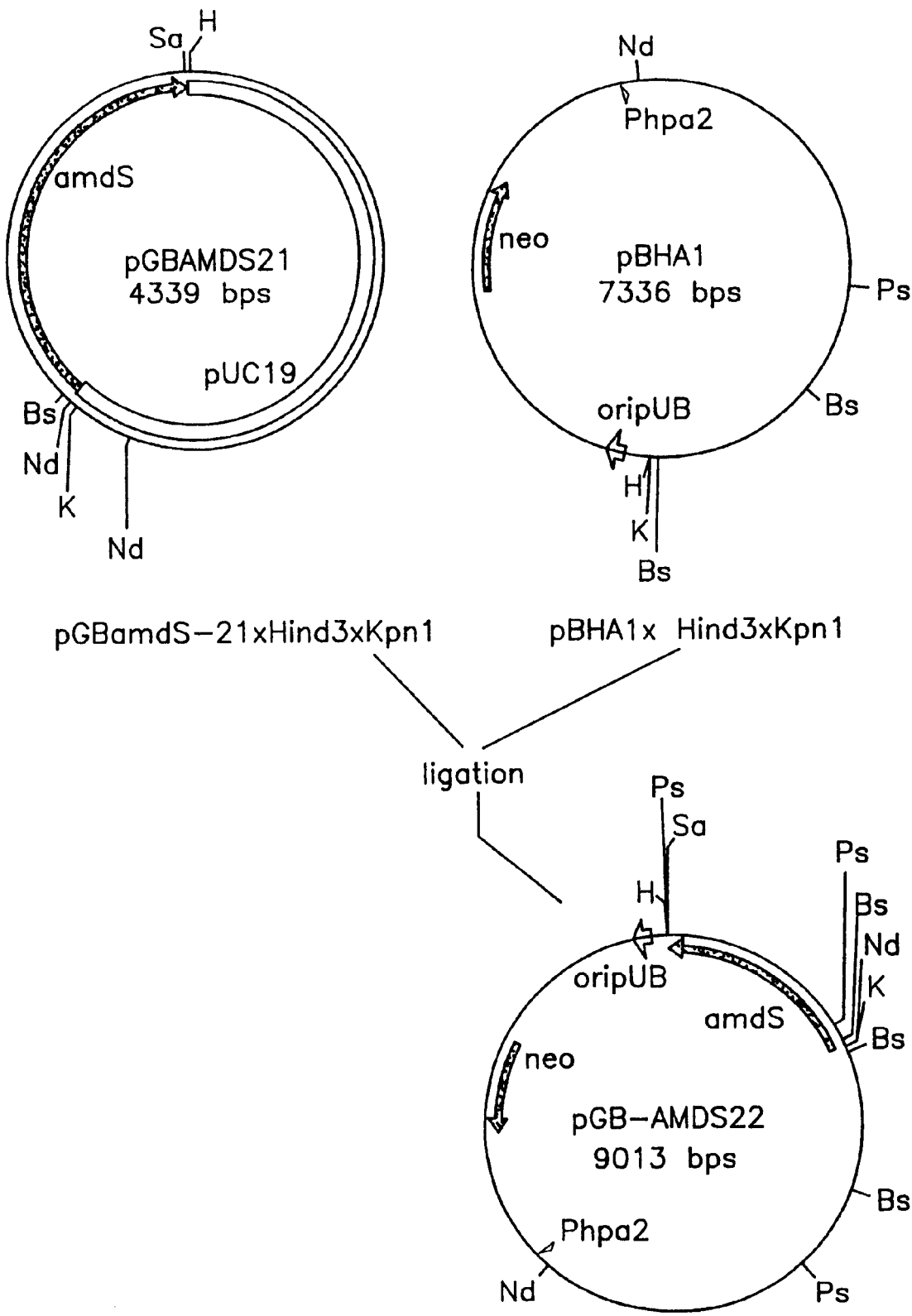

FIG. 48: shows schematically the construction of pGBandS22.

Figure 49:
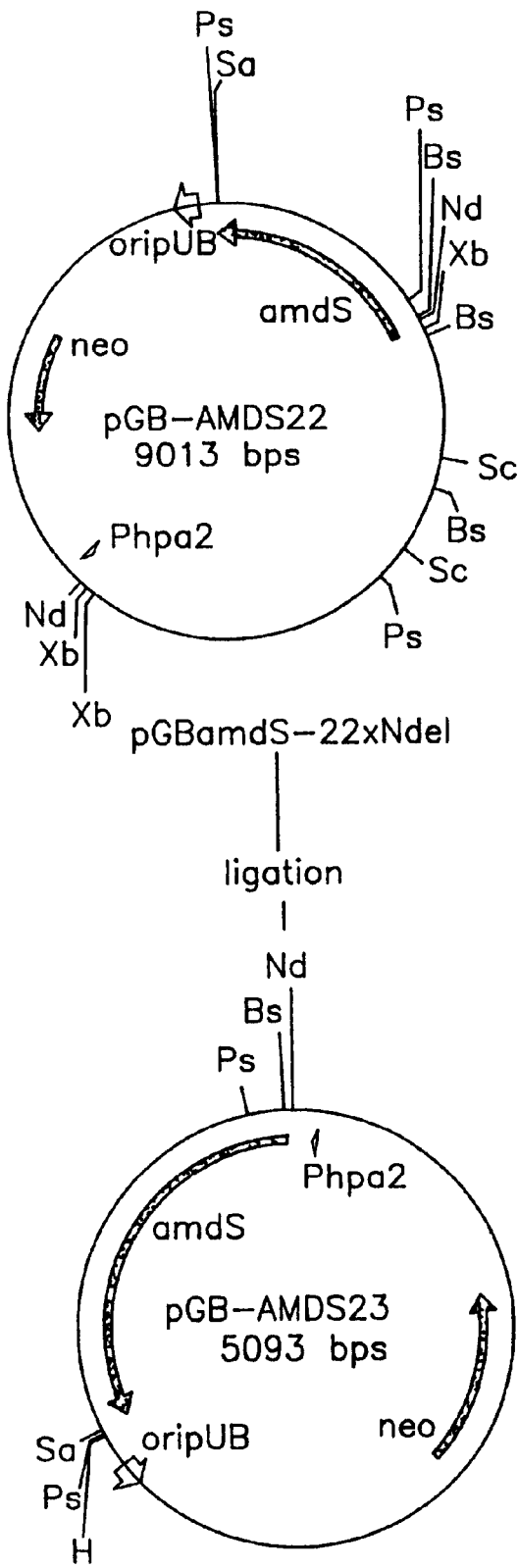

FIG. 49: shows schematically the construction of pGBamdS23.

Figure 50:
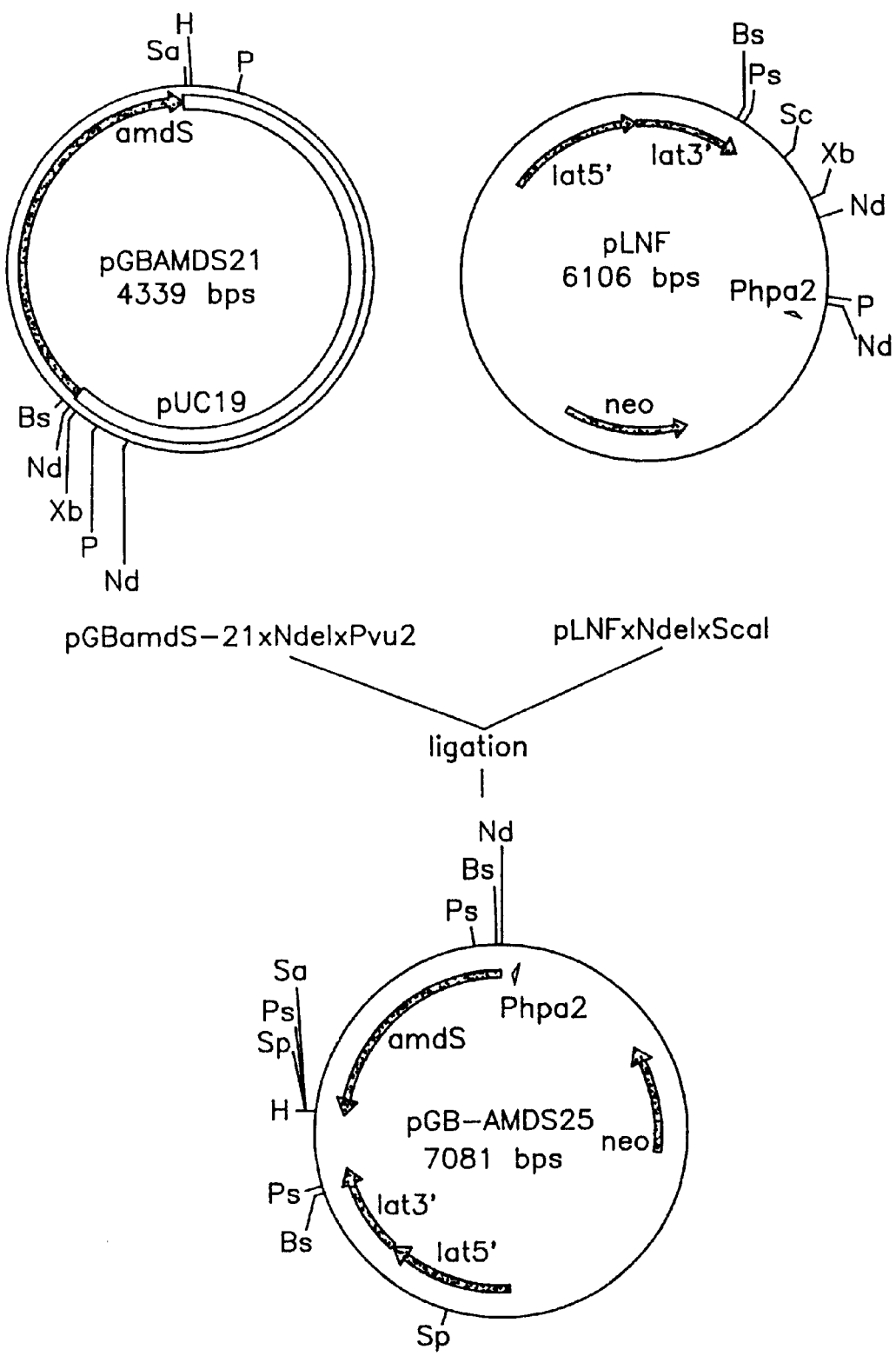

FIG. 50: shows schematically the construction of pGBamdS25.

Figure 51:
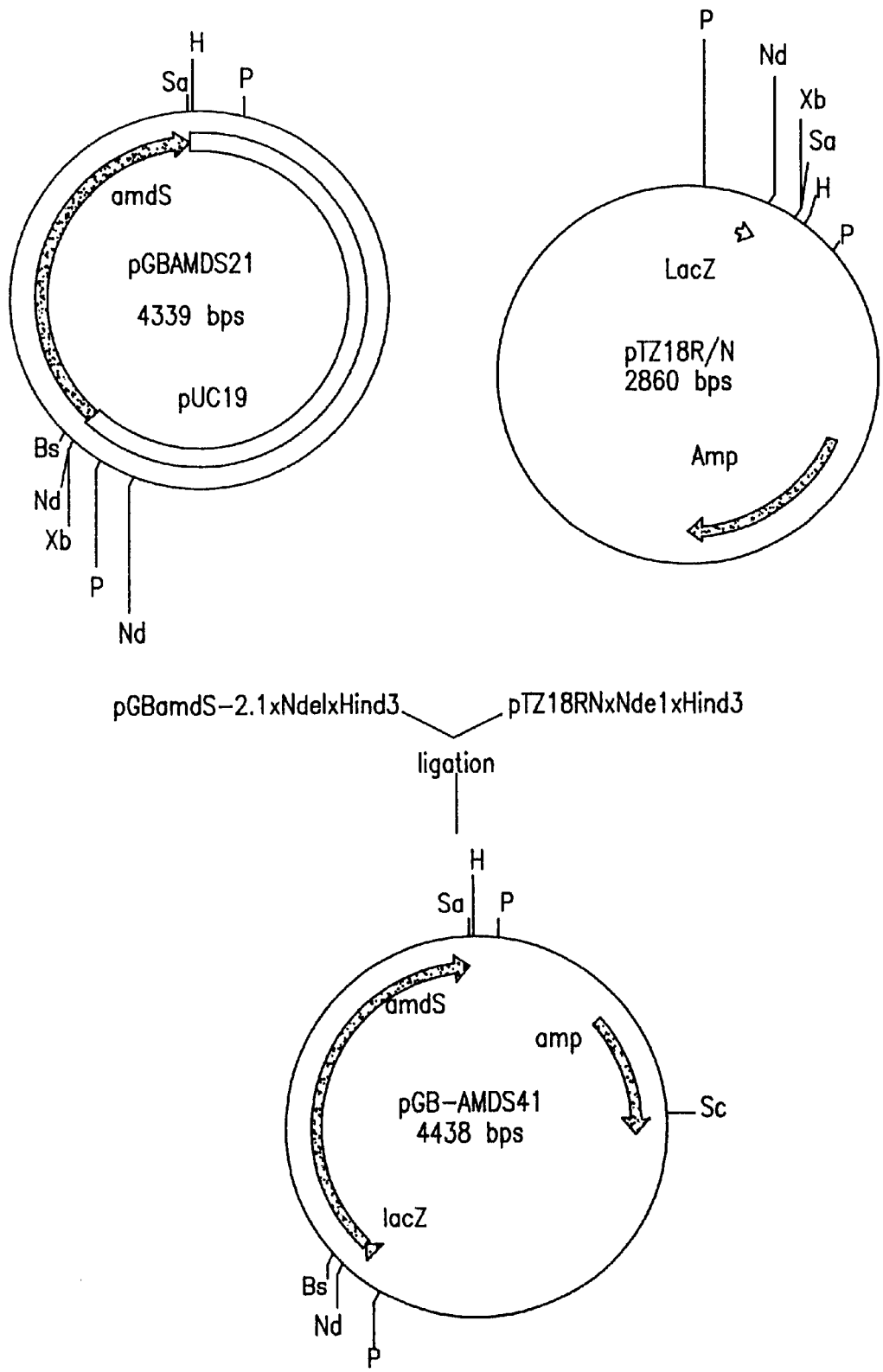

FIG. 51: shows schematically the construction of pGBamdS41.

DETAILED DESCRIPTION OF THE INVENTION

The present invention discloses the use of a marker for selecting transformed host strains. The selection marker gene can be used on an episomal DNA vector. However, in the present invention, the marker gene is preferably integrated into the genome of the host strain. The advantage of the selection marker of the present invention is that it is a non-antibiotic dominant selection marker. Another advantage of the selection marker of the present invention is that it can be easily deleted from the transformed host organism. The deletion of the marker is based on dominant selection. As such the selection marker of the present invention is a dominant and bi-directional selection marker. To our knowledge it is the only selection-marker available which is bidirectional and dominant in both directions.

In the present description we use the term 'selection marker gene'. With this term we mean the DNA coding for the marker protein in a functional form irrespective of whether it is the actual gene or the cDNA derived therefrom. The gene or cDNA is used dependent on the host organism and the expected splicing problems.

In the present invention we use the term 'vector'. By this is intended any DNA molecule that can be introduced into a selected host irrespective of whether the vector integrates into the genome of the host cell or remains episomal. The vector contains a selectable marker gene functional in the selected host or can be co-transformed with another DNA molecule containing such a selection marker gene.

The present description uses the term 'desired heterologous or homologous genes or DNA fragments'. By this is intended a DNA fragment that may be obtained from the host strain or from another species or strain. The desired DNA fragment may contain any genetic element, parts thereof or combinations thereof, such as a gene (coding part or complete locus), a cDNA, a promoter, a terminator, an intron, a signal sequence, any regulatory DNA sequence or recognition sequences of DNA-binding proteins. The fragment may also be a DNA sequence that has been modified i.e. contains one or more nucleotide alterations (e.g. insertions, deletions, substitutions).

The present description further uses the term 'introduction' of a desired gene or DNA fragment. By this is intended an insertion, deletion, substitution of desired DNA sequences in a selected host cell.

The term 'genetic modification' used in the present invention refers to any modification of DNA sequences in a selected host cell which is the result of the introduction of any one of the above mentioned desired DNA fragments into the host cell, preferably by transformation or co-transformation In general all these genetic modifications can be performed using the method of the present invention with subsequent deletion of the selection marker gene. Due to the fact that the recombinant strain containing such a genetic modification does not contain the selection marker gene, the procedure of the present invention can be repeated, so that the modifications suggested above can be combined in the recombinant strain. Ultimately, the procedure of the present invention can be used repeatedly up to the point that a recombinant strain is obtained from which all undesired activities have been removed by deletion or inactivation of the corresponding genetic elements and which contains the desired activities at the desired levels by sequential introduction of the corresponding desired DNA fragments at desired copynumbers and preferably at desired and defined loci.

The A. nidulans acetamidase (amdS) gene allows A. nidulans to grow on acetamide as the sole N-source. For microorganisms that lack the possibility or only have a very limited capacity to use acetamide as the sole N-source the acetamidase gene can in principle be used as a selection marker provided that acetamide is taken up by the cells. The amdS gene has successfully been employed as a marker gene in Aspergilli (Kelly and Hynes (1985) EMBO J. 4, 475–479; Christensen et al. (1988) Bio/technology 6, 1419–1422), Penicillium (Beri and Turner (1987) Curr. Genet. 11, 639–641) and Trichoderma (Pentillä et al. (1987) Gene 61, 155–164).

The present invention for the first time discloses the use of the amdS gene from A. nidulans as a selection marker in organisms other than filamentous fungi. The use of this selection marker is disclosed in bacteria and yeasts. Specifically, the use is demonstrated in S. cerevisiae, in K. lactis in B. subtilis, in B. licheniformis and in E. coli. In view of the disclosed applicability of the selection marker in species selected from such diverse groups as fungi, yeasts and bacteria it is to be expected that the marker will also be applicable in other species pertaining to these groups. Use of this marker is therefore not restricted to the disclosed species.

The amdS gene from A. nidulans is capable of converting acetamide to ammonia and acetic acid. This property enables A. nidulans to grow on a medium containing acetamide as the sole N-source or C-source.

Another property of the amdS gene is that it is also able to convert fluoracetamide to ammonia and fluoracetic acid. Fluoracetic acid however is toxic to the cell. It is this property that forms the basis for another aspect of the present invention i.e the production of marker gene free recombinant strains. The fluoracetamide converting property enables the counter-selection of transformed cells. The amdS gene is introduced into the host strain and integrated into the genome through homologous recombination. The transformed strains are selected on a medium containing acetamide as the sole N-source. Subsequently the selected strains are grown on a medium containing fluoracetamide and urea (or other preferably defined N-sources) as the sole N-sources. The surviving strains will have deleted the amdS gene.

The present invention uses the A. nidulans amdS gene as acetamidase marker gene. The relevant properties provided by the acetamidase encoded by the A. nidulans amdS gene, i.e. the ability to hydrolyse acetamide into ammonia and acetate as well as the ability to liberate fluoracetic acid from fluoracetamide, can also be provided by acetamidases from other sources. Use of an acetamidase marker gene is therefore not restricted to the A. nidulans amdS gene but includes any DNA sequence encoding a functional acetamidase.

The frequency of marker deletion is substantially increased by increasing the capacity of the gene for intrachromosomal homologous recombination. To achieve this the amdS gene is preferably placed between DNA repeats. These repeats are not necessarily both present in the vector but may also be created by a single cross-over integration. Alternatively, one may omit flanking repeats and rely on other mechanisms for removal or inactivation of the marker gene. In that case, however, the outcome may be less predictable and may not result in removal but rather in mere inactivation of the marker gene.

The vector may be constructed in such a way that, after deletion of the marker gene, no extraneous foreign DNA (except the DNA of interest) remains in the chromosome of the host strain. The invention discloses a vector comprising:
a) a desired DNA fragment destined for introduction into the host genome,
b) optionally a DNA sequence that enables the vector to integrate (site-specifically) into the genome of the host strain,
c) a gene encoding an acetamidase (e.g. the amdS gene from A. nidulans) between DNA repeats.

Identical results may be obtained when the DNA-fragment destined for introduction into the host genome and the selectable marker gene (e.g. the acetamidase gene) are present on two different DNA molecules which are co-transformed, in which case the DNA molecule containing the selectable marker does not necessarily integrate into the host genome but may be present on an episomal DNA molecule which can be cured.

The sequences used for integration as mentioned under b) are used if site-specific (or better locus specific) integration is desired. If such a sequence is not present the vector nevertheless may integrate into the genome. This does not influence the ability to delete the selection marker gene.

The dominant counter-selection described above can be employed in the development of industrial production strains in various ways. The use of a dominant selection marker is especially advantageous in the development of improved production strains due to the fact that these strains are often diploid or polyploid.

The vector used for integration of the amdS gene preferably contains another gene of interest. The invention thus further enables the introduction of desired foreign or homologous genes or DNA elements in the host organisms of choice using the amdS gene as a marker. Subsequently the amdS gene is deleted. Preferably, the amdS and the desired genes or DNA elements are introduced site-specifically, whereafter the amdS gene is deleted.

Specifically, the invention discloses organisms containing site-specifically introduced genes without any further foreign DNA being present. The invention is used for integration of multiple copies of a desired gene or a DNA element at predetermined genomic loci.

The invention provides a method for obtaining selection of marker gene free recombinant strains comprising the following steps:
integration of a desired gene or DNA element and a selection marker by homologous recombination between sequences incorporated in an expression cassette and sequences on the host chromosome,
selection using the selection marker gene that is dominant,
deletion of the selection marker gene using selection marker gene flanking regions,
selection based on the absence of the selection marker gene (counter-selection).

The present invention further shows that this marker gene can be deleted from the chromosomes of the transformed organisms without leaving a trace i.e. DNA used for cloning. Moreover, the invention also shows that similar if not identical results can be obtained when the desired gene or DNA element and the selection marker are present on two different DNA molecules which are co-transformed.

Finally the invention discloses the use of the amdS gene for deleting a desired gene from the chromosome of at 'host' organism.

In view of the above, the method of the present invention is ideally suited for, but not limited to the cloning and expression of genes coding for proteins used in food, feed or pharmaceutical applications or genes involved in biosynthesis of antibiotics and other bio-active compounds, i.e. recombinant proteins and/or hosts-organisms that are subject to strict registration requirements.

Examples of such proteins are well known in the art and include chymosin, phytase, xylanases, amylases, cellulases and hemicellulases, cytokines and other pharmaceutical proteins, etc.

The same method is employed for deletion of genes coding for proteins that influence production levels of desired proteins again without leaving a marker gene in the genome. Such proteins include proteases which actively digest the desired products that are highly expressed in the host strain and that therefore have a reduced potential of producing and or secreting the desired proteins. A preferred method for the deletion of a given gene would use a DNA construct containing the following elements in a 5' to 3' order: sequences 5' of the gene to be deleted, directly fused to sequences 3' of the gene to be deleted, followed downstream by a functional selection marker gene (preferably an acetamidase gene), followed downstream by again sequences 3' of the gene to be deleted. In this case both sequences 3' of the gene to be deleted are chosen such that they form repeats flanking the selection marker gene. Transformation of this DNA construct and subsequent replacement of the chromosomla copy of the gene to be deleted by the DNA construct with cross-over points in the sequences 5' and 3' of the gene to be deleted results in deletion of the given gene. Subsequent intrachromosmal recombination between the repeats flanking the selection marker gene and counter-selection for these recombinants finally results in a selection marker free strain with the given gene deleted. The DNA construct used for this deletion can be constructed such that no foreign DNA or other traces of the genetic modification are left in the strain carrying the deletion.

The invention discloses selection marker gene free recombinant microorganisms. Such microorganisms can be organisms that, after the use of the disclosed technology, contain an extra copy of a desired gene (either homologous or heterologous). Such microorganisms can be re-transformed over and over by sequential application of the same technology to insert or delete additional copies of the same or other gene(s) of interest.

The microorganisms may also be characterized in that they have (a) predetermined gene(s) deleted or altered in any desired way.

The method of the present invention makes possible the fine-tuning of the production of desired proteins. This possibility is based on the ease with which repeated rounds of insertion and deletion can be performed. The method makes possible the insertion or deletion of a desired number of gene copies. Thus the proteins are produced in desired amounts and in desired ratios. This is especially useful for the production of mixtures of proteins or enzymes.

Whereas it is known that the acetamidase gene is capable of conversion of acetamide as the sole N-source in Aspergillus it is here shown that the acetamidase gene is easily deleted from the genome of transformed Aspergilli. To achieve this the amdS gene is cloned between direct repeats. In principle any direct repeat which allows for internal recombination can be employed. In the present examples this is demonstrated by cloning the amdS gene between 3' amyloglucosidase (glaA) non-coding DNA sequences.

It is shown that the amdS gene can be integrated and deleted upon plating on medium containing fluoracetamide and urea as N-sources.

It is further demonstrated that the amyloglucosidase gene can be deleted from the genome of Aspergillus. A replacement vector is constructed containing a part of the glaA promoter, a synthetic DNA sequence containing stop codons in all three reading frames, the amdS gene from *A. nidulans* under the control of the *A. nidulans* glyceraldehyde-3-phosphate dehydrogenase promoter and wherein the amdS gene is flanked by 3' glaA non-coding sequences. After transformation of *A. niger* the vector is integrated by double crossing-over thereby effectively replacing the amyloglucosidase gene. After selection for amdS activity the transformed strains are plated on fluoracetamide and urea. Selection resulted in strains wherein the amdS gene was, deleted.

This example is an illustration of the possibility of using the amdS gene for deletion of a desired gene from the genome of an Aspergillus strain. Other genes can be eliminated or modified in a similar manner.

In a further example it is demonstrated that a gene can be inserted marker free at a predetermined site in the genome. An integration vector is constructed containing the *A. niger* glaA locus and the amdS gene flanked by two 3' glaA non-coding repeats.

The construct is shown to integrate at the amyloglucosidase locus. After selection on fluoracetamide the amdS gene is deleted. In this way a gene copy is integrated at a specific locus without leaving marker DNA.

It is evident from the above that the procedures described herein enable one of skill in the art to integrate or delete desired genes at predetermined loci without leaving selection marker DNA behind.

This method can be employed for gene amplification and gene replacement.

An especially important application would be the integration of desired genes. Followed by classical strain improvement whereafter the genes that may be adversely affected by the classical strain improvement techniques are replaced with fresh unaffected copies of the gene of interest without loss of expression level.

The system as described for Aspergillus above is expected to give the same results when other fungal strains are employed, which are known to be incapable of growth on acetamide as the sole N-source. The use of the amdS gene as a selection marker has been described for among others Penicillium and Trichoderma. Moreover, the amdS gene can even be used in filamentous fungi which are capable of using acetamide as sole N-source albeit poorly. In this case the background of poorly growing untransformed cells can be repressed by the inclusion of CsCl in the selection media (Tilburn, J. et al. (1983) Gene, 26, 205–221). Hence the system is expected to be applicable to filamentous fungi in general.

In one embodiment of the present application it is surprisingly demonstrated that the *A. nidulans* amdS gene can be used as a selection marker in *K. lactis*. In this Example it is shown that two different *K. lactis* strains cannot grow on acetamide as the sole N-source. The two *K. lactis* strains are plated on YCB medium which is a) complete but without N-source, b) as a) but with acetamide, c) as a) but with ammonium sulphate.

It is shown that the strains do not grow on the medium under b) but do grow on medium under c). Hence provided that the acetamide is taken up by the yeast cells and that the amdS gene can be expressed in *K. lactis* the system is applicable in yeasts also at least as a selection marker. Concerning the counter-selection using fluoracetamide some further requirements have to be met. Fluoracetate is toxic when activated by the enzyme acetyl-CoA-synthetase. Prerequisites for the fluoracetamide counter-selection to also work on amdS yeasts are therefore 1) fluoracetamide should not be toxic for amdS⁻ yeasts, 2) the yeast cell wall and plasmamembrane should be permeable to fluoracetamide and 3) the enzyme acetyl-CoA-synthetase should be active.

To test this the amdS gene was cloned in *K. lactis*.

To avoid any potential splicing problems of the *A. nidulans* amdS gene in *K. lactis* the amdS cDNA from *A. nidulans* was cloned as shown in the Experimental section.

Subsequently the amdS was cloned downstream of a yeast promoter (LAC4, ADH1, KlEF) in a vector containing another marker (phosphotransferase-G418). This cloning is described in Example 8. The vectors containing both the G418 marker and the amdS gene were selected using the G418 marker and were then used to optimize selection conditions for the amdS+ phenotype.

Direct selection of *K. lactis* is shown in another embodiment of the present invention and for *S. cerevisiae* direct selection is shown in Example 11.

Subsequently it is demonstrated that counter-selection can be employed on the transformed yeast strains to remove the amdS gene.

The amdS gene system is used for both marker gene free insertion and marker gene free deletion of a gene in yeast.

In a further embodiment the lactase gene is deleted from *K. lactis* whereas in Example 14 a copy of the chymosin gene is inserted into the *K. lactis* genome.

The genes used here for insertion and deletion are only used as examples. The same technology can be applied using other genes or DNA elements. As mentioned before the DNA fragments used for insertion or deletion can be mutated genes, promoter sequences, regulatory sequences etc. In all cases it is possible to insert or delete these sequences at desired genomic sites and in desired numbers, without leaving a marker gene behind.

The feasibility of the use of this system in other yeast strains is evident.

As a first step for use of the system of the present invention in bacteria it is shown in Example 15 that *Bacillus subtilis* and *E. coli* cannot grow on acetamide as the sole N-source.

Example 16 describes the vectors that have been constructed for use in Bacillus and *E. coli*.

It is demonstrated in Examples 17 and 18 that the amdS gene can be effectively used in Bacillus and *E. coli* as selection marker, whereas Example 19 demonstrate the fluoracetamide counter-selection of bacterial amdS+ transformants.

The advantages of the system of the present invention are manifold. The most striking advantages are given below:

- It is demonstrated that the amdS system is universally applicable (plant cells, animal cell, yeasts, bacteria and filamentous fungi etc.), requiring only that the host in question cannot or only poorly grow on acetamide as sole C- or N-source but can utilize either acetate or ammonia as sole C- or N-source, respectively.
- The amdS system represents the only bi-directional and dominant selection system. This feature is extremely convenient for use in poly- or aneuploid strains which often is the case with natural isolates and/or industrial strains.
- After classical strain improvement any mutated copies of the desired gene can be easily replaced by unmutated copies by gene replacement due to the fact that the desired genes have been integrated at well-defined loci. The genes are thus replaced with unmutated genes without affecting the expression level.
- Due to the ability to introduce multiple integrations at well-defined and therefore non-random loci one can be assured that no undesirable traits arise in the strain upon gene amplification.
- The growing concern about the release of various selection markers in the environment is overcome by the presented system. No selection marker gene or other unnecessary or undesired DNA sequences need to present in the production strains after introduction of the desired genes or other genetic modifications.

Experimental
General Molecular Cloning Techniques

In the examples described herein, standard molecular cloning techniques such as isolation and purification of nucleic acids, electrophoresis of nucleic acids, enzymatic modification, cleavage and/or amplification of nucleic acids, transformation of *E. coli*, etc., were performed as described in the literature (Sambrook et al. (1989) "Molecular Cloning: a laboratory manual", Cold Spring Harbour Laboratories, Cold Spring Harbour, N.Y.; Innis et al. (eds.) (1990) "PCR protocols, a guide to methods and applications" Academic Press, San Diego). Synthesis of oligodeoxynucleotides and DNA sequence analysis were performed on an Applied Biosystems 380B DNA synthesizer and 373A DNA sequencer, respectively, according to the user manuals supplied by the manufacturer.

Transformation of *A. niger*

Transformation of *A. niger* was performed according to the method described by Tilburn, J. et. al. (1983) Gene 26, 205–221 and Kelly, J. & Hynes, M. (1985) EMBO J., 4, 475–479 with the following modifications:

- spores were grown for 16 hours at 30° C. in a rotary shaker at 300 rpm in Aspergillus minimal medium. Aspergillus minimal medium consists of the following components: Per liter: 6 g $NaNO_3$; 0.52 g KCl; 1.52 g $KH_2PO_4$; 1.12 ml 4M KOH; 0.52 g $MgSO_4.7H_2O$; 10 g glucose; 1 g casamino acids; 22 mg $ZnSO_4.7H_2O$; 11 mg $H_3BO_3$; 5 mg $FeSO_4.7H_2O$; 1.7 mg $CoCl_2.6H_2O$; 1.6 mg $CuSO_4.5H_2O$; 5 mg $MnCl_2.4H_2O$; 1.5 mg $Na_2MoO_4.2H_2O$; 50 mg EDTA; 2 mg riboflavin; 2 mg thiamine.HCl; 2 mg nicotinamide; 1 mg pyridoxine.HCl; 0.2 mg panthotenic acid; 4 $\mu$g biotin; 10 ml Penicillin (5000 IU/ml)/Streptomycin (5000 UG/ml) solution (Gibco).
- only NOVOZYM 234 (Novo Industri), and no helicase, was used for formation of protoplasts;
- after protoplast formation (60–90 minutes), KC buffer (0.8M KCl, 9.5 mM citric acid, pH6.2) was added to a volume of 45 ml, and the protoplast suspension was centrifuged at 2500 g at 4° C. for 10 minutes in a swinging-bucket rotor. The protoplasts were resuspended in 20 ml. KC buffer. Then, 25 ml of STC buffer (1.2M sorbitol, 10 mM Tris-HCl pH7.5, 50 mM $CaCl_2$) was added and subsequently the protoplast suspension was centrifuged at 2500 g at 4° C. for 10 minutes in a swinging-bucket rotor, washed in STC-buffer and resuspended in STC-buffer at a concentration of $10^8$ protoplasts/ml;
- to 200 $\mu$l of the protoplast suspension the DNA fragment, in a volume of 10 $\mu$l in TE buffer (10 mM Tris-HCl pH7.5, 0.1 mM EDTA), was added and subsequently 100 $\mu$l of a PEG solution (20% PEG 4000 (Merck), 0.8M sorbitol, 10 mM Tris-HCl pH7.5, 50 mM $CaCl_2$);
- after incubation of the DNA-protoplast suspension at room temperature for 10 minutes, 1.5 ml PEG solution (60% PEG 4000 (Merck), 10 mM Tris-HCl pH7.5, 50 mM $CaCl_2$) was added slowly, with repeated mixing of the tubes. After incubation at room temperature for 20 minutes, the suspensions were diluted with 5 ml STC buffer, mixed by inversion and centrifuged at 2000 g at room temperature for 10 minutes. The protoplasts were resuspended gently in 1 ml 1.2M sorbitol and plated onto selective regeneration medium consisting of Aspergillus minimal medium without riboflavin, thiamine.HCl, nicotinamide, pyridoxine.HCl, panthotenic acid, biotin, casamino acids and glucose but with 10 mM acetamide as the sole nitrogen source, 1M sucrose, solidified with 2% bacteriological agar #1 (Oxoid, England). Following growth for 6–10 days at 30° C., the plates were replica plated onto selective acetamide plates consisting of Aspergillus selective regeneration medium with 2% glucose instead of sucrose and 1.5% agarose instead of agar. Single transformants were isolated after 5–10 days of growth at 30° C.

Transformation of *A. oryzae*

Transformation of *A. oryzae* was performed according to the method described by Christensen, T. et al. in European Patent Application 0 238 023 A2.

Transformation of *T. reesei*

Transformation of *T. reesei* was performed according to the method described by Penttilla M., Knowles, J. (1987) Gene 61 155–164.

Transformation of *P. chrysogenum*

The Ca-PEG mediated protoplast transformation procedure is used. Preparation of protoplasts and transformation of *P. chrysogenum* was performed according to the method described by Gouka et al., Journal of Biotechnology 20(1991), 189–200 with the following modifications:

After transformation, the protoplasts were plated onto selective regeneration medium plates consisting of Aspergillus minimal medium, osmotically stabilized with 1.2M sucrose, containing 0.1% acetamide as sole nitrogen source and solidified with 1.5% bacteriological agar #1 (Oxoid, England).

After 5–8 days of incubation at 25° C. transformants appeared.

Transformation of *K. lactis*

The yeast *K. lactis* was transformed using the lithium acetate procedure described by Ito H. et al. (1983) J. Bacteriol. 153, 163–168 with the following modifications:

For transformation a *K. lactis* culture was taken with an $OD_{610}$ between 0.5 and 1.0.

After the 5 minutes heatshock of the transformed cell suspensions, 1 ml YEPD/YNB (1% yeast-extract, 2% BACTO-PEPTONE, 2% glucose and 0.17% Yeast Nitrogen Base w/o amino acids (YNB; Difco) was added and the cell-suspensions were incubated at 30° C. in a shaker incubator for 150–180 minutes.

After the above mentioned incubation (at 30° C. for 150–180 minutes), the cell-suspensions were centrifuged at:

2000 g at room temperature for 5 minutes and plated on YEPD/G418 double layer medium solidified with 2% Bacto-agar (Difco). YEPD/G418 double layer plates were prepared as followed: 10 minutes prior to plating of the cell-suspensions 15 ml YEPD agar (1% yeast-extract 2% BACTO-PEPTONE, 2% glucose solidified with 2% BACTO-AGAR (Difco)) without G418 was poured onto 15 ml YEPD agar, which contained 50 μg G418/ml. This results in YEPD/G418 double layer plates which contain 25 μg G418/ml after diffusion of the antibiotic. The YEPD/G418 double layer plates contained 25 μg G418/ml or 100 μg G418/ml in case of strains *K. lactis* CBS 683 or CBS 2360, respectively.

Isolation of DNA from Aspergillus, Trichoderma, Penicillium and Yeast

The isolation of DNA from Aspergillus and Trichoderma was performed according to the procedure as described by Yelton, et al. (1984), Proc. Natl. Acad. Sci. 81, 1470–1474.

The isolation of DNA from Penicillium was performed according to the procedure described by Kolar et al., Gene 62 (1988), 127–134.

The isolation of DNA from *K. lactis* or *S. cerevisiae* was performed according to the procedures described by Fujimura and Sakuma (1993), Biotechniques 14, 538.

Bacillus Transformation and DNA-Isolation

Transformation of the different Bacillus species as well as isolation of plasmid or chromosomal DNA from these species was performed as described by Bron (1990) "Plasmids" In: Molecular Biological Methods for Bacillus, Harwood, CR and Cutting, SM, eds., series Modern Microbiological Methods, John Wiley & Sons, Chichester, UK.

For the transformation of *B. subtilis* BS-154 (CBS 363.94) competent cells were used and for the transformation of *B. licheniformis* T5 (CBS 470.83) protoplast transformation lo was used. In the case of neomycin selection a concentration of 20 μg/ml was used. For acetamide selection of *B.subtilis* transformants, minimal medium agar was used in which casamino acids and yeast extract were replaced by 20 mM acetamide. For acetamide selection of *B. licheniformis* transformants, protoplast regeneration medium was used in which ammonium sulphate was replaced by 20 mM acetamide.

Removal of the amdS Selection Marker

The amdS marker in most examples relating to Aspergillus, Trichoderma and Penicillium is cloned between repeats consisting of a part of the 3' non-coding region of amyloglucosidase gene. Removal of the amdS selection marker is achieved either by internal recombination between the 3' non-coding repeats that flank the amdS selection marker or by homologous recombination between the repeats that are created by integration via a single cross-over event. Selection of cells that have lost the amdS selection marker is achieved by growth on plates containing fluoracetamide. Cells harbouring the amdS gene metabolize fluoracetamide to ammonium and fluoracetate which is toxic to the cell. Consequently, only cells that have lost the amdS gene are able to grow on plates containing fluoracetamide.

In case of removal of the amdS marker from Aspergillus transformants, spores from these transformants were plated onto selective regeneration medium (described above) containing 32 mM fluoracetamide and 5 mM ureum instead of 10 mM acetamide, 1.1% glucose instead of 1M sucrose and 1.1% instead of 2% bacteriological agar #1 (Oxoid, England). After 7–10 days of growth at 35° C. single colonies were harvested and plated onto 0.4% potato dextrose agar (Oxoid, England). In case of removal of the amdS marker from Trichoderma transformants, spores of these transformants were plated onto non selective minimal medium plates (per liter: 20 g. glucose, 5 g. $(NH_4)_2SO_4$, 15 g. $KH_2PO_4$, 0.6 g. $MgSO_4$, 0.6 g. $CaCl_2$, 0.005 g. $FeSO_4.7H_2O$, 0.0016 g. $MnSO_4.H_2O$, 0.0014 g. $ZnSO_4.7H_2O$, 0.002 g. $CoCl_2$; pH5.5) supplemented with 10 mM fluoracetamide. After 5–10 days at 30° C., colonies were harvested and plated onto 0.4% potato dextrose agar (Oxoid, England).

In case of removal of the amdS marker from Penicillium transformants, spores from these transformants were plated on selective medium plates consisting of Aspergillus minimal medium with 10 mM fluor-acetamide and 5% glucose, solidified with 1.5% bacteriological agar #1 (Oxoid, England). After 5–10 days of growth at 25° C. resistant colonies appeared.

Determination of Glucoamylase Production by *A. niger* Transformants

Of recombinant and control *A. niger* strains spores were collected by plating spores or mycelia onto PDA-plates (Potato Dextrose Agar, Oxoid), prepared according to the supplier's instructions. After growth for 3–7 days at 30° C.

spores were collected after adding 0,01% Triton X-100 to the plates. After washing with sterile water approximately $10^7$ spores of selected transformants and control strains were inoculated into shake flasks, containing 20 ml of liquid pre-culture medium containing per liter: 30 g maltose.$H_2O$; 5 g yeast extract; 10 g hydrolysed casein; 1 g $KH_2PO_4$; 0.5 g $MgSO_4.7H_2O$; 3 g Tween 80; 10 ml Penicillin (5000 IU/ml)/Streptomycin (5000 UG/ml); pH 5.5. These cultures were grown at 34° C. for 20–24 hours. 5–10 ml of this culture was inoculated into 100 ml of fermentation medium containing per liter: 70 g maltodextrines; 25 g hydrolysed casein; 12.5 g yeast extract; 1 g $KH_2PO_4$; 2 g $K_2SO_4$; 0.5 g $MgSO_4.7H_2O$; 0.03 g $ZnCl_2$; 0.02 g $CaCl_2$; 0.01 g $MnSO_4.4H_2O$; 0.3 g $FeSO_4.7H_2O$; 10 ml penicillin (5000 IU/ml)/Streptomycin (5000 UG/ml); adjusted to pH 5.6 with 4N $H_2SO_4$. These cultures were grown at 34° C. for 5–10 days. Samples were taken for the analysis of the glucoamylase production at different time points during fermentation. Fermentation broth samples were centrifuged (10 minutes, 10.000×g) and supernatants collected.

The glucoamylase activity was determined by incubating 10 μl of a six times diluted sample of the culture supernatant in 0.032M NaAC/HAC pH4.05 with 115 μl of 0.2% (w/v) p-Nitrophenyl α-D-glucopyranoside (Sigma) in 0.032M NaAc/HAc pH 4.05. After a 30 min incubation at room temperature, 50 μl of 0.3M $Na_2Co_3$ was added and the absorption at a wavelength of 405 nm was measured. The $A_{405nm}$ is a measure for the AG production.

Cloning of the amdS cDNA

The A. nidulans amdS gene contains three small introns (Corrick et al. (1987) Gene 53, 63–71). In order to avoid problems caused by incorrect splicing of these introns in yeast or lack of splicing in bacteria, we have used an amdS cDNA for expression in yeasts and bacteria. Cloning of the amdS cDNA from an A. nidulans polyA⁺ RNA preparation has been described by Corrick et al. ((1987), Gene 53, 63–71). In this example we have used the A. niger NRRL 3135 transformant #4, which is transformed by multiple copies of the A. nidulans amdS gene containing plasmid pAF2-2S (van Hartingsveld et al (1993). Gene 127, 87–94). Total RNA was isolated by a direct LiCl precipitation according to a procedure modified from Auffray et al. ((1980) Eur. J. Biochem. 107, 303–314). A. niger spores were allowed to germinate and were grown overnight at 37° C. in a minimal medium (Cove (1966) Biochim. Biophys. Acta 113, 51–56) supplemented with glucose as carbon source and with acetamide as sole nitrogen source. Mycelium was obtained and dried by filtration and subsequently frozen with liquid nitrogen to be grounded. The powder was dispersed in 3M LiCL, 6M urea at 0° C. and maintained overnight at 4° C. Total cellular RNA was obtained after centrifugation at 16.000 g for 30 minutes and two successive extractions with phenol/chloroform/isoamylalcohol (50:48:2). The RNA was precipitated with ethanol and dissolved in 1 ml 10 mM Tris-HCL (pH7.4), 0.5% SDS. For polyA⁺ selection the total RNA sample was heated for 5 minutes at 65° C. and subsequently applied to an oligo(dT)-cellulose column. After several washes with a solution containing 10 mM Tris-HCl pH 7.4, 0.5% SDS and 0.5M NaCl, the polyA⁺ RNA was collected by elution with 10 mM Tris-HCl pH 7.4 and 0.5% SDS and precipitated with ethanol. Approximately 5 μg of the polyA⁺ mRNA was used as template for reverse transcription primed with oligo(dT) primers. The reaction mixture (50 mM Tris-HCl pH 7.6, 10 mM DTT, 6 mM $MgCl_2$, 80 mM KCl, 0.2 mM each dNTP and 0.1 mg BSA/ml) was incubated for 30 minutes at 37° C. with 500 units Murine MLV reverse transcriptase (BRL) and 75 units RNase inhibitor (Promega) in a volume of 100 μl. Another 200 units of reverse transcriptase were added and the reaction was continued for 30 minutes. The mixture was extracted with chloroform and precipitated with ethanol in the presence of 0.25M ammonium acetate. This mixture of first strand cDNAs was used as template in a subsequent Polymerase Chain Reaction (PCR) to amplify the amdS cDNA. The genomic amdS sequence was used to design 2 synthetic oligonucleotides that were used as primers in this PCR:

AB3100 (SEQ ID NO:1):

5'-CTAATCTAGAATGCCTCAATCCTGAA-3'

(an amdS-specific sequence from nucleotide −3 to +16 preceded by an XbaI site and 4 additional nucleotides).

AB3101 (SEQ ID NO:2):

5'-GACAGTCGACAGCTATGGAGTCACCACA-3'

(an amdS-specific sequence positioned downstream of the amdS stopcodon from nucleotides 1911 to 1884 flanked by an additional SalI site).

The PCR reaction was performed using 10% of the cDNA mixture as template and 0.1 μg of each of the oligos AB3100 (SEQ ID NO:1) and AB3101 (SEQ ID NO:2) as primer. After denaturation (7 minutes at 100° C.) and addition of 1.3 units s Taq-polymerase the reaction mixture was subjected to 25 amplification cycles (each cycle: 2 minutes at 94° C., 2 minutes at 55° C. and 3 minutes at 72° C.). In the last cycle the extension step was longer (7 min.) to allow synthesis of full-length fragments. The obtained DNA fragment was digested with XbaI and SalI and subcloned into the XbaI/SalI sites of pUC18. The resulting plasmid was designated pamdS-1 (see FIG. 1). Restriction analysis of the plasmid pamdS-1 confirmed the absence of introns and the correct fusion of exons in the amdS cDNA.

EXAMPLE 1

Marker Gene Free Deletion of an A. niger Gene by Using the amdS Gene

In this example a genomic target gene in A. niger will be replaced by transforming A. niger with a replacement vector which integrates into the A. niger genome via a double cross-over homologous recombination. The replacement vector comprises a DNA region homologous to the target locus interrupted by a selectable marker gene flanked by DNA repeats.

In this example plasmid pGBDEL4L is used to delete the glaA coding region and a (proximal) part of the glaA promoter region. This vector comprises a part of the A. niger glaA genomic locus, wherein the glaA coding sequences as well as a part of the glaA promoter sequences are replaced by the A. nidulans amdS gene under the control of A. nidulans gpdA promoter as selection marker flanked by 3'-untranslated glaA sequences as direct repeats. Transformation of A. niger with this vector directs replacement of the glaA gene by the amdS marker gene. By performing the fluoracetamide counter-selection on these transformants as described in the experimental procedures, the amdS marker gene will be deleted properly by an internal recombination event between the 3' glaA DNA repeats, resulting in a marker gene free ΔglaA recombinant strain, possessing finally no foreign DNA sequences at all (for a schematic view, see FIG. 2).

Short Description of the glaA Gene Replacement Vector pGBDEL4L

The gene replacement vector pGBDEL4L contains 5'-part of the A. niger amyloglucosidase (glaA) promoter region, a synthetic DNA sequence of 16 bp providing stopcodons in all three reading frames, the A. nidulans acetamidase (amdS) gene under control of the A. nidulans glyceraldehyde-3-phosphate dehydrogenase (gpdA) promoter, flanked at both sides by 3' glaA non-coding sequences.

Construction Pathway of pGBDEL4L

Figure 3A:
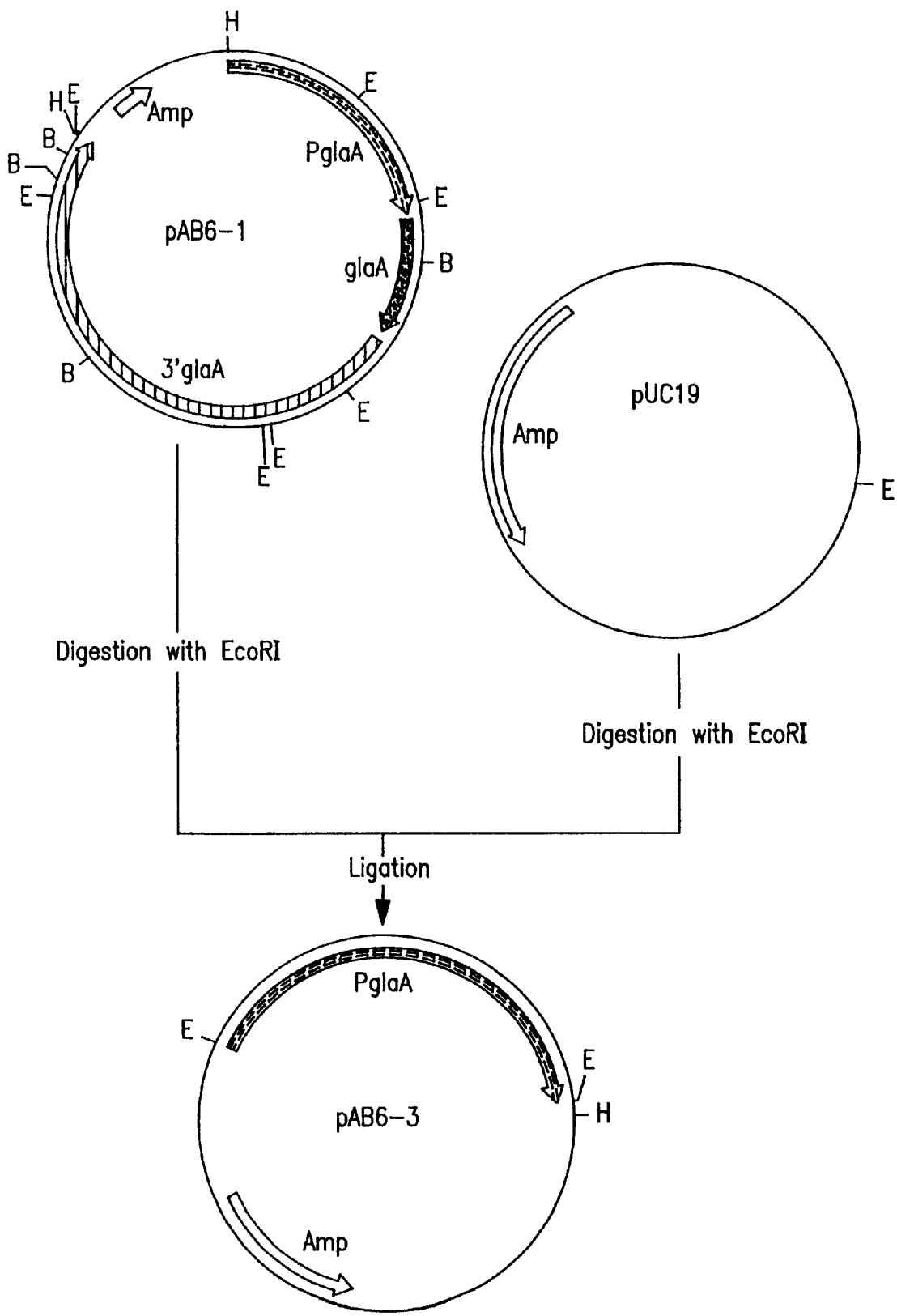
Figure 3B:
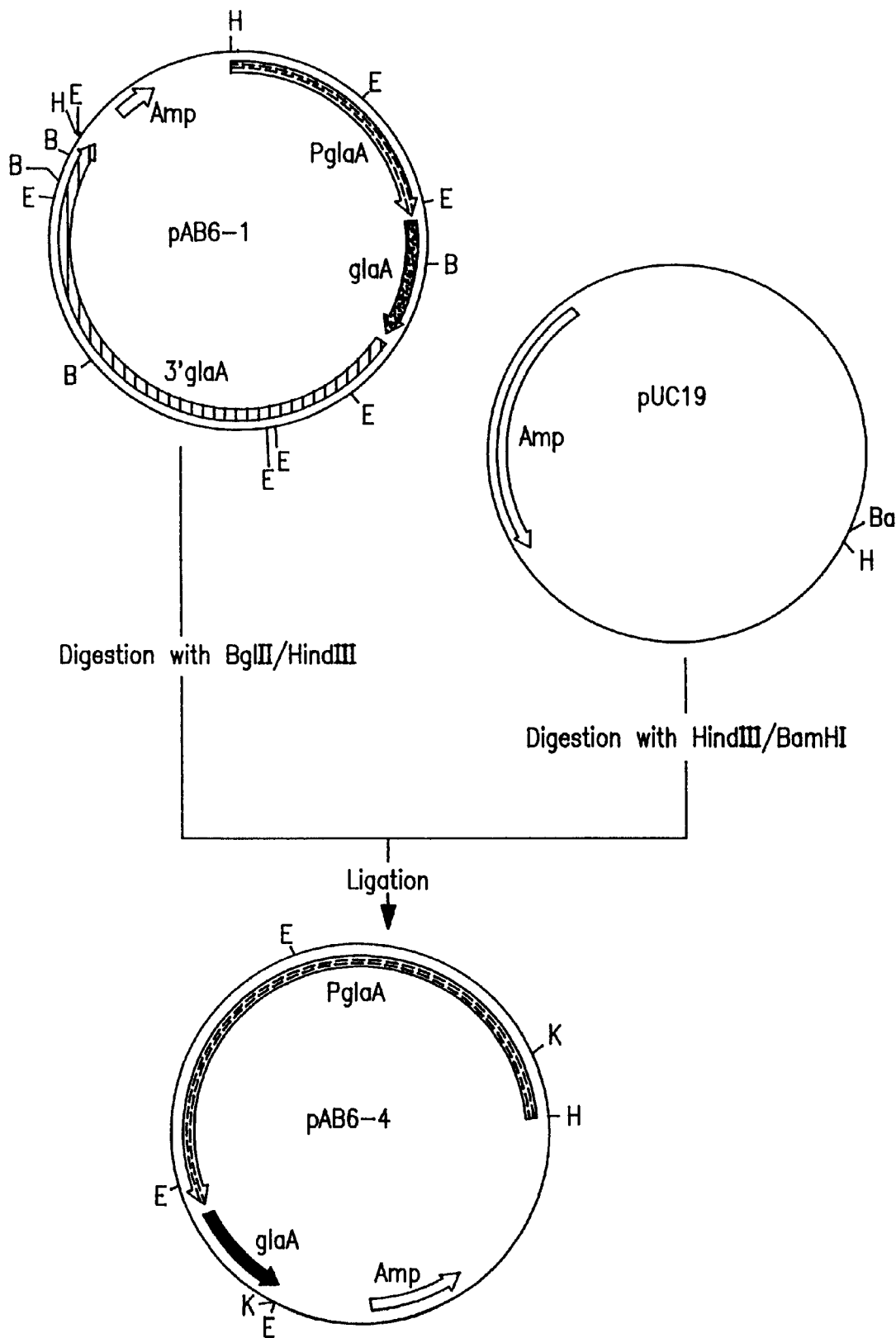

In order to obtain the final deletion vector pGBDEL4L several subclones of the glaA locus were derived first. A schematic view is presented in FIG. 3. The glaA locus of A. niger was molecular cloned and described previously (EP 0 463 706 A1). Plasmid pAB6-1 contains the entire glaA locus from A. niger on a 15.5 kb HindIII fragment cloned in the HindIII site of pUC19 (Yanisch-Perron et al., Gene 33 (1985) 103–119, and is obtainable from e.g. Boehringer Mannheim, Germany). pAB6-1 was digested with EcoRI and the 1.8 kb EcoRI DNA fragment just upstream of the glaA gene was isolated by agarose gel electrophoresis and ligated into pUC19 digested with EcoRI and subsequently transferred to E. coli and molecular cloned. The resulting plasmid was designated pAB6-3 (FIG. 3A). To construct plasmid pAB6-4, which is another subclone of pAB6-1, pAB6-1 was digested with HindIII and BglII. The 4.6 kb sized DNA fragment comprising the glaA promoter and a part of the glaA coding sequence was isolated by agarose gel electrophoresis and ligated into pUC19 which was digested prior with HindIII and BamHI (FIG. 3B). As a result the BamHI as well as the BglII sites in pAB6-4 were destroyed appropriately by this cloning procedure.

Figure 4:
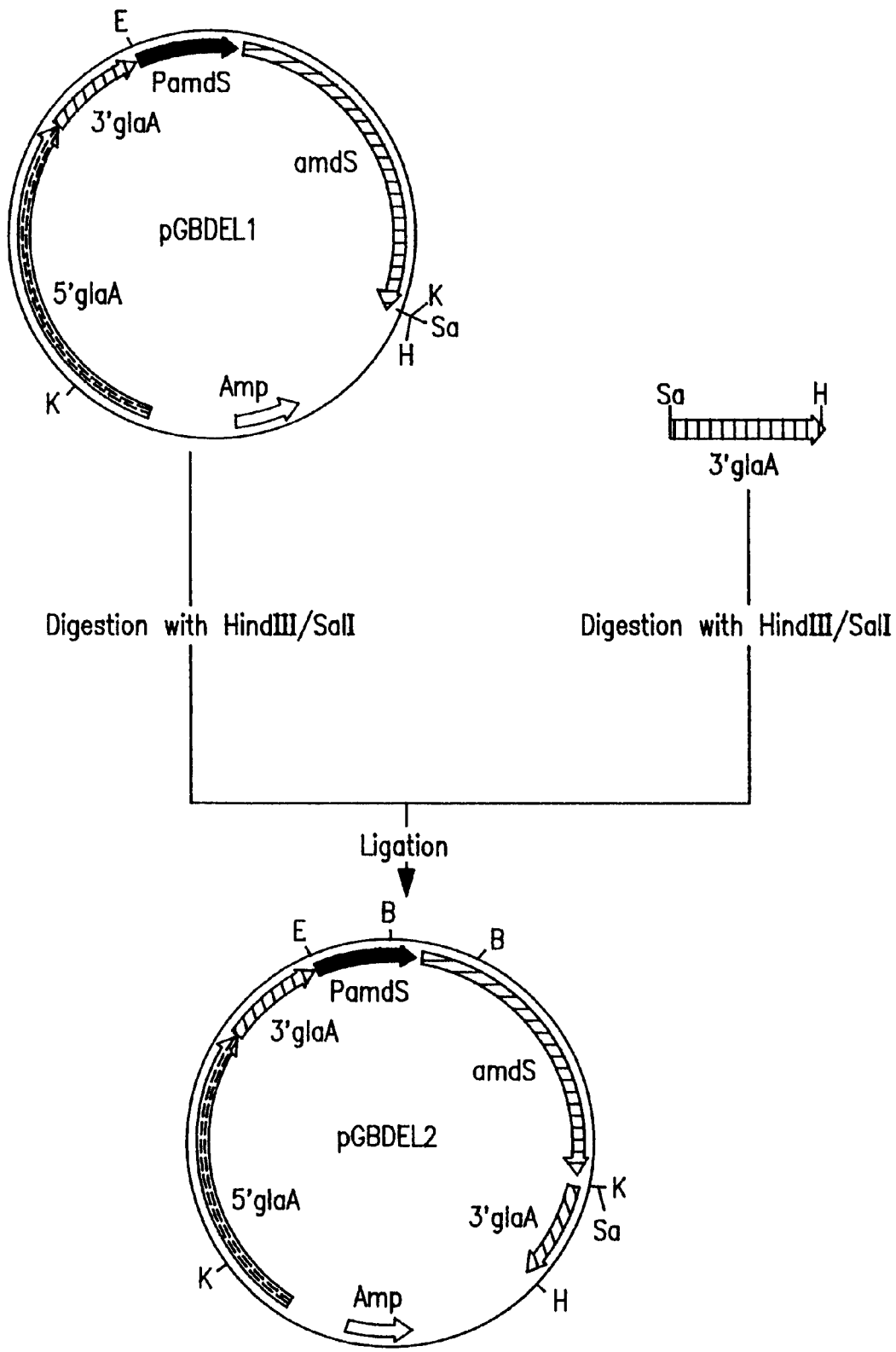
Figure 5:
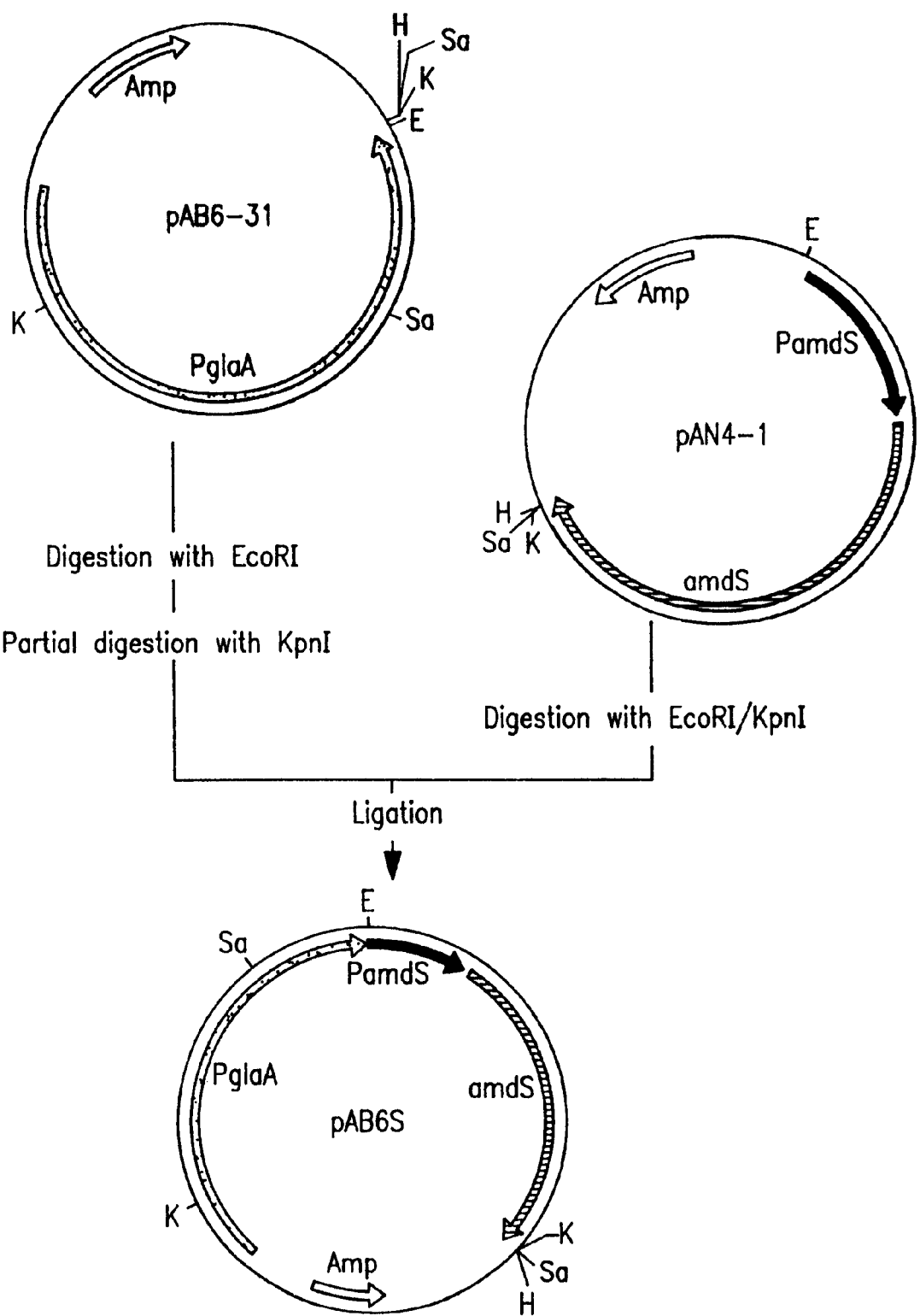

Subsequently, after digesting plasmid pAB6-4 with HindIII and EcoRI and filling in the 5' sticky ends using E. coli DNA polymerase, the 1.8 kb glaA promoter DNA fragment was isolated by agarose gel electrophoresis, ligated into pAB6-3 which was partially digested with EcoRI and treated with E. coli DNA polymerase to generate blunt ends, the ligation mixture was transferred to E. coli for molecular cloning. The derived plasmid (designated pAB6-31) contains a 3.6 kb glaA promoter fragment with a destroyed EcoRI site in the middle, but still possessing the EcoRI site (now unique in this DNA fragment) just upstream of the glaA ATG initiation site (FIG. 4).

The A. nidulans amdS gene used herein is located on an approximately 4 kb sized EcoRI-KpnI fragment in plasmid GW325 (Wernars et al., thesis (1986) Agricultural University, Wageningen, The Netherlands). This EcoRI-KpnI DNA fragment containing the amdS gene, flanked by its own regulatory sequences, was molecular cloned into the appropriate sites of pUC19 as described by Verdoes et al. (Transgenic Res. 2 pp 84–92, 1993) resulting in pAN4-1. pAN4-1 was digested with EcoRI and KpnI, the 4 kb sized DNA fragment containing the amdS gene was isolated by agarose gel electrophoresis, ligated into pAB6-31 digested with EcoRI and KpnI and the ligation mixture was transferred to E. coli for molecular cloning. The obtained plasmid was designated pAB6S (FIG. 5) and contains a 3.8 kb glaA promoter DNA fragment and the 4 kb amdS fragment.

Figure 6:
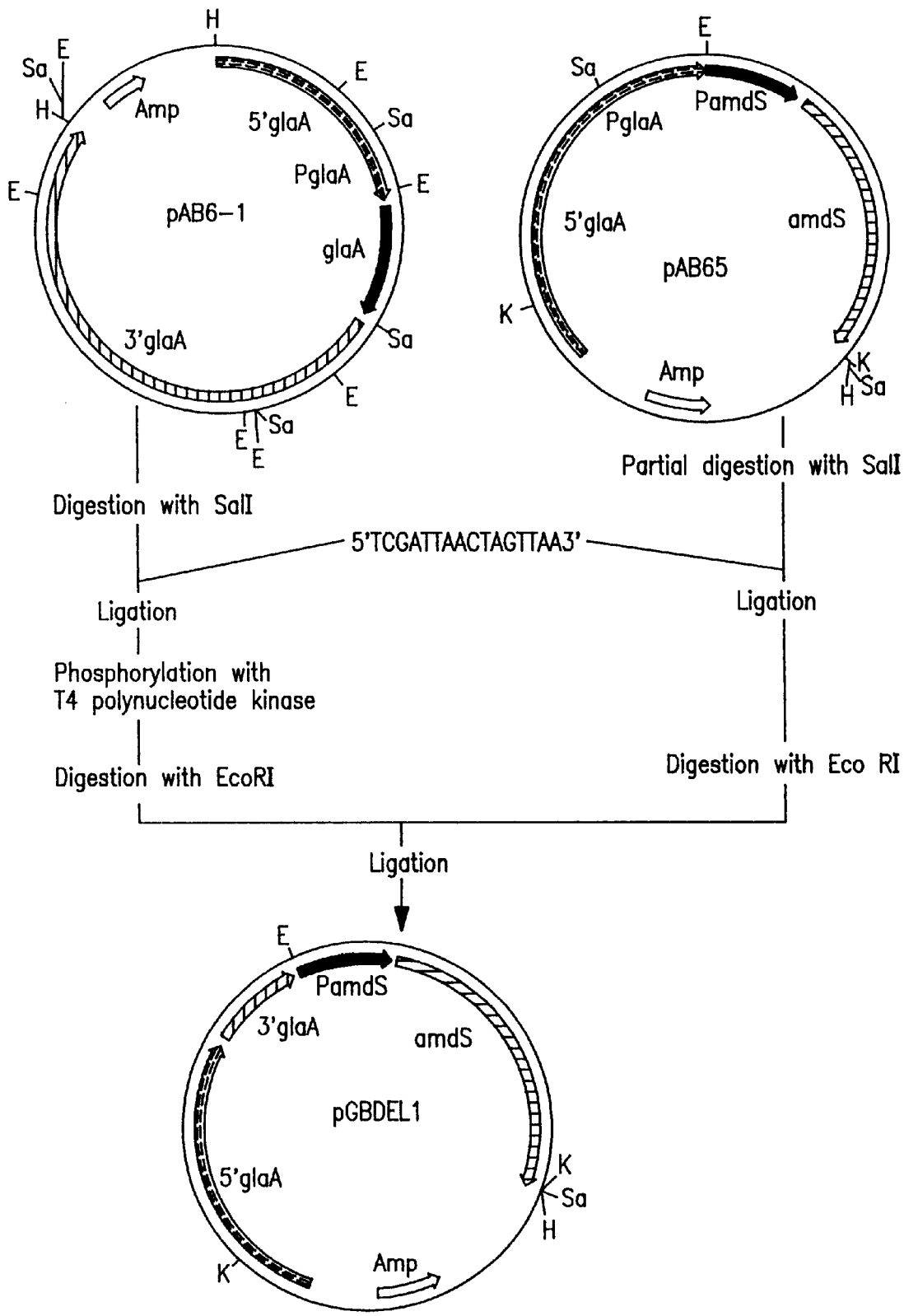

Plasmid pAB6S was first partially digested with SalI, and ligated to the synthetic derived oligonucleotide TN0001 (SEQ ID NO:3) having the following sequence:

TN0001 (SEQ ID NO:3):

5' TCGATTAACTAGTTAA 3' and secondly digested with EcoRI. The DNA fragment comprising the pUC19, the glaA promoter and the amdS gene sequences was purified and isolated by agarose gel electrophoresis. From plasmid pAB6-1, digested with SalI, the 2.2 kb 3' flanking glaA DNA fragment was isolated as well by agarose gel electrophoresis and ligated to the above mentioned synthetic oligonucleotide, treated with T4 polynucleotide kinase, subsequently digested with EcoRI and ligated to the above mentioned DNA fragment isolated of pAB6S. The DNA ligation mixture was transferred to E. coli and molecular cloned. The. derived plasmid was designated pGBDEL1 and is shown in FIG. 6. By this procedure simultaneously the SalI restriction site was destroyed and stopcodons in all reading frames were introduced.

To obtain an approximately 1 kb large DNA fragment, containing 3' glaA non-coding DNA sequences positioned just downstream the stop codon of the glaA gene and flanked by suitable restriction sites, a PCR amplification was performed. In this PCR amplification, the plasmid pAB6-1 was used as template and as primers two synthetical derived oligonucleotides:

Oligo AB2154 (SEQ ID NO:4):

5' AACCATAGGGTCGACTAGACAATCAATCCATTTCG 3'

(a 3' glaA non-coding sequence just downstream of the stopcodon) and

Oligo AB2155 (SEQ ID NO:5):

5' GCTATTCGAAAGCTTATTCATCCGGAGATCCTGAT 3'

(a 3' glaA non-coding sequence around the EcoRI site approx. 1 kb downstream of the stopcodon).

Figure 7B:
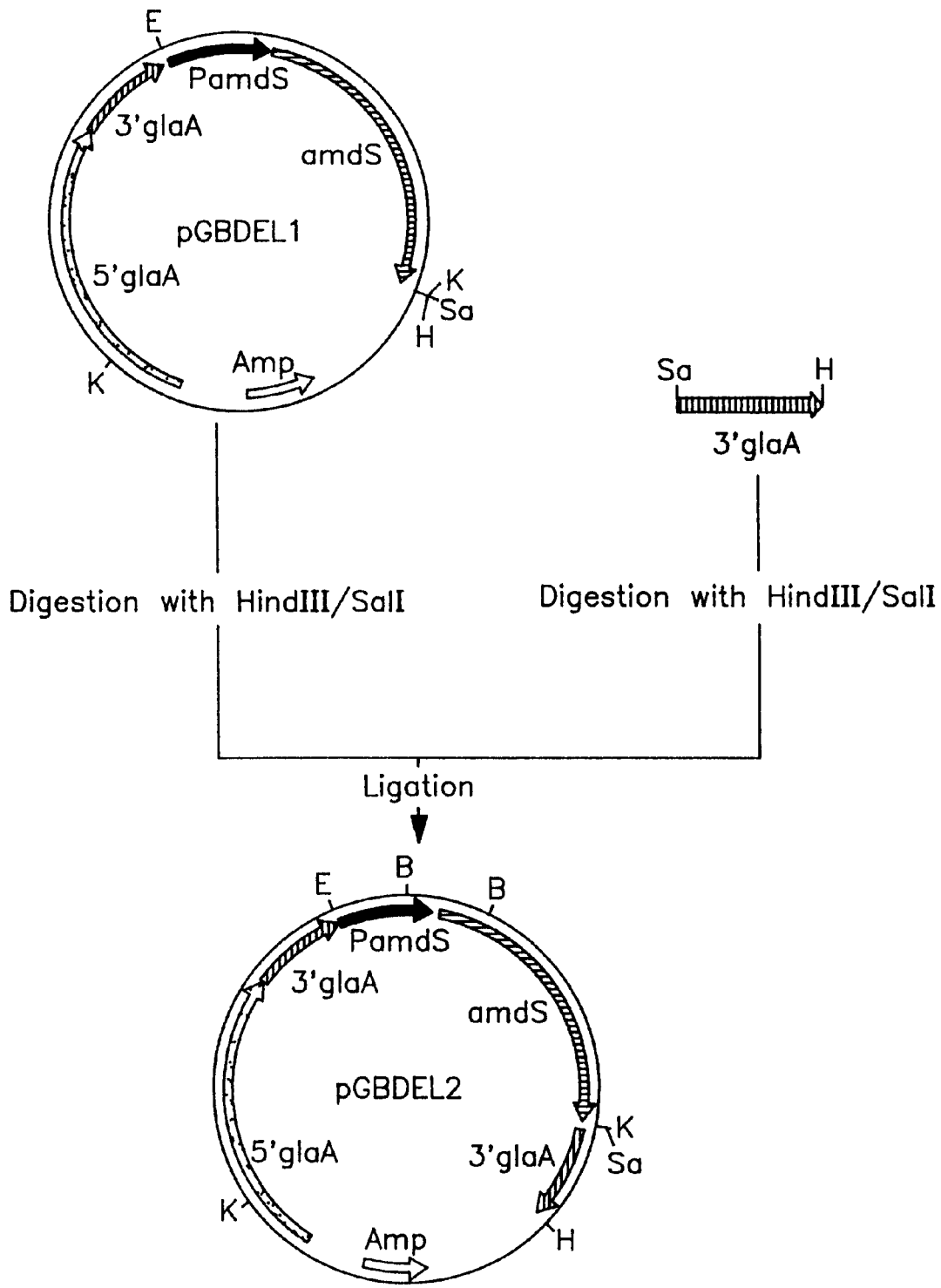

The PCR was performed as described by Saiki et al. (Science 239, 487–491, 1988) and according to the supplier of TAQ-polymerase (Cetus). Twenty five amplification cycles (each 2 minutes at 55° C.; 3 minutes at 72° C. and 2 minutes at 94° C.) were performed in a DNA-amplifier (Perkin-Elmer/Cetus). The 1 kb amplified DNA fragment was digested with HindIII and. SalI, purified by agarose gel electrophoresis, ethanol precipitated and subsequently cloned into the HindIII and. SalI restriction sites of pGBDEL1. The thus obtained plasmid was designated pGBDEL2 (FIGS. 7A,B).

To obtain the final glaA gene replacement vector pGBDEL4L, the amdS promoter region in pGBDEL2 was exchanged by the stronger A. nidulans gpdA promoter. Fusion of the gpdA promoter sequence to the coding sequence of the amdS gene was performed by the Polymerase Chain Reaction (PCR) method. For this PCR fusion two different templates were used: plasmid pAN7-1 (Punt et al., Gene 56, 117–124, 1987) containing the E. coli hph gene under control of the A. nidulans gpdA promoter and the A. nidulans trpC terminator and plasmid pAN4-1, containing the A. nidulans amdS gene under control of its own regulatory sequences. As primers four synthetic oligonucleotides were used, possessing the following sequences:

Oligo AB2977 (SEQ ID NO:6):

5' TATCAGGAATTCGAGCTCTGTACAGTGACC 3'

(a 5' gpdA promoter specific oligo nucleotide, positioned at approximately 880 bp upstream of the ATG startcodon of the E. coli hph gene)

Oligo AB2992 (SEQ ID NO:7):

5' GCTTGAGCAGACATCACCATGCCTCAATCCTGGGAA 3'

Oligo AB2993 (SEQ ID NO:8):

5' TTCCCAGGATTGAGGCATGGTGATGTCTGCTCAAGC 3'

(both sequences are complementary to each other and contain 18 bp of the 3' end of the gpdA promoter and 18 bp of the 5' part of the amdS coding region)

Oligo AB2994 (SEQ ID NO:9):

5' CTGATAGAATTCAGATCTGCAGCGGAGGCCTCTGTG 3'

(an amdS specific sequence around the BglII site approximately 175 bp downstream of the ATG initiation codon)

Figure 8A:
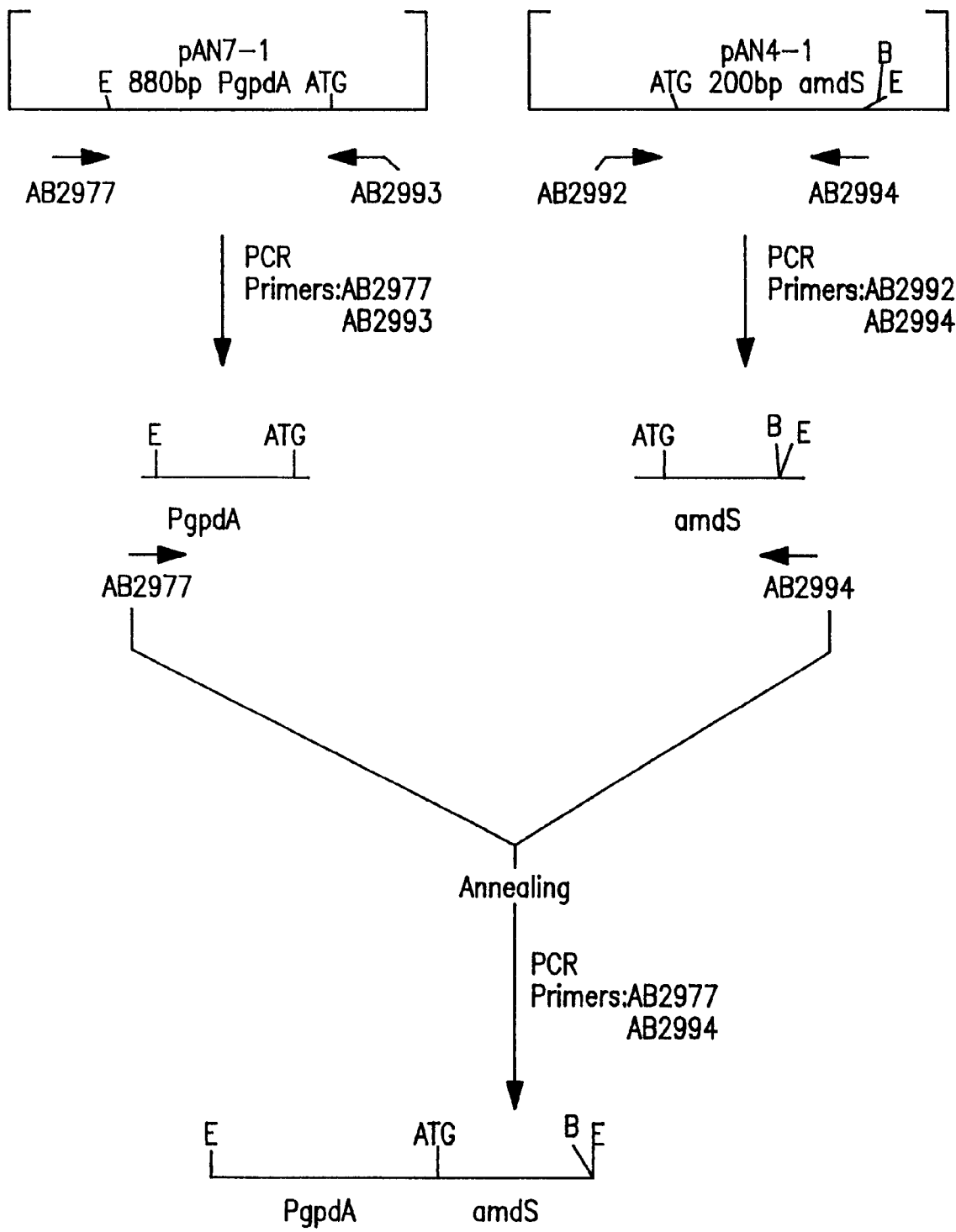
Figure 8B:
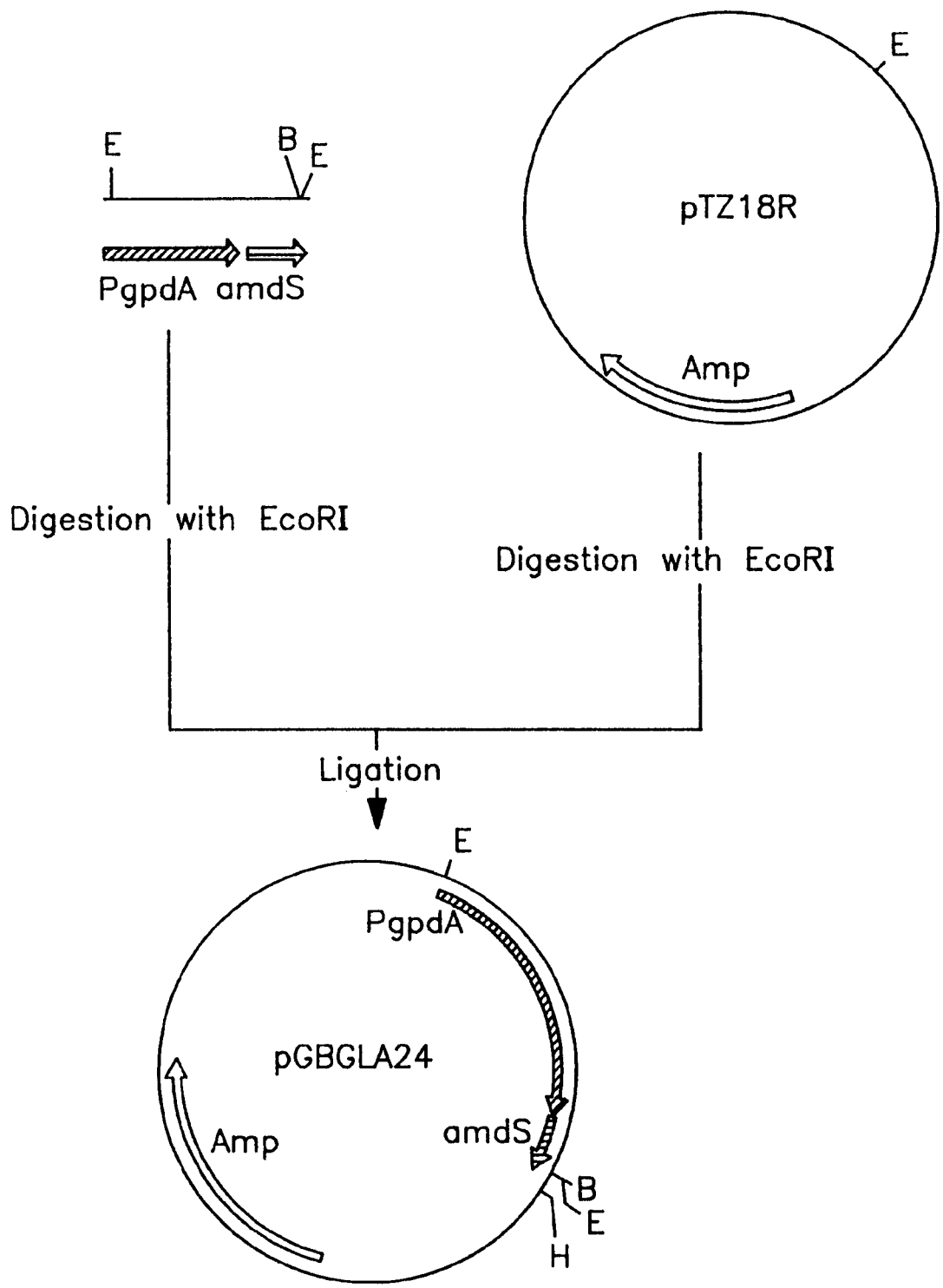

To fuse the 880 bp gpdA promoter region to the amdS coding sequence two separate PCR's were carried out: the first amplification with pAN7-1 as template and the oligo nucleotides AB 2977 (SEQ ID NO:6) and AB2993 (SEQ ID NO:8) as primers to amplify the 880 bp DNA fragment comprising the gpdA promoter flanked at the 3' border by 18 nucleotides complementary to the 5' end of the amdS gene, and the second PCR reaction with pAN4-1 as template and the oligo nucleotides AB2992 (SEQ ID NO:7) and AB2994 (SEQ ID NO:9) as primers to amplify a 200 bp sized DNA fragment comprising the 5' part of the amdS gene flanked at the 5' border by 18 nucleotides complementary to the 3' end of the gpdA promoter. A schematic view of these amplifications is presented in FIG. 8A. The two fragments generated were subsequently purified by agarose gel electrophoresis, ethanol precipitated and used as templates in a third PCR reaction with oligo nucleotides AB 2977 (SEQ ID NO:6) and AB2994 (SEQ ID NO:9) as primers. The resulting DNA fragment was digested with EcoRI, purified by agarose gel electrophoresis and ethanol precipitation, and cloned into the EcoRI site of pTZ18R (United States Biochemicals). The resulting plasmid was designated pGBGLA24 (FIG. 8B).

Figure 9:
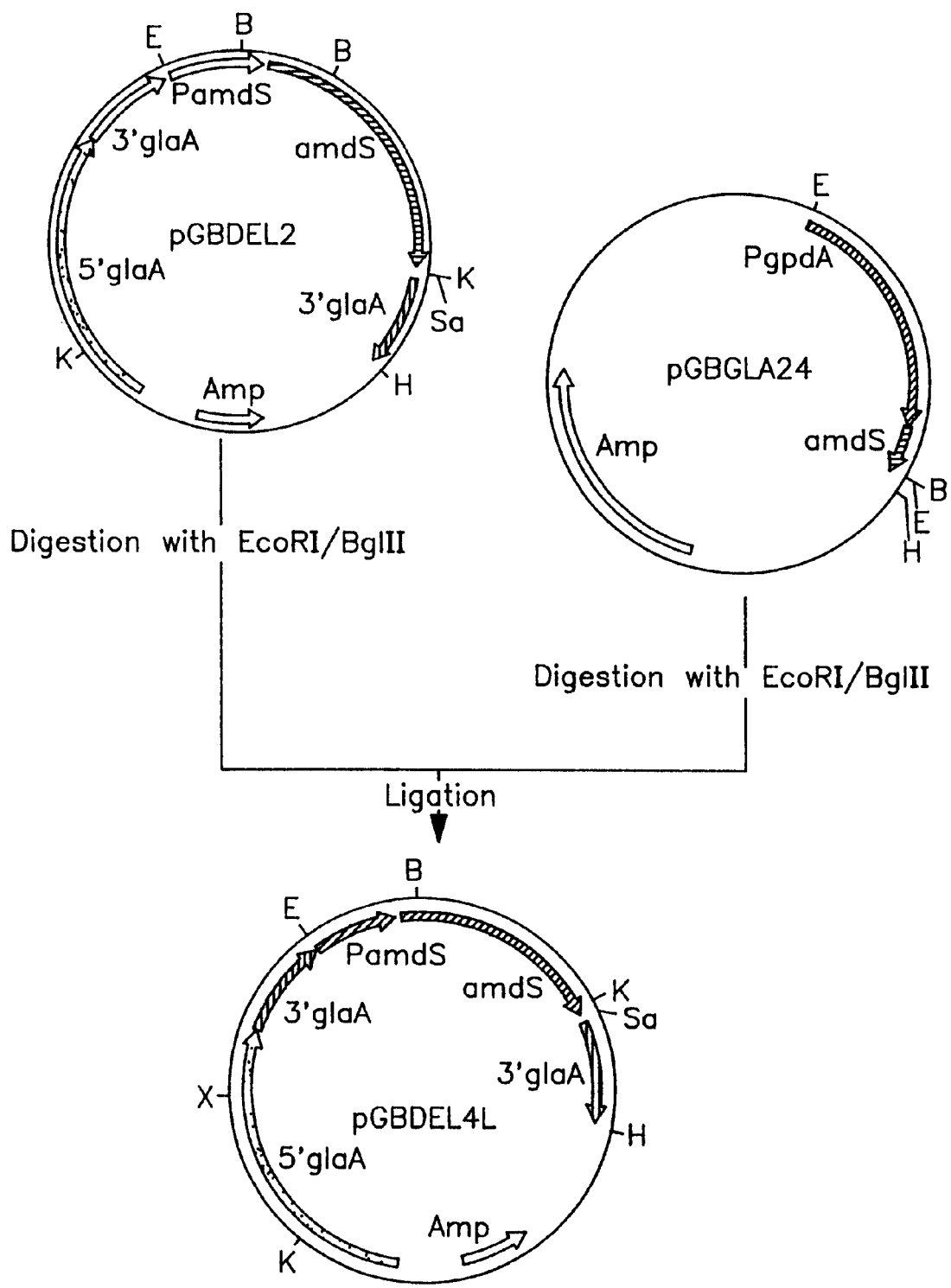

To exchange the amdS promoter sequence in pGBDEL2 by the gpdA promoter sequence, the approximately 1 kb sized, EcoRI/BglII DNA fragment of pGBGLA24 was isolated by agarose gel electrophoresis after digestion with the appropriate restriction enzymes and ligated into the EcoRI and BglII sites of pGBDEL2. The resulting glaA gene replacement vector was designated pGBDEL4L (FIG. 9).

Deletion of glaA Promoter and Coding Sequences in *A. niger*

Prior to transformation of *A. niger* with pGBDEL4L, the *E. coli* sequences were removed by HindIII and XhoI digestion and agarose gel electrophoresis. The *A. niger* strain CBS 513.88 (deposited October 10, 1988) was transformed with either 2.5, 5 or 10 μg DNA fragment by procedures as described in experimental procedures using acetamide as sole N-source in selective plates. Single *A. niger* transformants were purified several times onto selective acetamide containing minimal plates. Spores of individual transformants were collected by growing for about 5 days at 30° C. on 0.4% potato-dextrose (Oxoid, England) agar plates. Southern analyses were performed to verify the presence of the truncated glaA locus. High molecular weight DNA of several transformants was isolated, digested with BamHI and KpnI and subsequently fractionated by electrophoresis on a 0.7% agarose gel. After transfer to nitrocellulose filters, hybridization was performed according to standard procedures using two $^{32}$P-labelled probes: a XhoI/SalI glaA promoter fragment isolated from plasmid pAB6-4 (described above, FIG. 3A) and a probe recognizing endogenous xylanase sequences (European Patent Application. 0 463 706 A). The results of only 4 transformants (#19, #23, #24, #41) and the control strain *A. niger* CBS 531.88 are shown as examples in FIG. 10A. For a better understanding of this autoradiograph, a schematic presentation is presented in FIG. 11 showing the size of the hybridizing fragments in intact and truncated glaA loci.

Figure 10A:
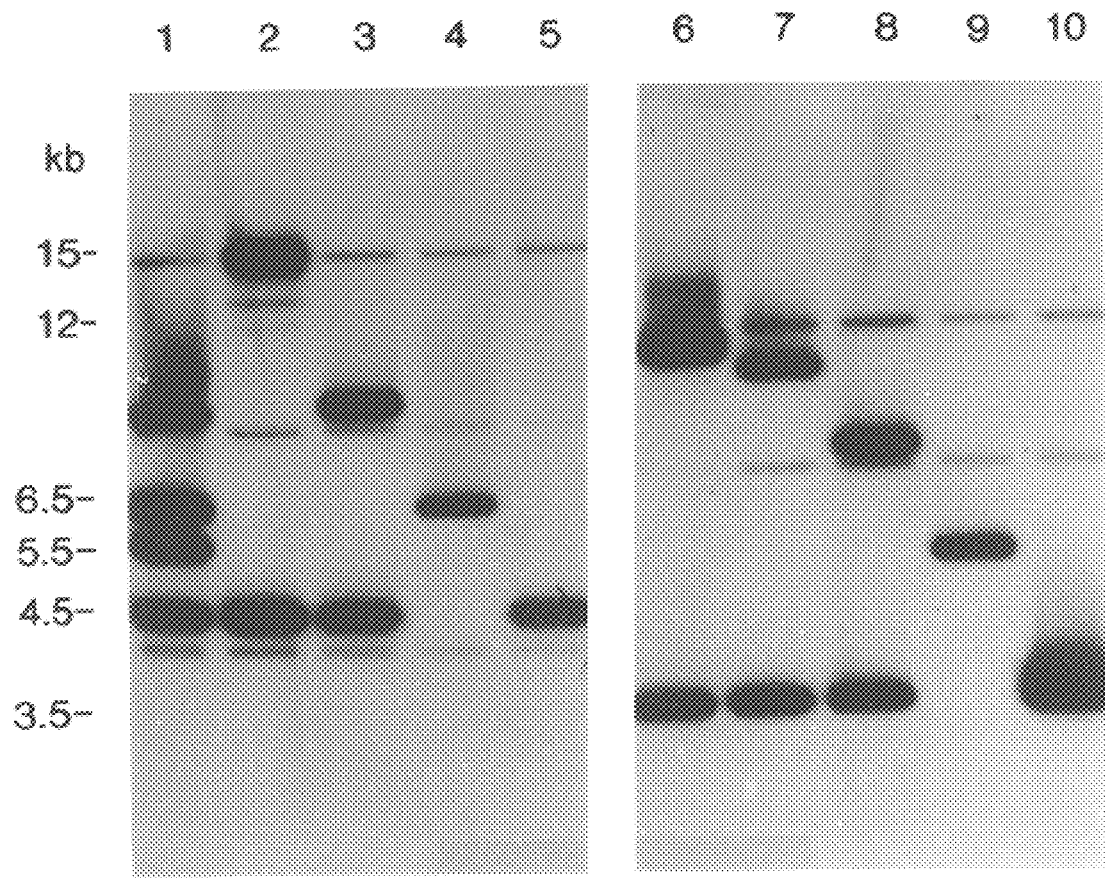

Characteristic for the intact glaA locus is a 3.5 kb hybridizing fragment in a BamHI digest and a 4.5 kb hybridizing fragment in a KpnI digest (see FIG. 11A). In a truncated glaA locus, the 3.5 kb BamHI hybridizing fragment and the 4.5 kb KpnI hybridizing fragment are absent and replaced by a 5.5 kb BamHI hybridizing fragment and a 6.3 kb KpnI hybridizing fragment. In this example, as can be seen in FIG. 10A, transformant #19 shows the expected pattern of a truncated glaA locus (FIG. 11B). This transformant was designated GBA-102.

No replacement of the glaA gene had occurred in the other transformants. The poorly hybridizing bands: 4, 8 and 15 kb in the KpnI digest and 7 and 12 kb in the BamHI digest, refer to the xylanase sequences as internal control.

Figure 10B:
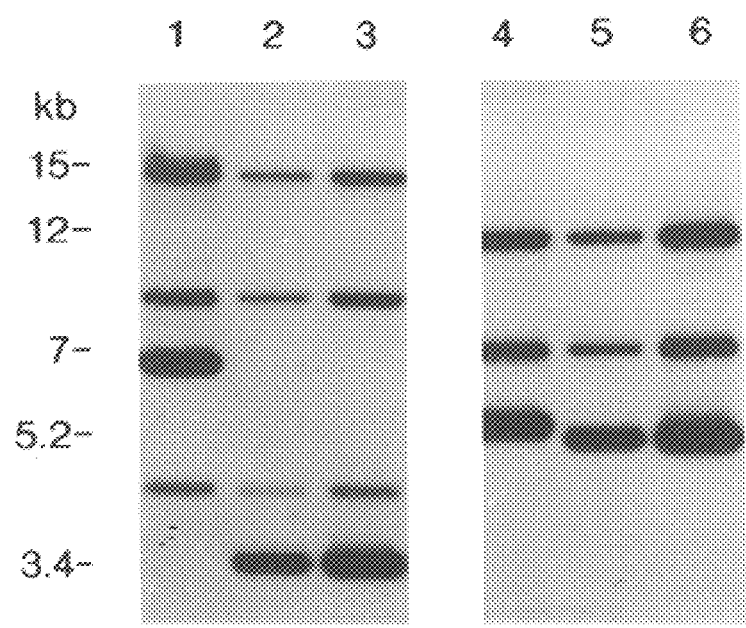
Figure 11C:
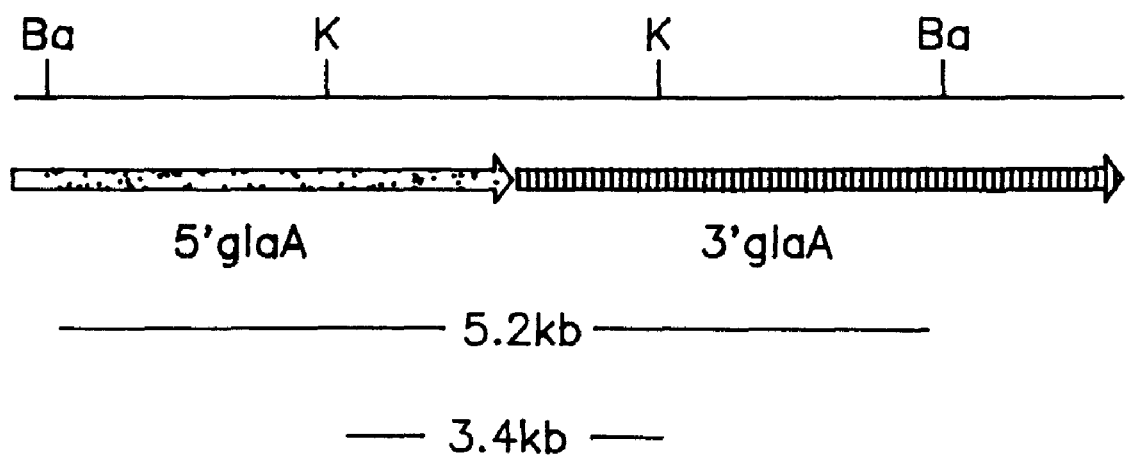

Removal of the amdS Gene from *A. niger* GBA-102 by Counter-Selection on Fluoracetamide Containing Plates The amdS gene in the transformant *A. niger* GBA-102 was removed again as described in the Experimental section. The removal of the amdS selection marker gene in only 2 surviving recombinant strains was verified by Southern analysis of the chromosomal DNA. High molecular weight DNA was isolated, digested with BamHI and KpnI and subsequently separated by electrophoresis on a 0.7% agarose gel. Following transfer to nitrocellulose hybridization was performed according to standard procedures using the probes described in the previous section. A schematic presentation of the hybridizing fragments is shown in FIG. 11C. The results of the Southern analyses are presented in FIG. 10B. The presence of a 5.2 kb hybridizing BamHI fragment and a 3.4 kb hybridizing KpnI fragment, with the concomitant loss of the 5.5 kb BamHI and the 6.3 kb hybridizing KpnI fragments is specific for the absence of the amdS selection marker. The weaker hybridizing 7 and 12 kb fragments in a BamHI digest and the 4, 8 and 15 kb KpnI fragments again refer to the endogenous xylanase locus. Both strains show the expected pattern. In these recombinant strains, which were designated GBA-107 and GBA-108, the preferred glaA sequences are removed correctly and that possess finally no selection marker gene at all. Both strains can be reused again to delete or insert other genes or DNA elements by using the same type of vector.

EXAMPLE 2

Marker Gene Free Introduction of the glaA Gene Targeted at the 3'glaA Non-Coding Region of the Truncated glaA Locus in *A. niger* GBA-107

Figure 12A:
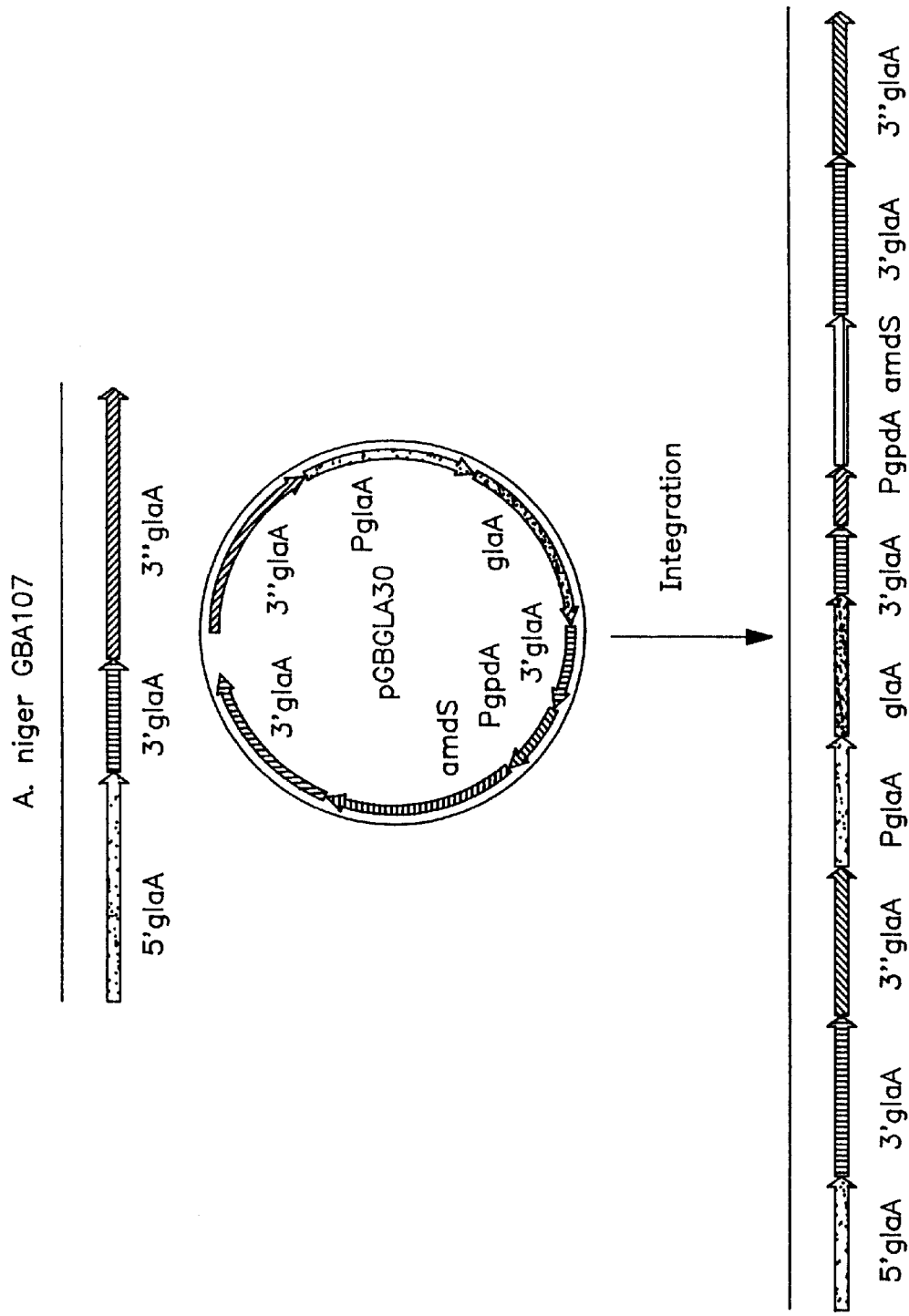
Figure 12B:
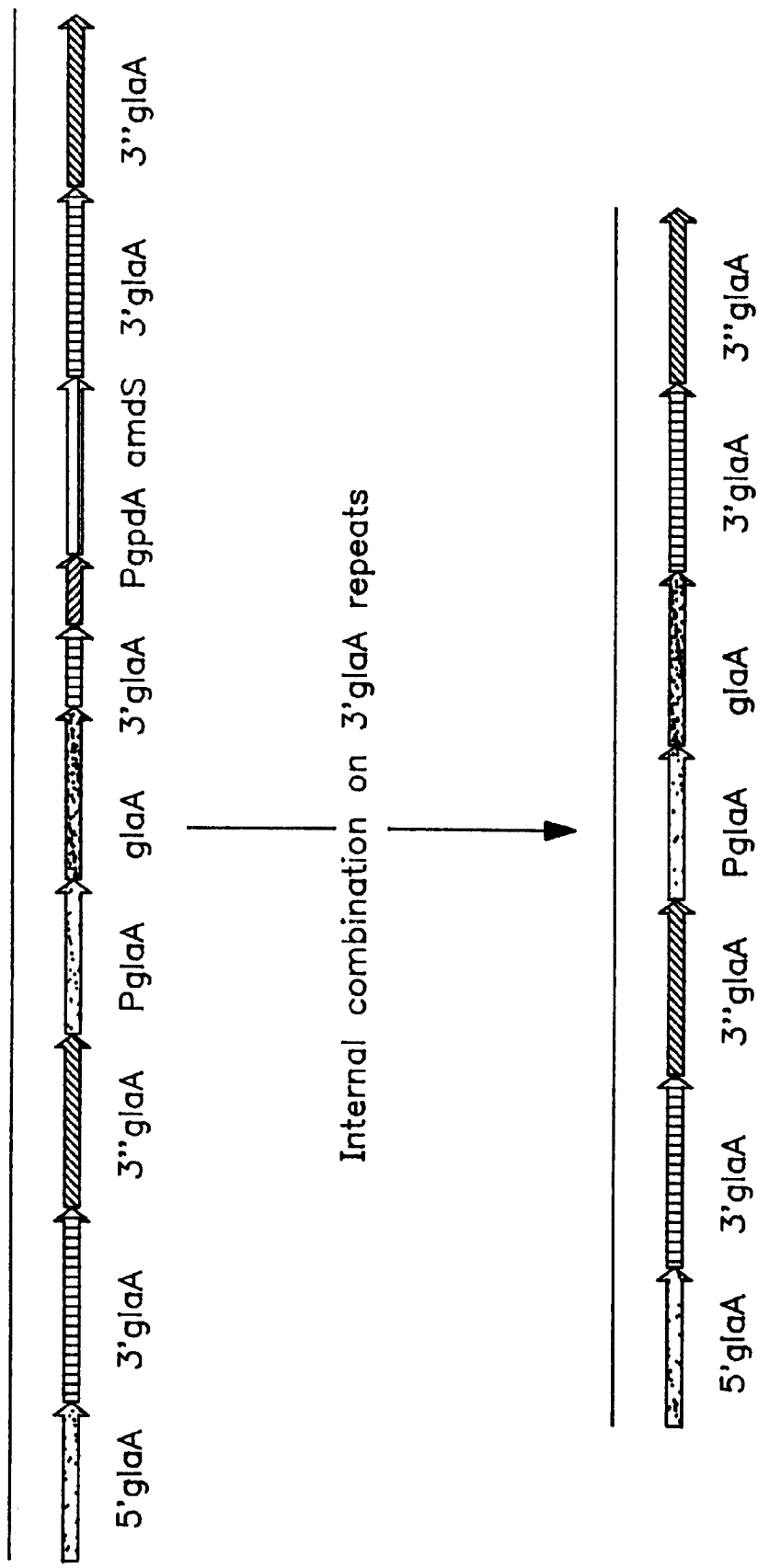

In this example the introduction of a gene into the genome of *A. niger* is described by using approximately the same approach and procedures as described in the previous example. Besides the desired gene or DNA element the vector contains DNA sequences homologous to the host genome to target the vector at a predefined genomic locus of the host, by a single cross-over event. This type of vector comprises a selection marker gene flanked by DNA repeats as well. The selection marker gene in transformants derived with this vector can be removed properly again by applying the counter-selection procedure. As an example the introduction of a glaA gene copy is described which becomes integrated at the truncated glaA locus in the recombinant ΔglaA *A. niger* GBA-107 strain derived in Example I (for a schematic drawing see FIG. 12).

Description of the glaA Integration Vector: pGBGLA30

The integration vector pGBGLA30 consists of the *A. niger* amyloglucosidase (glaA) gene under control of the native promoter and the *A. nidulans* amdS gene under control of the *A. nidulans* gpdA promoter flanked by 3' glaA non-coding sequences to direct integration at the 3' glaA non-coding region and to remove the amdS selection marker gene via the counter-selection.

Construction of the Integration Vector

Figure 13:
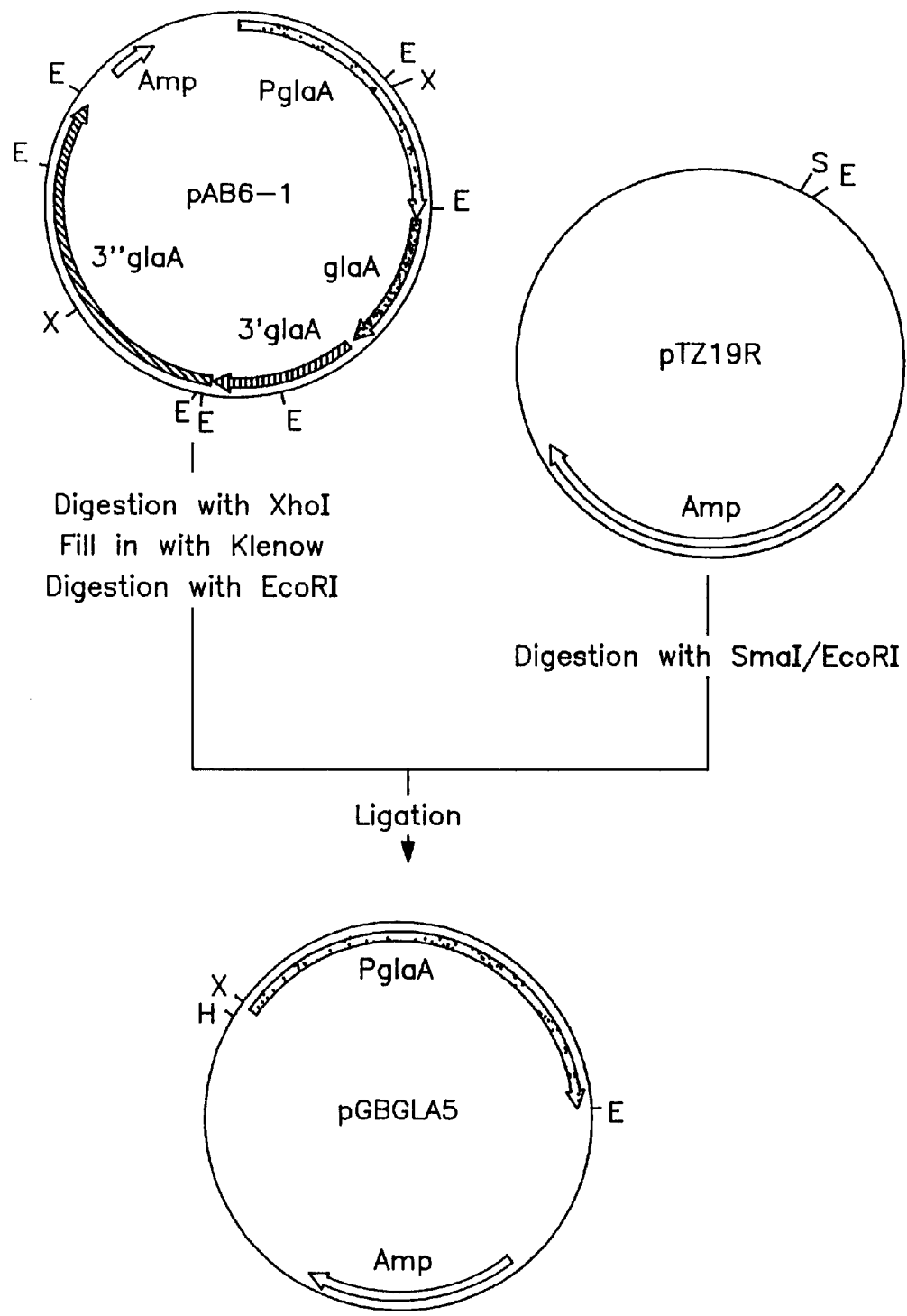

A 1.8 kb XhoI/EcoRI promoter fragment from pAB6-1 (FIG. 13) was subcloned into the SmaI and EcoRI sites of pTZ19R (United States Biochemicals). The protruding 5' end of the XhoI site of the glaA promoter fragment was filled in is using the Klenow fragment of *E. coli* DNA polymerase I prior to cloning in pTZ19R. The SmaI site is destroyed and the XhoI site is restored by this cloning procedure. The thus obtained plasmid was designated pGBGLA5 (FIG. 13).

Figure 14:
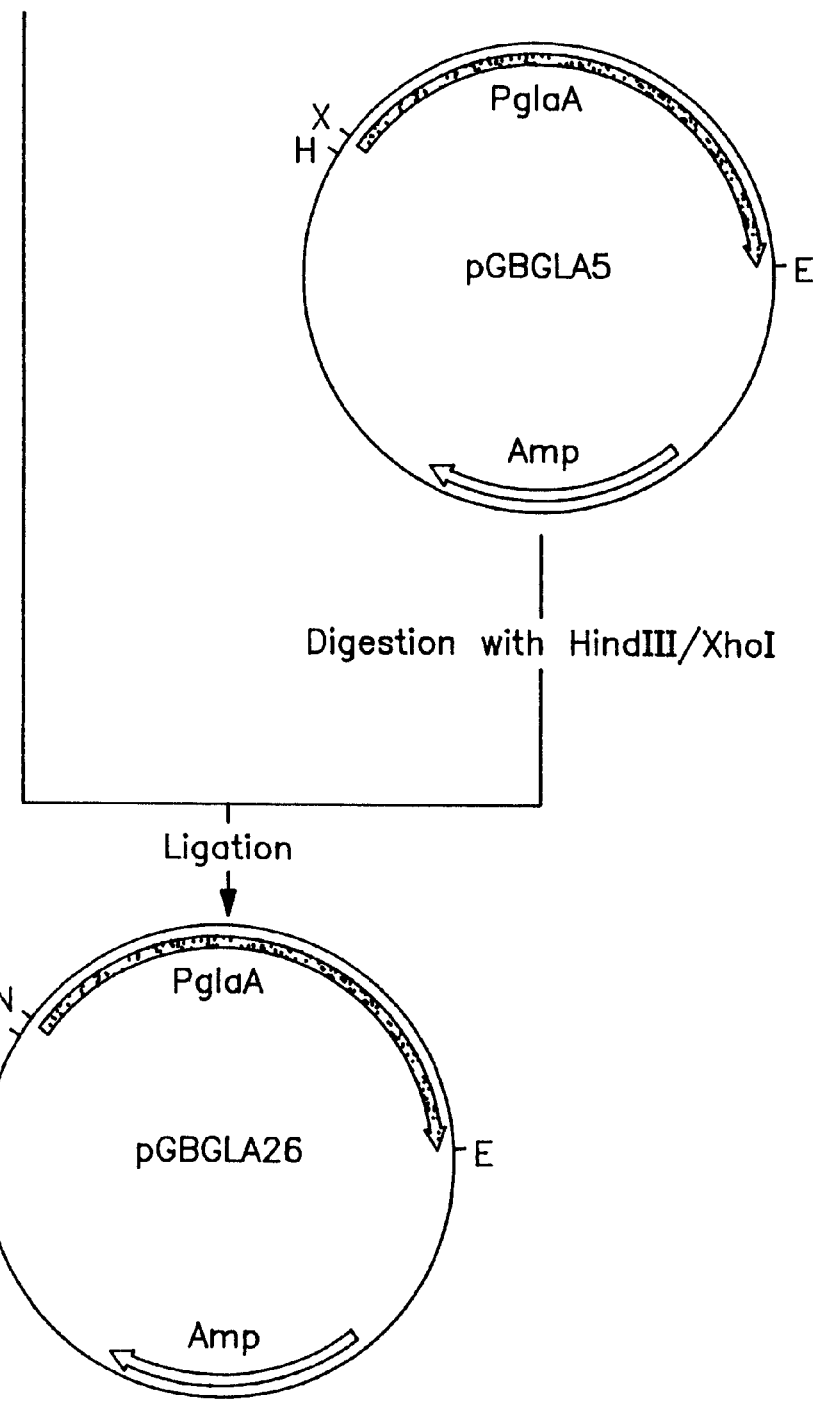

To introduce appropriate restriction sites (AatII, SnaBI, AsnI and NotI) and to destroy the XhoI site in the glaA promoter, the synthetic fragment consisting of the two oligonucleotides AB3657 (SEQ ID NO:10) and AB3658 (SEQ ID NO:11):

was inserted into the HindIII and XhoI sites of pGBGLA5. The thus obtained plasmid was designated pGBGLA26 (FIG. 14).

Figure 15:
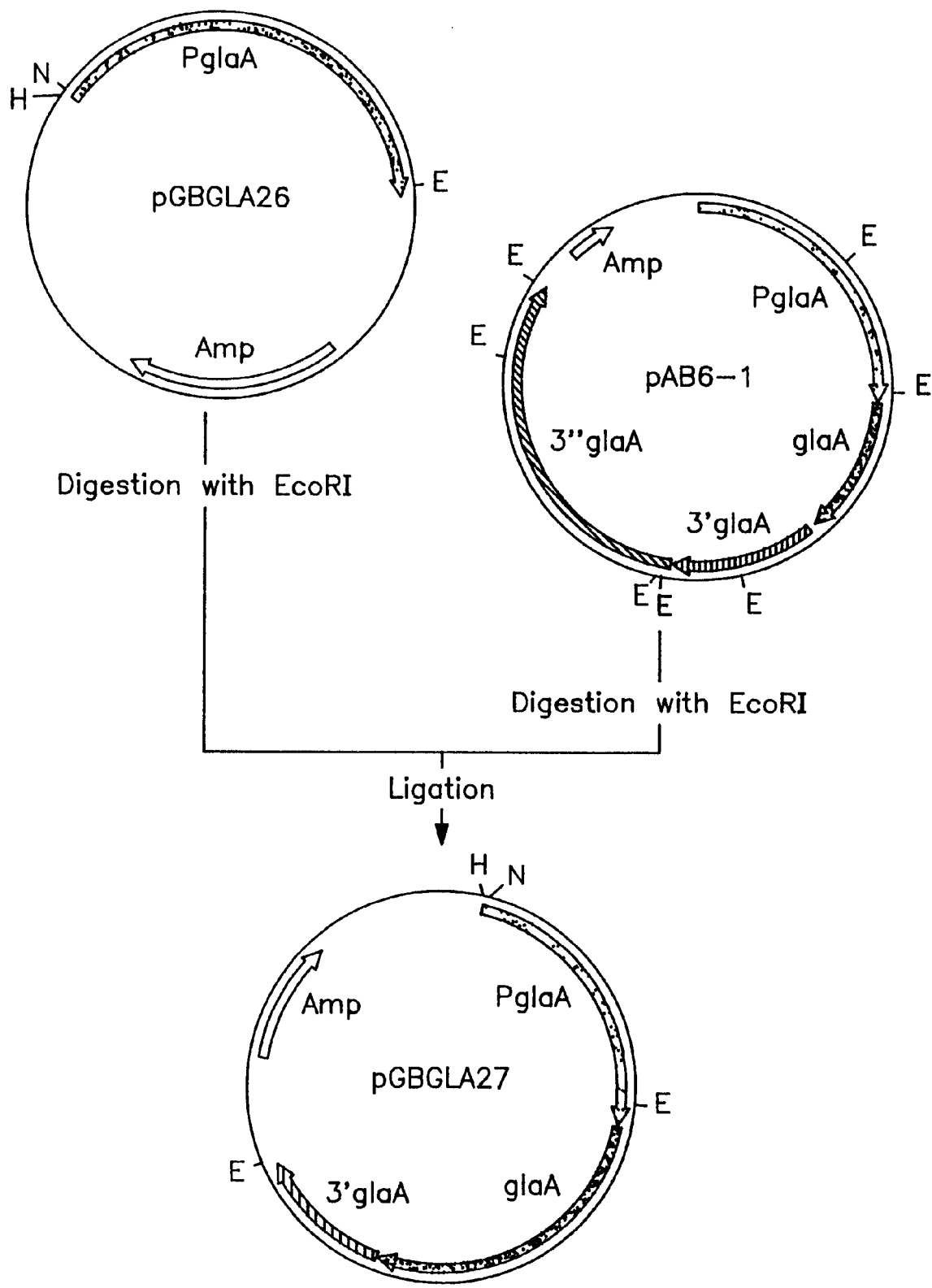

Next, the 3.4 kb EcoRI fragment from pAB6-1 containing the remaining 3' part of the glaA promoter, the glaA coding sequence and part of the 3' glaA non-coding sequence, was cloned into the EcoRI site of pGBGLA26. This new plasmid was designated pGBGLA27 (FIG. 15). This plasmid was partially digested with EcoRI and the synthetic fragment consisting of the oligonucleotides AB3779 (SEQ ID NO:12) and AB3780 (SEQ ID NO:13): 1

Figure 16:
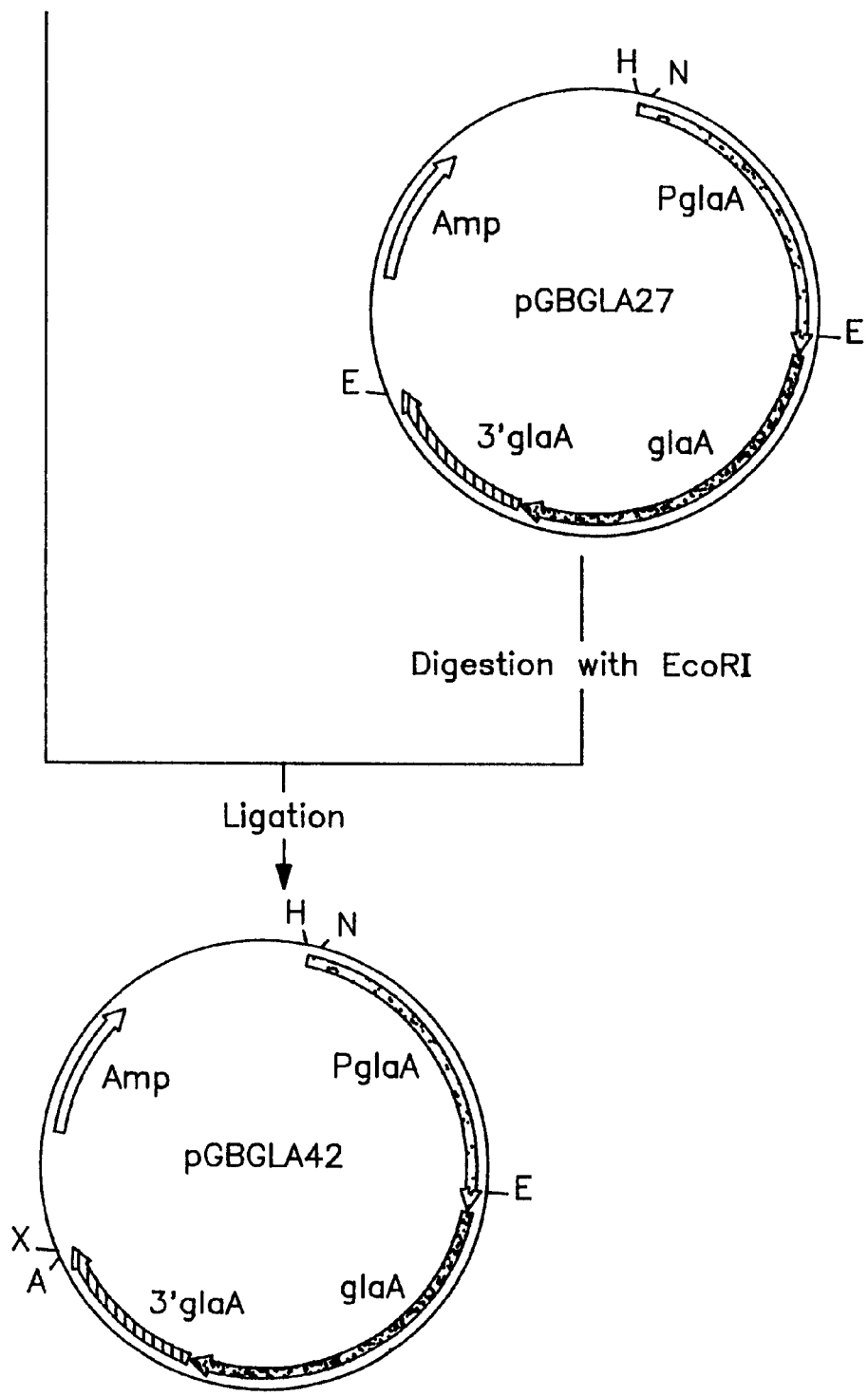

was inserted into the EcoRI site at the end of the 3' glaA non-coding sequence from the glaA gene. By this cloning step, the EcoRI site was destroyed and an ApaI and XhoI restriction site were introduced. The resultant plasmid was designated pGBGLA42 (FIG. 16).

Amplification of the 2.2 kb 3' glaA non-coding sequences and concomitant adjustment of appropriate restriction sites was performed by the Polymerase Chain Reaction (PCR) method.

In these PCR reactions, plasmid pAB6-1 containing the entire glaA locus was used as template and as primers four synthetic oligo nucleotides were designed possessing the following sequence:

Oligo AB3448 (SEQ ID NO:14):

(a 3' glaA non-coding specific sequence just downstream the stopcodon of the glaA gene)

Oligo AB3449 (SEQ ID NO:15):

(a 3' glaA non-coding specific sequence around the KpnI site approx. 1 kb downstream of the stop codon)

Oligo AB3450 (SEQ ID NO:16):

(a 3' glaA non-coding specific sequence around the KpnI site approx. 1 kb downstream of the stop codon)

Oligo AB3520 (SEQ ID NO:17):

(a 3' glaA non-coding specific sequence approx. 2.2 kb downstream of the stopcodon)

To destroy the KpnI site approximately 1 kb downstream of the stop codon from the glaA gene and to alter the SalI site approximately 2.2 kb downstream the stop codon from the glaA gene into a XhoI site two separate polymerase chain reactions were performed: the first reaction with oligonucleotides AB3448 (SEQ ID NO:14) and AB3449 (SEQ ID NO:15) as primers to amplify an approximately 1 kb DNA fragment just downstream the stopcodon of the glaA gene, and the second reaction with oligonucleotides AB3450 (SEQ ID NO:16) and AB3520 (SEQ ID NO:17) as primers to amplify an approximately 1.2 kb DNA fragment just downstream the KpnI site in the 3' glaA non-coding region both with pAB6-1 as template. A schematic view of these amplifications is presented in FIG. 17A. The PCR was performed as described in example I. Twenty-five amplification cycles (each 1 minute at 55° C.; 1.5 minutes at 72° C. and 1 minute at 94° C.) were carried out.

Figure 17A:
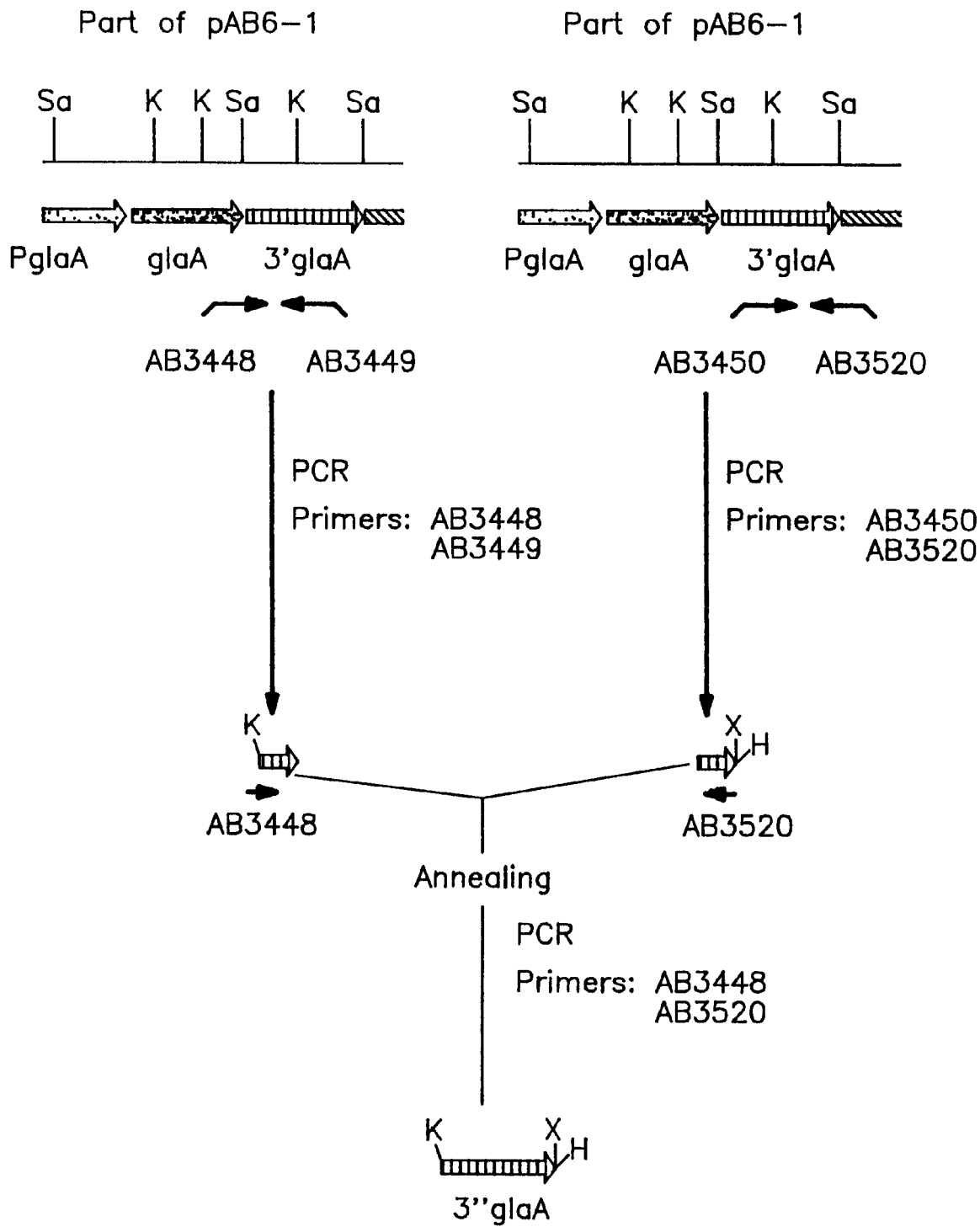
Figure 17B:
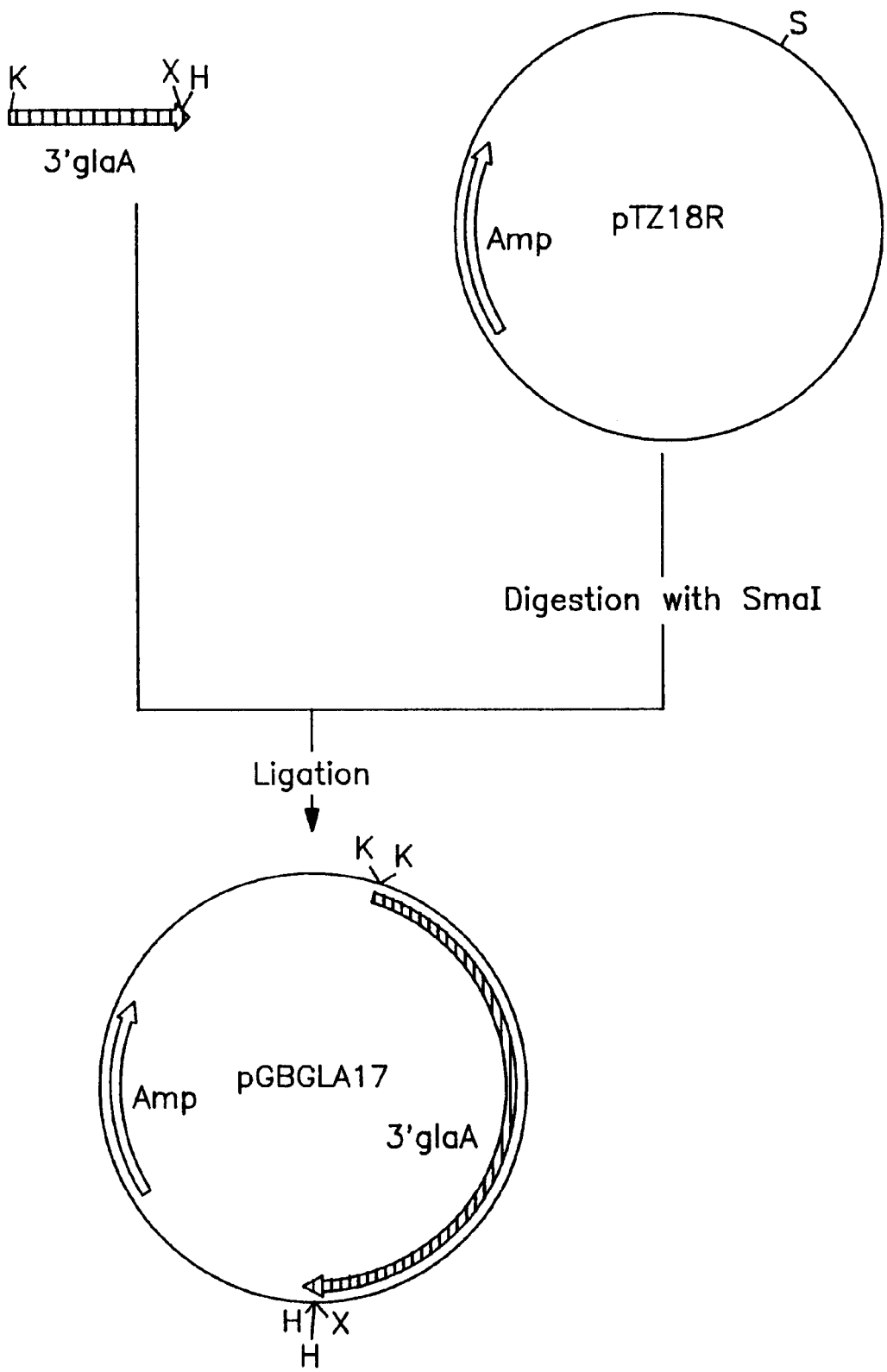

The two generated PCR DNA fragments were purified by agarose gel electrophoresis and ethanol precipitation and subsequently used as template in the third PCR with oligonucleotides AB3448 (SEQ ID NO:14) and AB3520 (SEQ ID NO:17) as primers to generate the fusion fragment. Twenty-five amplification cycles (each: 2 minutes at 55° C.; 3 minutes at 72° C.; 2 minutes at 94° C.) were carried out in a DNA-amplifier (Perkin-Elmer/Cetus). The amplified DNA fragment was purified by agarose gel electrophoresis and ethanol precipitation and subsequently subcloned in the SmaI site of pTZ18R. The obtained plasmid was designated pGBGLA17 (FIG. 17B).

Figure 18:
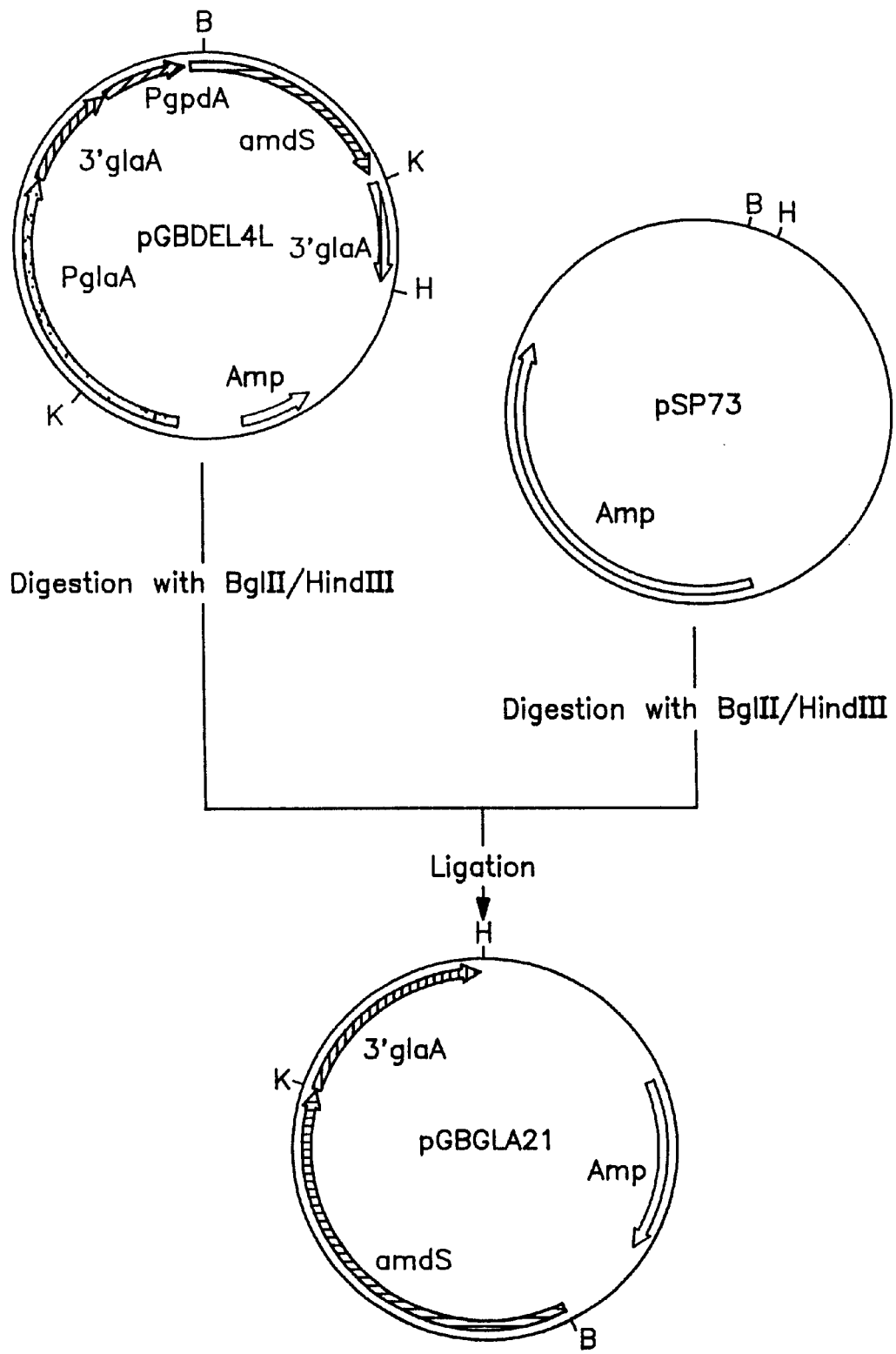

To fuse this adjusted 3' glaA non-coding region to the amdS gene, a part of the amdS gene was subcloned from pGBDEL4L into pSP73 (Promega). For this construction, pGBDEL4L was digested with BglII and HindIII, the 3.4 kb amdS/3' glaA non-coding fragment was isolated by agarose gel electrophoresis and subcloned into the appropriate sites of pSP73 (Promega). The resulting plasmid was designated pGBGLA21 (FIG. 18).

Figure 19:
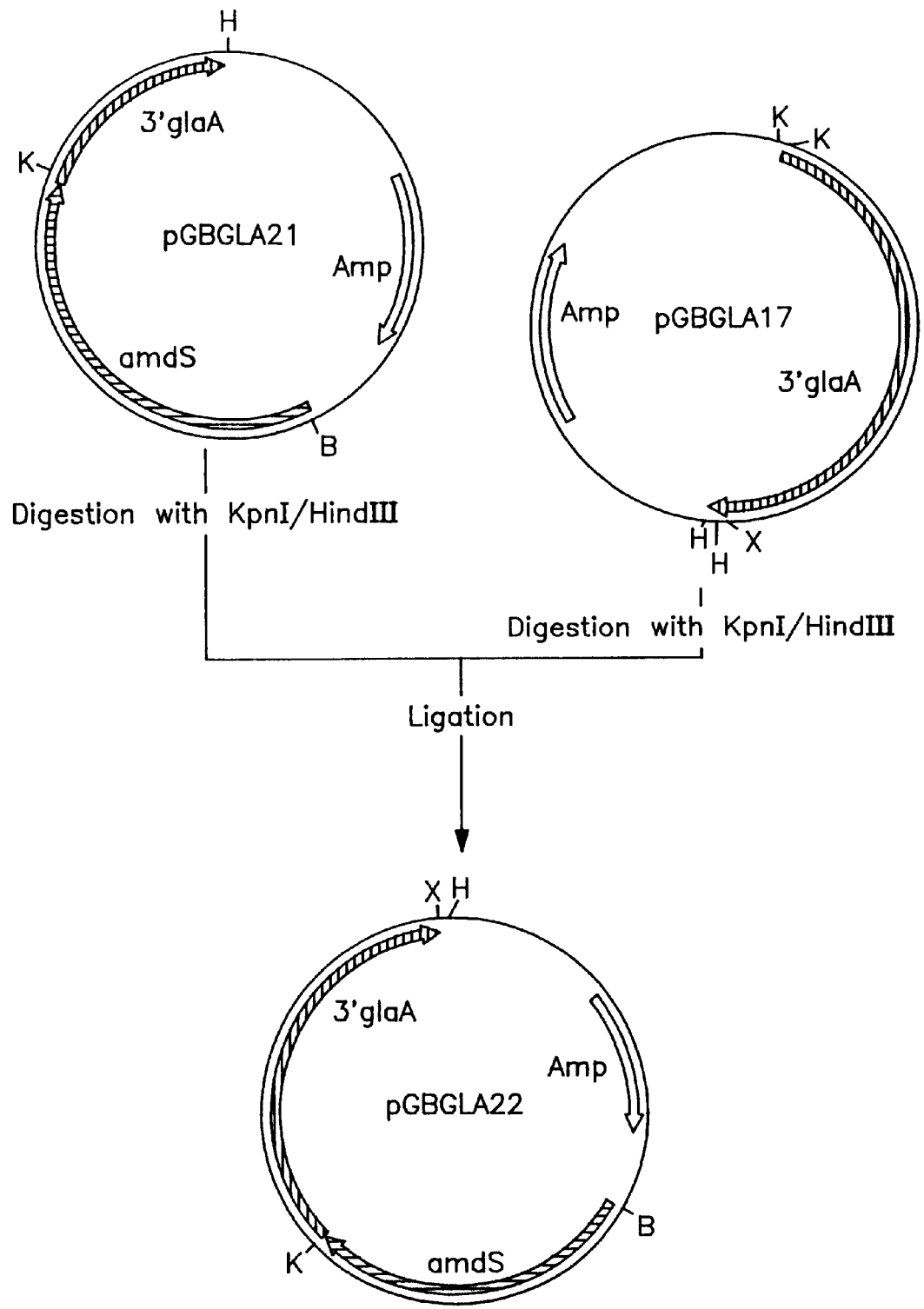

The approximately 1 kb sized 3' glaA non-coding region in this plasmid was exchanged by the 2.2 kb 3' glaA non-coding region of pGBGLA17. pGBGLA17 and pGBGLA21 were digested with KpnI and HindIII. The 2.2 kb 3' glaA non-coding region DNA fragment from pGBGLA17 and the 4.9 kb DNA fragment of pGBGLA21 were isolated by agarose gel electrophoresis, ligated and subsequently molecular cloned by transferring the ligation mixture to *E. coli*. The thus derived plasmid was designated pGBGLA22 (FIG. 19).

Figure 20:
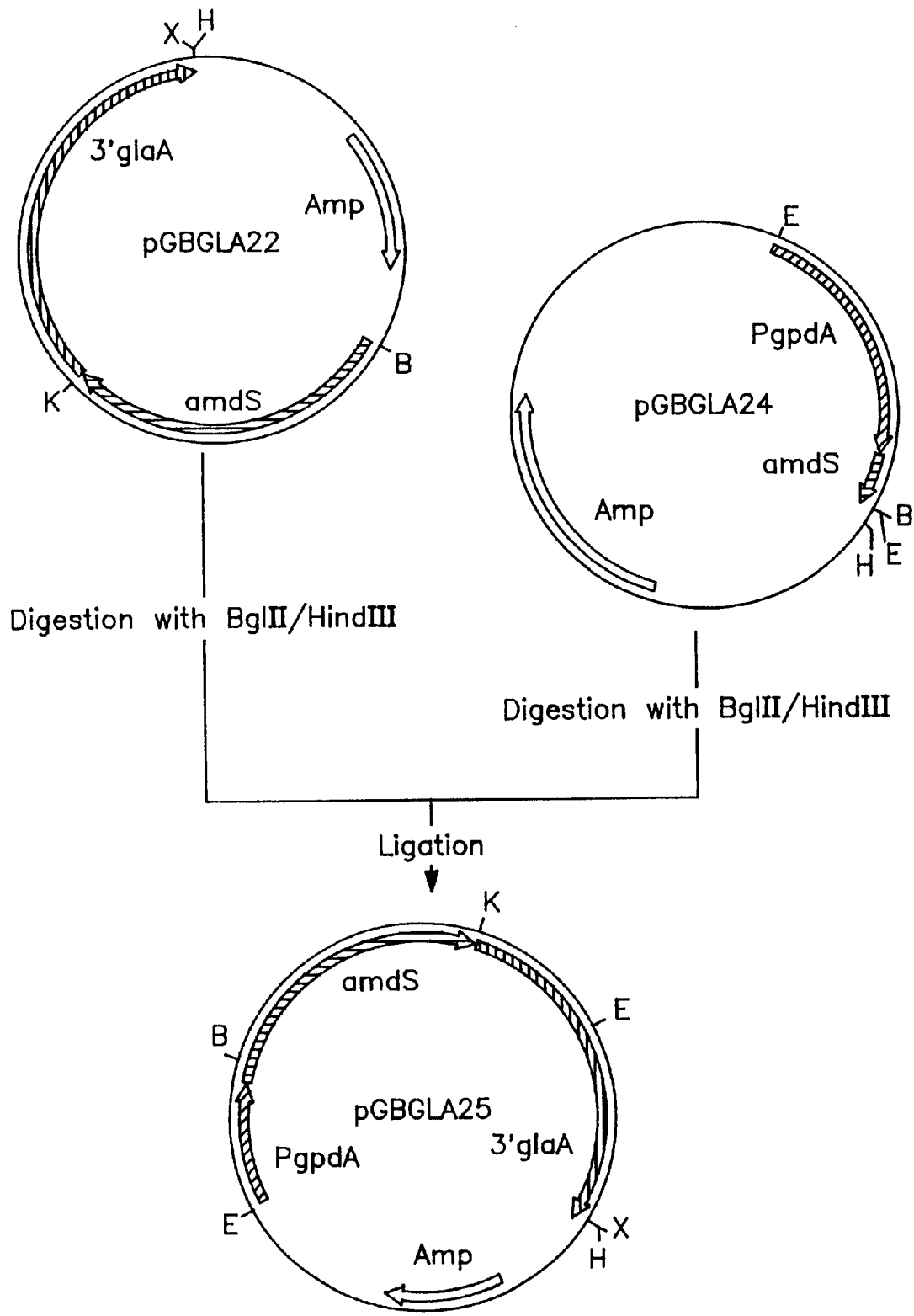

The amdS gene with the extended 3' glaA non-coding region was completed with the gpdA promoter and fused to the remaining part of the amdS gene. pGBGLA22 was digested with BglII and HindIII, the 4.4 kb amdS/3' glaA non-coding region DNA fragment isolated by agarose gel electrophoresis, subsequently ligated with plasmid pGB-GLA24 digested with BglII and HindIII and transferred to *E. coli*. The thus derived plasmid was designated pGBGLA25 (FIG. 20).

pGBGLA25 was partially digested with EcoRI and in the EcoRI site of the gpdA promoter the synthetic fragment consisting of the two oligonucleotides AB3781 (SEQ ID NO:18) and AB3782 (SEQ ID NO:19): 1

Figure 21:
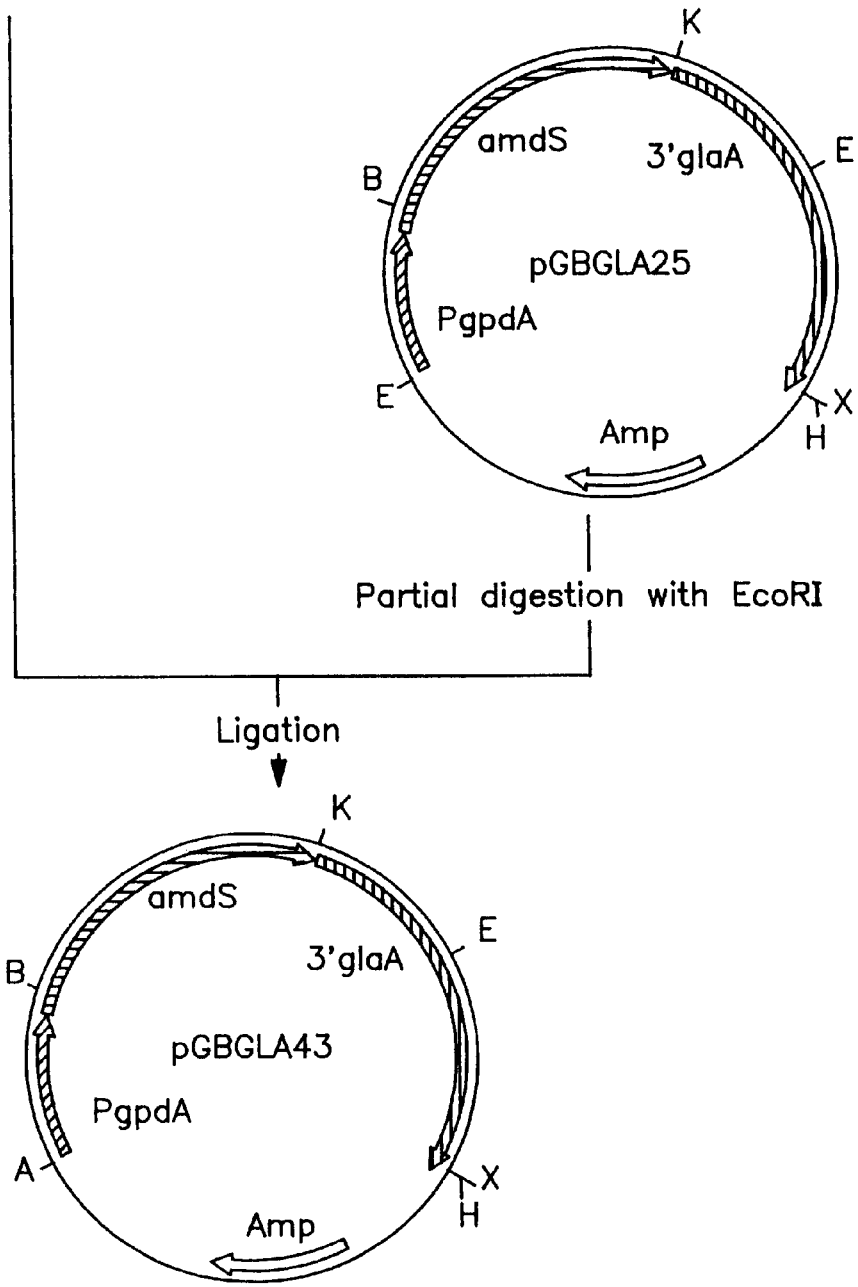

was inserted. This new plasmid was designated pGBGLA43 (FIG. 21). Due to this cloning step, the EcoRI restriction site just in front of the gpdA promoter was destroyed by the introduction of an ApaI restriction site.

Figure 22:
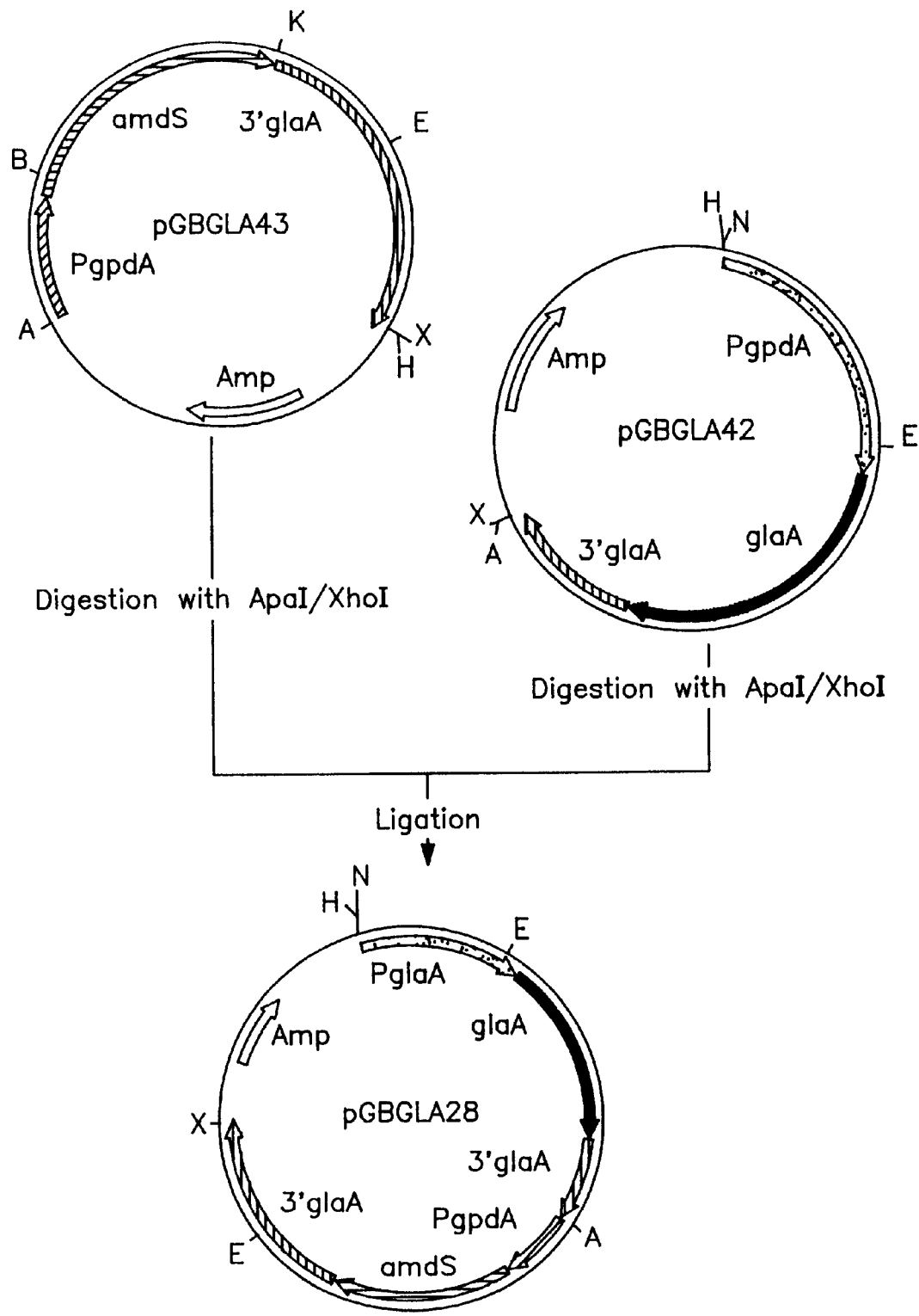

The plasmid pGBGLA43 was digested with ApaI and XhoI, and the 5.3 kb DNA fragment comprising the gpdA promoter/amdS gene/3' glaA non-coding region was isolated by agarose gel electrophoresis, subsequently ligated with pGBGLA42 digested with ApaI and XhoI, and transferred to *E. coli*. The derived plasmid was designated pGBGLA28 (FIG. 22).

Prior to cloning, the 3' glaA non-coding region DNA fragment (positioned at approximately 2.2 kb downstream the stop codon of the glaA gene, designated 3" glaA non-coding region), was amplified and provided with suitable restriction sites using the PCR method.

For this PCR reaction, the plasmid pAB6-1 was used as template and as primers two synthetic oligonucleotides were designed possessing the following sequence:
Oligo AB3746 (SEQ ID NO:20):

(a partly 3" glaA non-coding specific sequence around the SalI site positioned at about 2.2 kb downstream the stop codon of the glaA gene)
Oligo AB3747 (SEQ ID NO:21):

(a partly 3" glaA non-coding specific sequence around the XhoI site located at about 4.4 kb downstream the stop codon of the glaA gene)

Figure 23A:
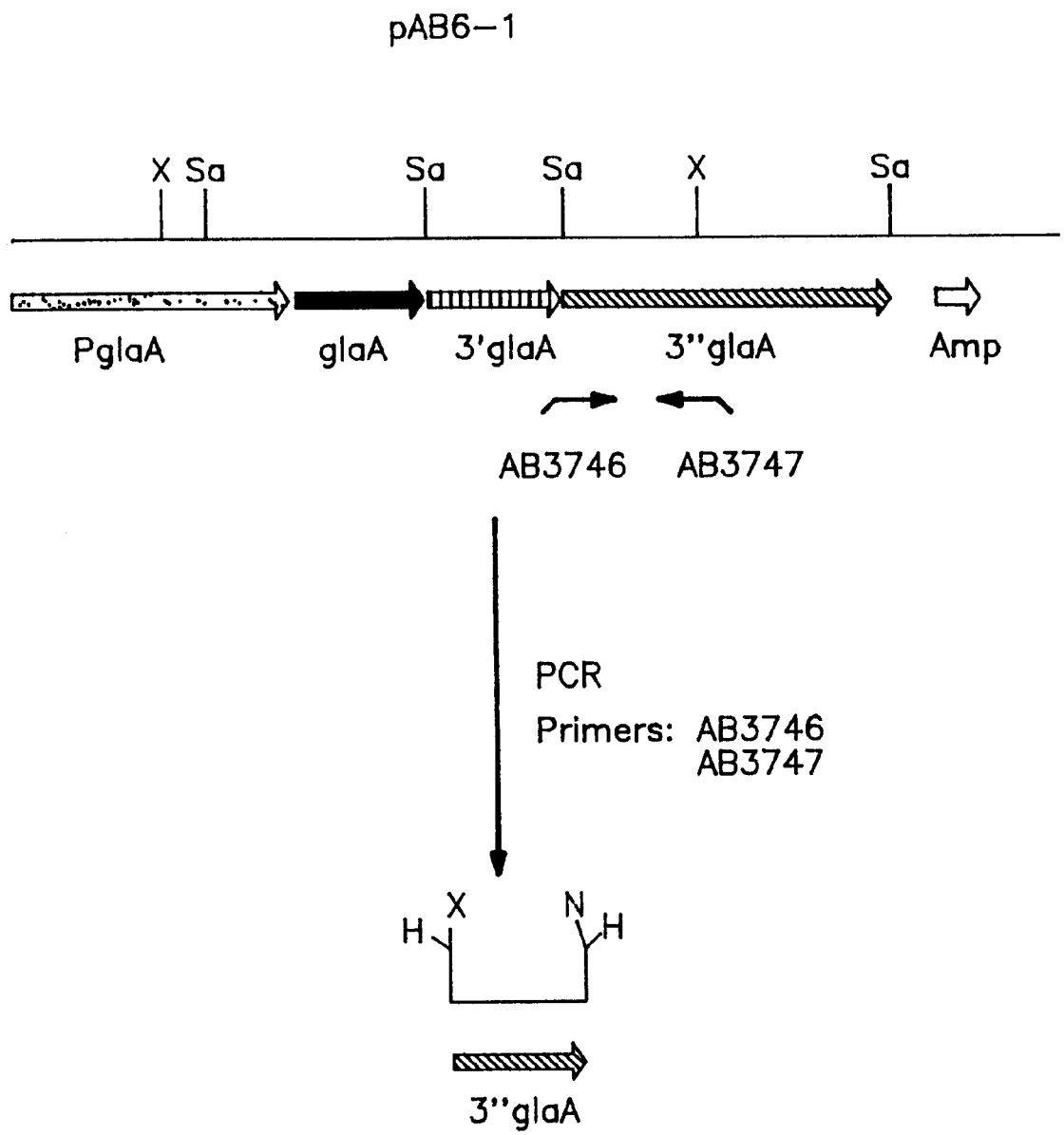
Figure 23B:
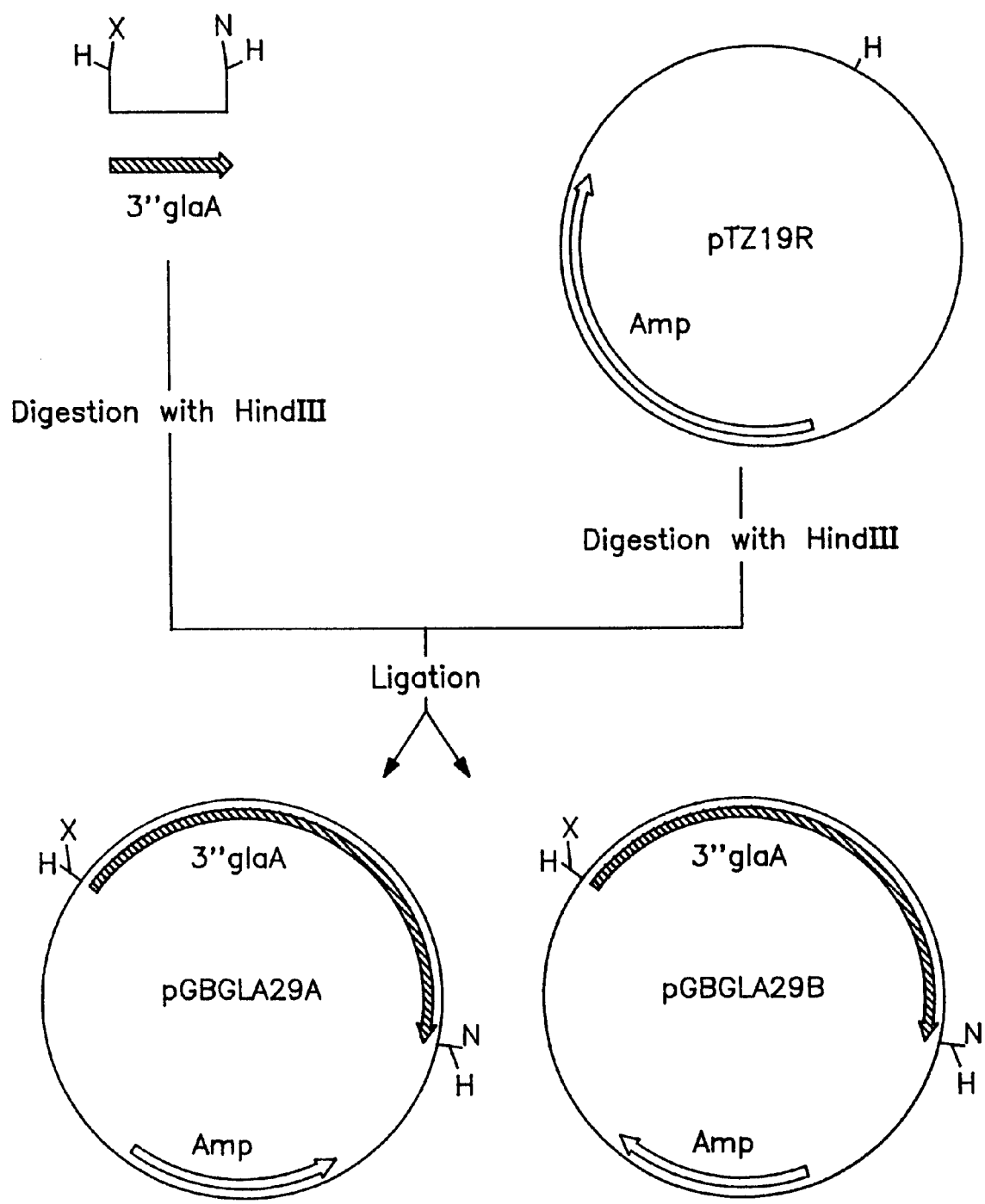

Twenty-five amplification cycles (each: 1 minute 55° C.; 1.5 minutes 72° C.; 1 minute 94° C.) were carried out in a DNA-amplifier (Perkin-Elmer/Cetus). A schematic representation of this amplification is shown in FIG. 23A. The thus obtained DNA fragment was digested with HindIII, purified by agarose gel electrophoresis and ethanol precipitation and subcloned in both orientations into the HindIII site of pTZ19R. The resulting plasmids were designated pGBGLA29A and pGBGLA29B (FIG. 23).

Figure 24:
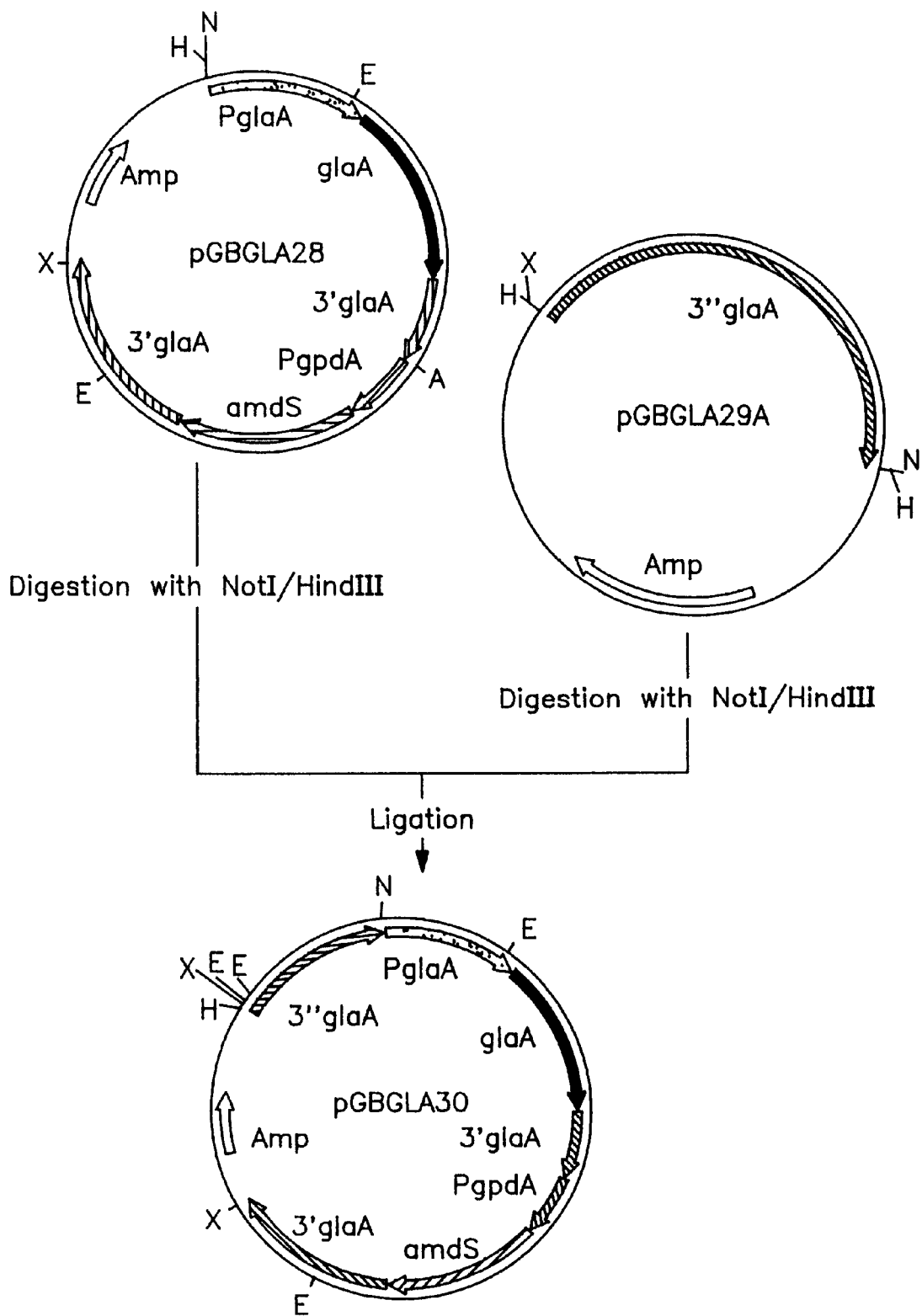

The final step comprises the insertion of the 3" glaA non-coding sequence from pGBGLA29A into the plasmid pGBGLA28. To achieve this, pGBGLA29A was digested with HindIII and NotI. The 2.2 kb sized 3' glaA non-coding region fragment was isolated by agarose gel electrophoresis, subsequently ligated to pGBGLA28 digested with HindIII and NotI and transferred to *E. coli*. The derived integration vector was designated. pGBGLA30 (FIG. 24).

Transformation of *A. niger* GBA-107 with the Integration Vector pGBGLA30

Figure 26A:
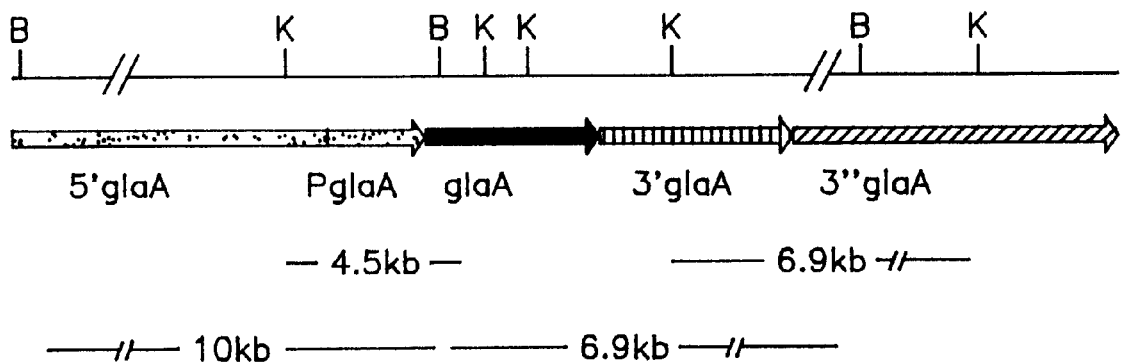
Figure 26B:
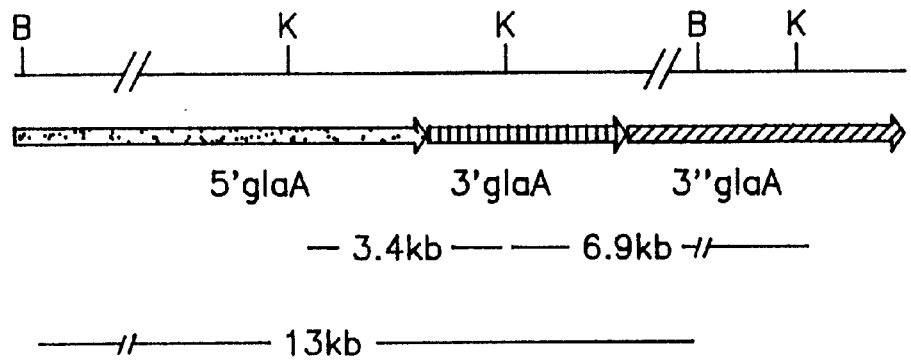
Figure 26C:
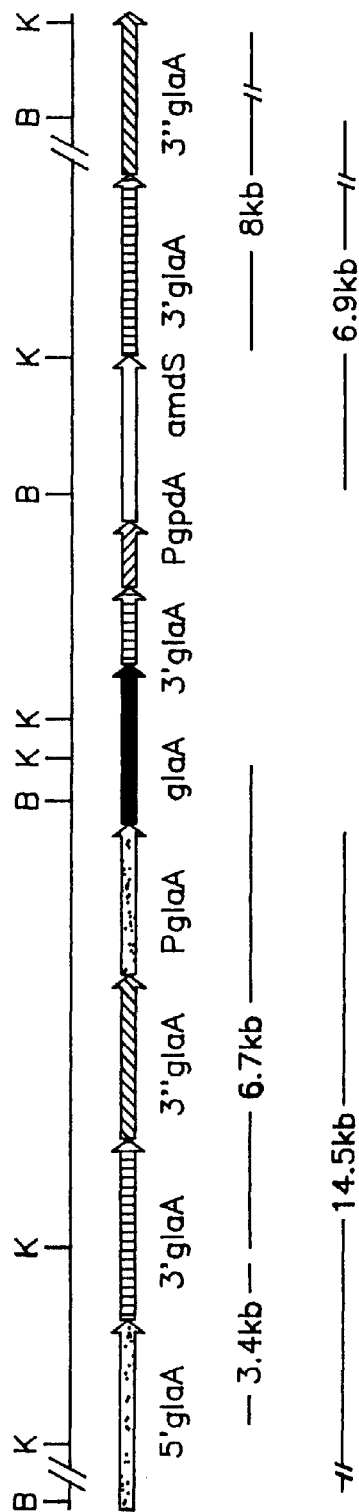
Figure 26D:
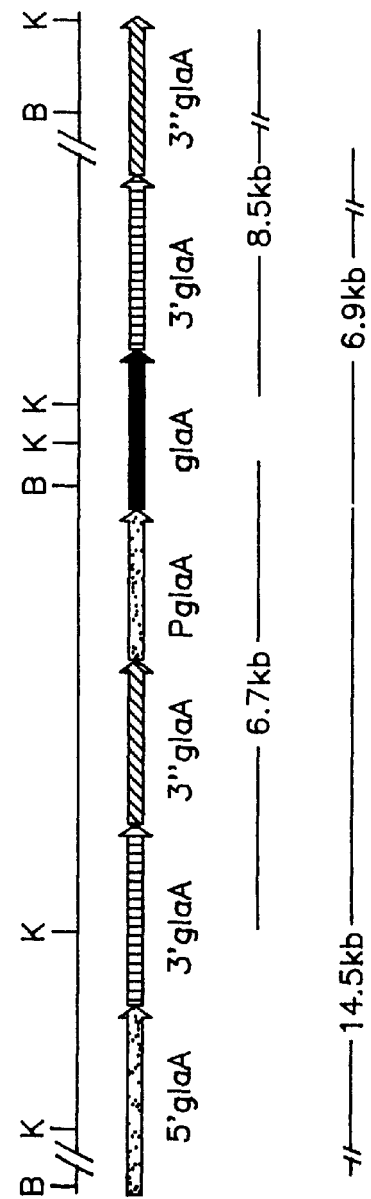

Prior to transformation, *E. coli* sequences were removed from the integration vector pGBGLA30 by XhoI digestion and agarose gel electrophoresis. The *A. niger* strain GBA-107 was transformed with either 5 or 10 μg DNA fragment by procedures as described in the experimental section. Single *A. niger* transformants were purified several times on selective acetamide containing plates. Spores of individual transformants were collected following growth for about 5 days at 30° C. on 0.4% potato dextrose agar (Oxoid, England) plates. Southern analyses were performed to verify whether integration into the 3' glaA non coding region of the endogenous truncated glaA locus had occurred. High molecular weight DNA of several transformants was isolated, digested with either KpnI, or BglII and subsequently fractionated by electrophoresis on a 0.7% agarose gel. After transfer to nitrocellulose filters, hybridization was performed according to standard procedures. As probe a $^{32}$P-labelled approx. 0.7 kb XhoI/,SalI A promoter fragment isolated from plasmid pAB6-4 (described in example 1) was used. The results of only 3 transformants (#107-5, #107-9 and #107-7) and the reference strain *A. niger* GBA107 and its ancestor *A. niger* CBS 531.88 are shown as example in FIG. 25. For a better understanding of the autoradiograph, a schematic presentation is given in FIGS. 26A,B,C showing the sizes of the hybridizing fragments of the intact glaA locus, the truncated glaA locus and of the truncated glaA locus with a single pGBGLA30 copy integrated into the predefined 3' glaA non-coding region.

Characteristic for the intact glaA locus is a 4.5 kb hybridizing fragment in a KpnI digest and a 10 kb hybridizing fragment in a BglII digest. Characteristic for the truncated glaA locus of *A. niger* GBA-107 is a 3.4 kb hybridizing fragment in a KpnI digest and a 13 kb hybridizing fragment in a BglII digest. In case of integration of the pGBGLA30 vector into the 3' region of the truncated glaA locus, in a KpnI digest an additional 6.7 kb hybridizing fragment is expected besides the 3.4 kb hybridizing fragment and in a BglII digest the 13 kb hybridizing fragment is absent and replaced by a 14.5 kb hybridizing fragment. As can be seen in FIG. 25, transformants #107-5 and #107-9 show the expected hybridization pattern of a single pGBGLA,30 copy integrated into the predefined 3' non-coding region of the truncated glaA locus. The hybridization pattern of transformant #107-7 indicates integration of the pGBGLA30 copy elsewhere into the genome of *A. niger* GBA-107. The transformants with the correctly integrated pGBGLA30 copy were designated GBA-119 and GBA-122 and were used to remove subsequently the amdS selection marker gene properly.

Removal of the amdS Selection Marker Gene from *A. niger* GBA-119 and GBA-122 by Counter-Selection on Fluoracetamide Containing Plates The amdS selection marker gene in the transformants *A. niger* GBA-119 and GBA-122 was removed again as described in the experimental section. The removal of the amdS selection marker gene in several surviving recombinant strains was verified by Southern analysis of the chromosomal DNA. High molecular weight DNA was isolated, digested either with KpnI or BglII and subsequently separated by electrophoresis on a 0.7% agarose gel. Following transfer to nitrocellulose, hybridization was performed according to standard procedures. As probe the 32p labelled 2.2 kb HindIII/NotI 3" glaA non-coding fragment isolated from plasmid pGBGLA29A (described previously, FIG. 24) was used.

Figure 27A:
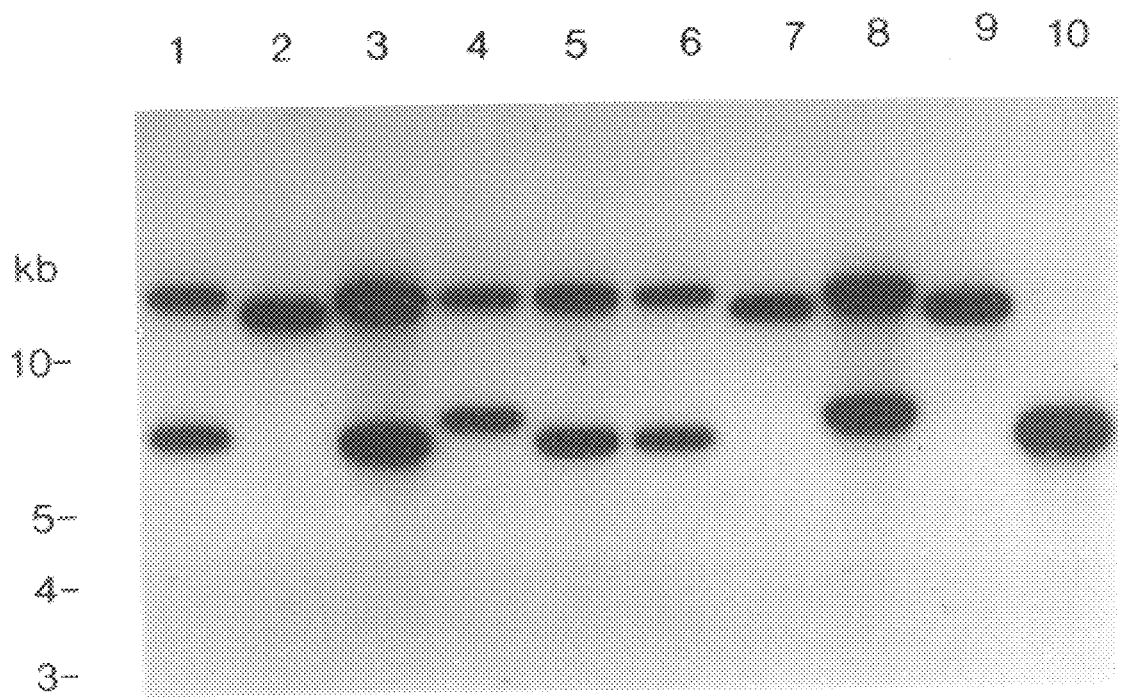

A schematic presentation of the hybridizing fragments is shown in FIG. 26. The results of only 3 surviving recombinant strains from *A. niger* GBA-119 (#AG5-5, #AG5-6 and #AG5-7) as well as 3 surviving recombinant strains from *A. niger* GBA-122 (#AG9-1, #AG9-2 and #AG9-4) and the reference strains *A. niger* CBS 531.88 and *A. niger* GBA-107 are shown in FIGS. 27A,B.

In strain *A. niger* CBS 531.88 a 6.9 kb hybridizing fragment is present in a KpnI digest and a 6.9 kb hybridizing fragment in a BglII digest. In the *A. niger* GBA-107 strain a 6.9 kb hybridizing fragment is present in a KpnI digest and a 13 kb hybridizing fragment in a BglII digest. In the *A. niger* strains GBA-119 and GBA-122 with a single pGBGLA30 copy integrated into the 3' glaA non-coding region an 8 kb and a 6.7 kb hybridizing band are present in a KpnI digest and a 14.5 kb and a 7.6 kb hybridizing band are present in a BglII digest.

Figure 27B:
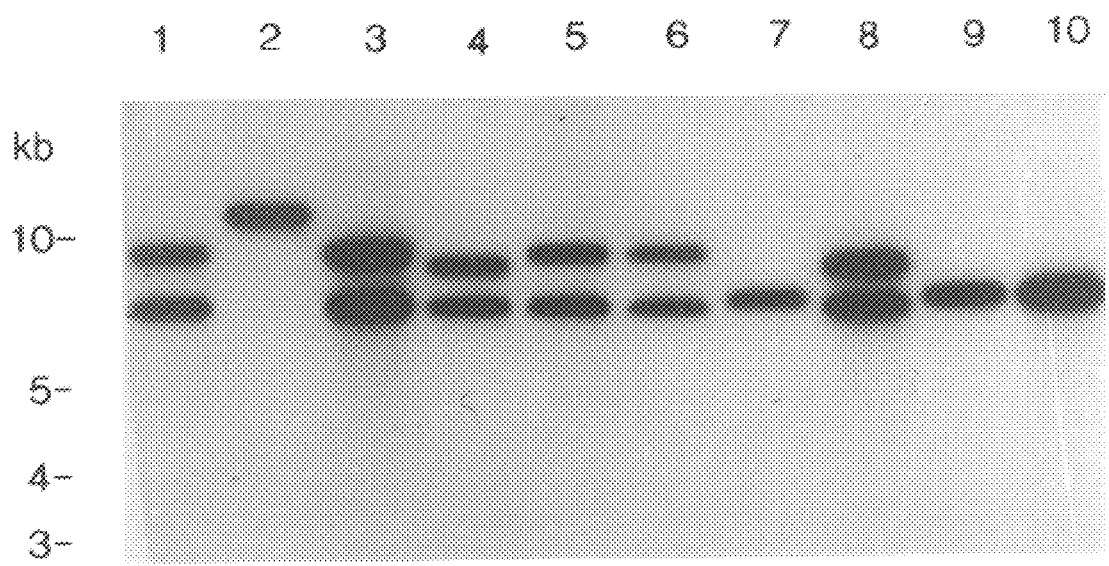

Specific for correct removal of the amdS selection marker gene is the presence of a 6.7 kb and a 8.5 kb hybridizing fragment in a KpnI digest and concomitant loss of the 8 kb hybridizing fragment. In a BglII digest, a 14.5 kb and a 6.9 kb hybridizing fragment with concomitant loss of the 7.6 kb hybridizing fragment is specific for the absence of the amdS selection marker gene. As can be seen in FIG. 27, strains #AG5-7, #AG5-5, #AG9-1 and #AG9-4 show the expected hybridizing pattern of the correctly removed amdS selection marker gene. These strains were designated GBA-120, GBA-121, GBA-123 and GBA-124 respectively. The hybridizing patterns of strains #AG5-6 and #AG9-2 indicate loss of the entire pGBGLA30 copy resulting in the parental *A. niger* GBA-107 strain with only a truncated glaA locus.

Strains *A. niger* GBA-120, GBA-121, GBA-123 and GBA-124 were tested in shake flask fermentations for the ability to produce glucoamylase. As reference strains *A. niger* CBS 531.88, GBA-107, GBA-119 and GBA-122 were tested. Shake flask fermentations and the glucoamylase assay were performed as described in the experimental section. In the strains GBA-119 till GBA-124 levels varying between 150–200 U/ml could be measured. These glucoamylase levels were to be expected and comparable to levels obtained with the parental untransformed wild-type strain *A. niger* CBS 531.88.

EXAMPLE 3

Marker Gene Free Introduction of the Phytase Gene Targeted at the 3' glaA Non-Coding Region of the Truncated glaA Locus in *A. niger* GBA-107

In this example describes the introduction of a gene into the genome of *A. niger* by using approximately the same approach and procedures as described in the previous example. the main difference is that the gene of interest and the selection marker gene are located on two-separate vectors and that these vectors are co-transformed to *A. niger*. Besides the gene of interest or the marker gene, the vectors contain DNA sequences homologous to the host genome to target the vectors at a predefined genomic locus of the host, by a single cross-over event. By performing the fluoracetamide counter-selection on these (co)-transformants (as described in the experimental procedures), the amdS marker gene will be deleted properly by an internal recombination event between the DNA repeats that are created by integration via a single cross-over event.

Description of the Vectors Used for Co-Transformation

The vector with the gene of interest pGBGLA53 consists of the *A. ficuum* phytase gene under control of the *A. niger* glucoamylase (glaA) promoter flanked by 3' glaA non-coding sequences to direct integration at the 3' glaA non-coding region. The vector with the selection marker gene pGBGLA50 consists of the *A. nidulans* amdS gene under control of the *A. nidulans* gpdA promoter flanked by 3' glaA non-coding sequences to direct integration at the 3' glaA non-coding region.

Construction Pathway of pGBGLA50

The construction of pGBGLA50 comprises one cloning step. Plasmid pGBGLA29A was digested with HindIII and the sticky ends were filled in using the Klenow fragment of *E. coli* DNA polymerase. Next, the 2.2 kb 3" glaA non-coding region fragment was isolated by agarose gel-electrophoresis, subsequently ligated into pGBGLA43 digested with ApaI and treated with T4 DNA polymerase to generate blunt ends, and transferred to *E. coli*. The derived plasmid with the 3" glaA non-coding region DNA fragment in the' correct orientation was designated pGBGLA50 (FIG. 28).

Construction pathway of pGBGLA53

Figure 29:
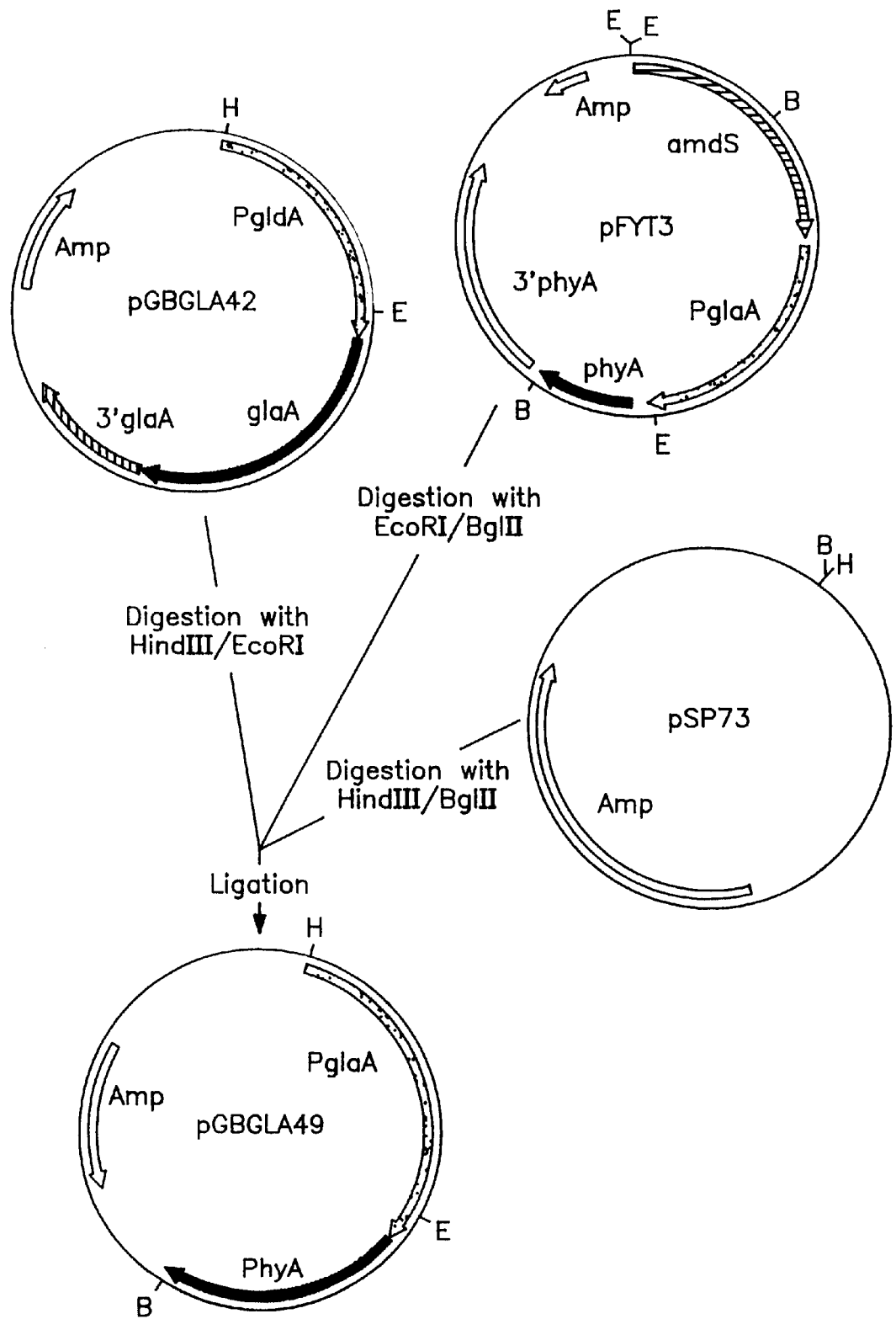

The first step in the construction pathway of pGBGLA53 is the subcloning of two fragments, comprising the glaA promoter fused to almost entire coding sequence of the *A. ficuum* phytase gene. To achieve this, plasmid pGBGLA42 was digested with HindIII and EcoRI and the 1.8 kb HindIII/EcoRI 5' glaA promoter fragment was isolated by agarose gel-electrophoresis. Plasmid pFYT3 (European Patent Application 0 420 358 A1) was digested with EcoRI and BglII and the 1.6 kb EcoRI/BglII fragment comprising the 3' part of the glaA promoter fused to the 5' part of the phytase gene was isolated by agarose gel-electrophoresis and ligated together with the 1.8 kb HindIII/EcoRI 5' glaA promoter fragment isolated from pGBGLA42 into the HindIII and BglII sites of pSp73 (Promega). The resulting plasmid was designated pGBGLA49 (FIG. 29).

The next step is the cloning of a 3' glaA non-coding region DNA fragment into pGBGLA49. Prior to cloning, this 3' glaA non-coding region DNA fragment (positioned at approximately 2.2 kb downstream the stop codon of the glaA gene) was amplified and provided with suitable restriction sites using the PCR method.

For this PCR reaction, the plasmid pAB6-1 was used as template and as primers two synthetic oligonucleotides with the following sequence were designed:

Oligo AB4234 (SEQ ID NO:22):

5' GAAGACCCAGTCAAGCTTGCATGAGC 3'

(a 3' glaA non-coding sequence located approximately 2.2 kb downstream the stopcodon of the glaA gene)

Oligo AB 4235 (SEQ ID NO:23):

5' TGACCAATTAAGCTTGCGGCCGCTCGAG-GTCGCACCGGCAAAC 3'

(a 3' glaA non-coding sequence located approximately 4.4 kb downstream the stopcodon of the glaA gene)

Figure 30A:
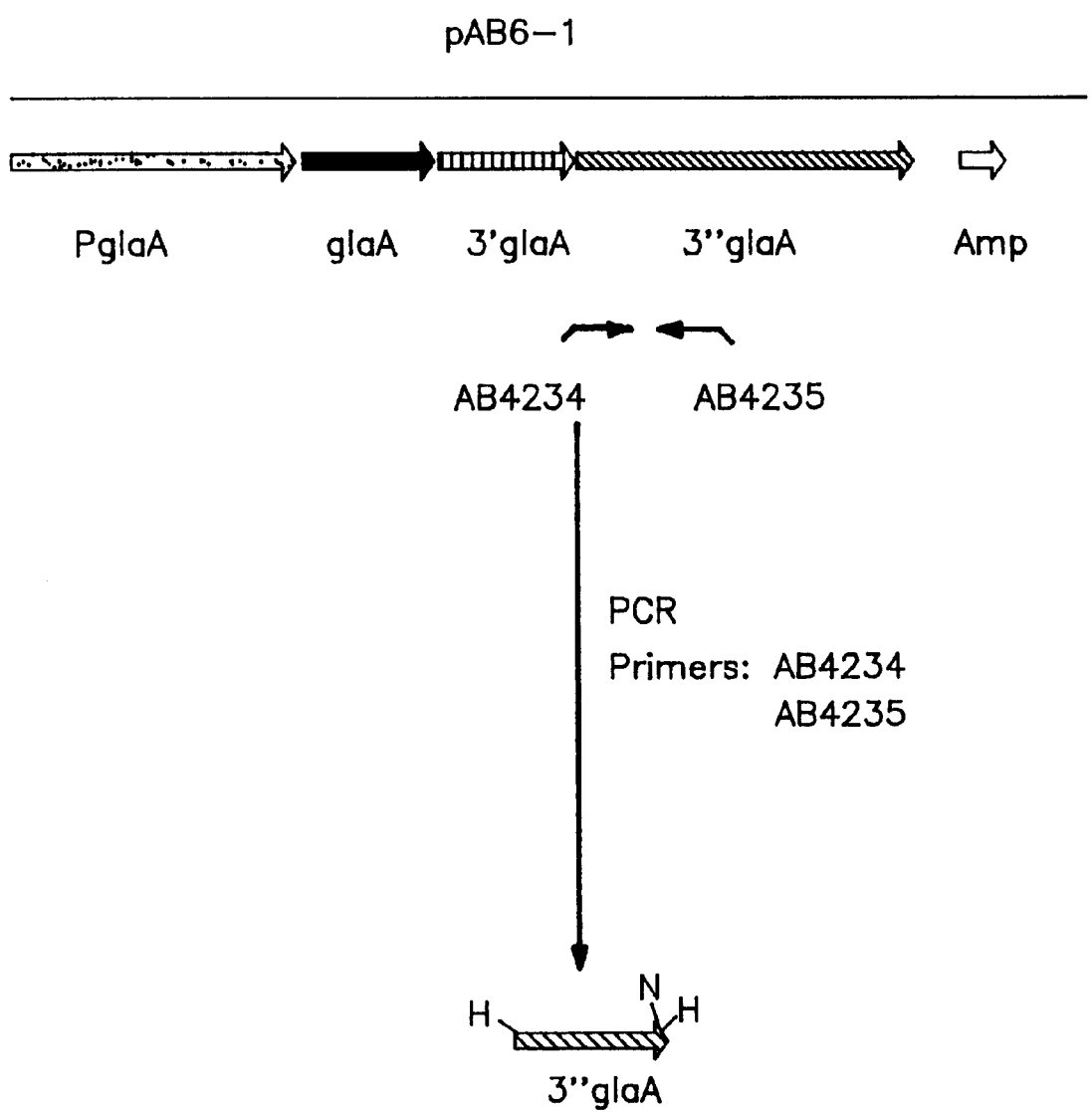
Figure 30B:
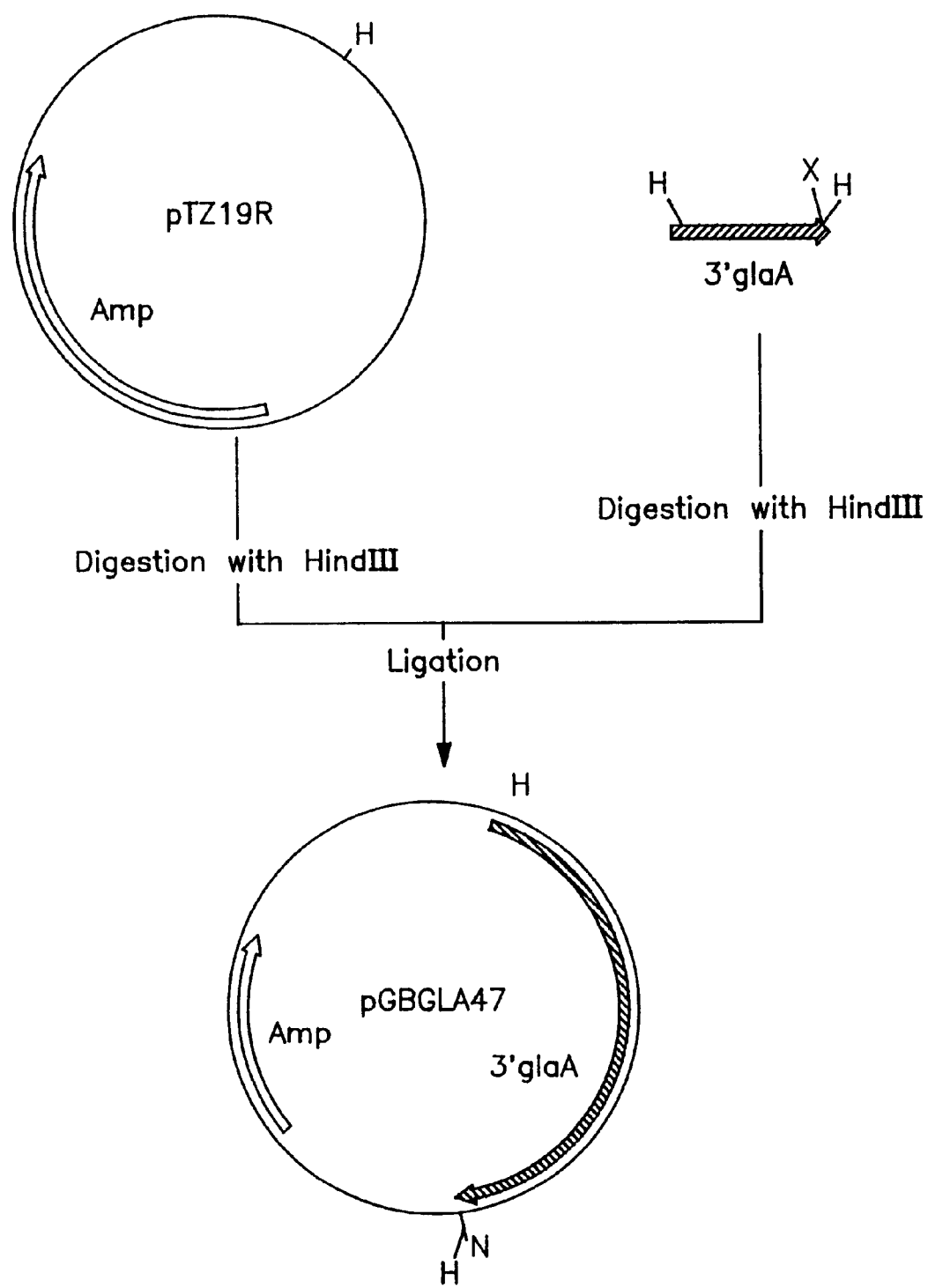

Twenty-five amplification cycles (each: 1 minute 94° C.; 1 minute 55° C.; 1.5 minutes 72° C.) were carried out in a DNA-amplifier (Perkin-Elmer). A schematic representation of this amplification is shown in FIG. 30A. The thus obtained fragment was digested with HindIII, purified by agarose gel-electrophoresis and subcloned into the HindIII site of pTZ19R. The resulting plasmid was designated pGBGLA47 (FIG. 30).

Figure 31:
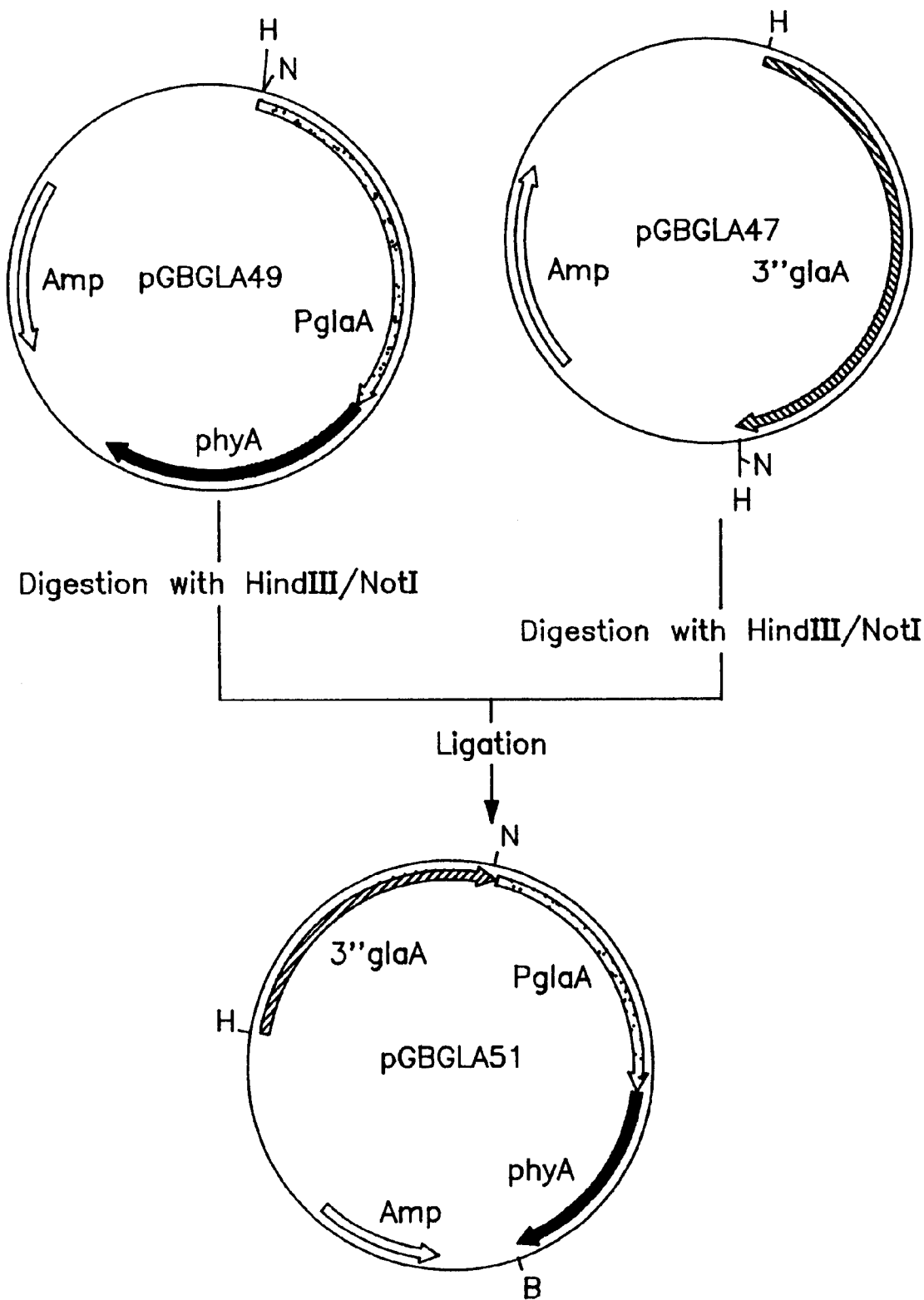

Plasmid pGBGLA47 was digested with HindIII en NotI, the 2.2 kb 3" glaA non-coding DNA fragment was isolated by agarose gel-electrophoresis and cloned into the HindIII and NotI sites of pGBGLA49. The resulting plasmid was designated pGBGLA51 (FIG. 31).

The last step in the construction pathway of pGBGLA53 is the cloning of the DNA fragment comprising the remaining part of the phytase coding sequence fused to the 3' glaA non-coding DNA fragment located just downstream the stop codon of the glaA gene. Prior to cloning, the remaining part of the phytase gene and the 3' glaA non-coding DNA fragment located just downstream the stopcodon of the glaA gene were fused and provided with suitable restriction sites using the PCR method. In the PCR, plasmid pAB6-1 was used as template and as primers two synthetic oligonucleotides were used, having the following sequences:
Oligo AB4236 (SEQ ID NO:24):

5' TGACCAATAAAGCTTAGATCTGGGGGTGATTGGGCGGAGTGTTTTGCTTAGACAATCAATCCATTTCGC 3'

(36 bp of the phytase coding sequence, starting at the BglII site until the stopcodon fused to the 3' glaA non-coding region, starting just downstream the stopcodon of the glaA gene)
Oligo AB4233 (SEQ ID NO:25):

5' TGACCAATAGATCTAAGCTTGACTGGGTCTTCTTGC 3'

(a 3' glaA non-coding sequence located approximately 2.2 kb downstream the stopcodon of the glaA gene)

Figure 32A:
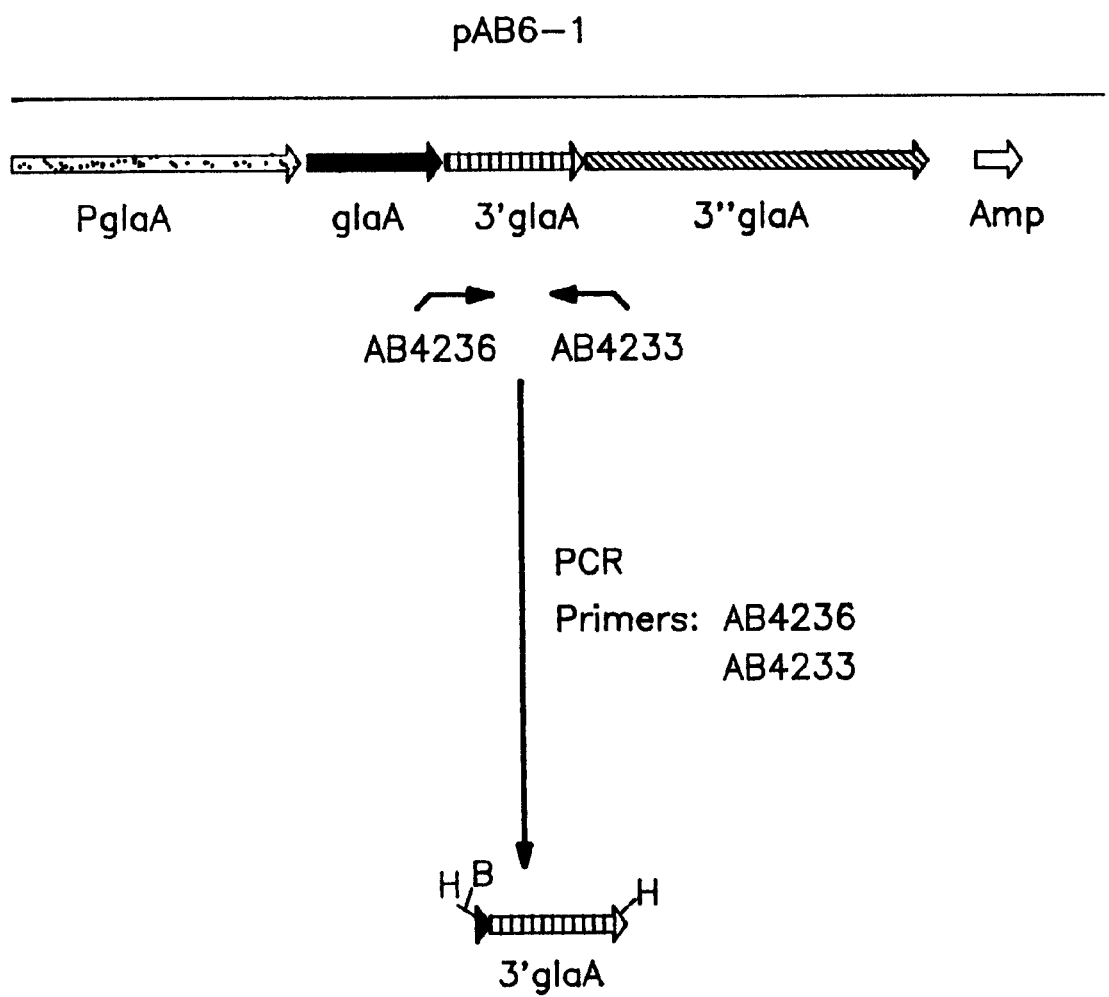
Figure 32B:
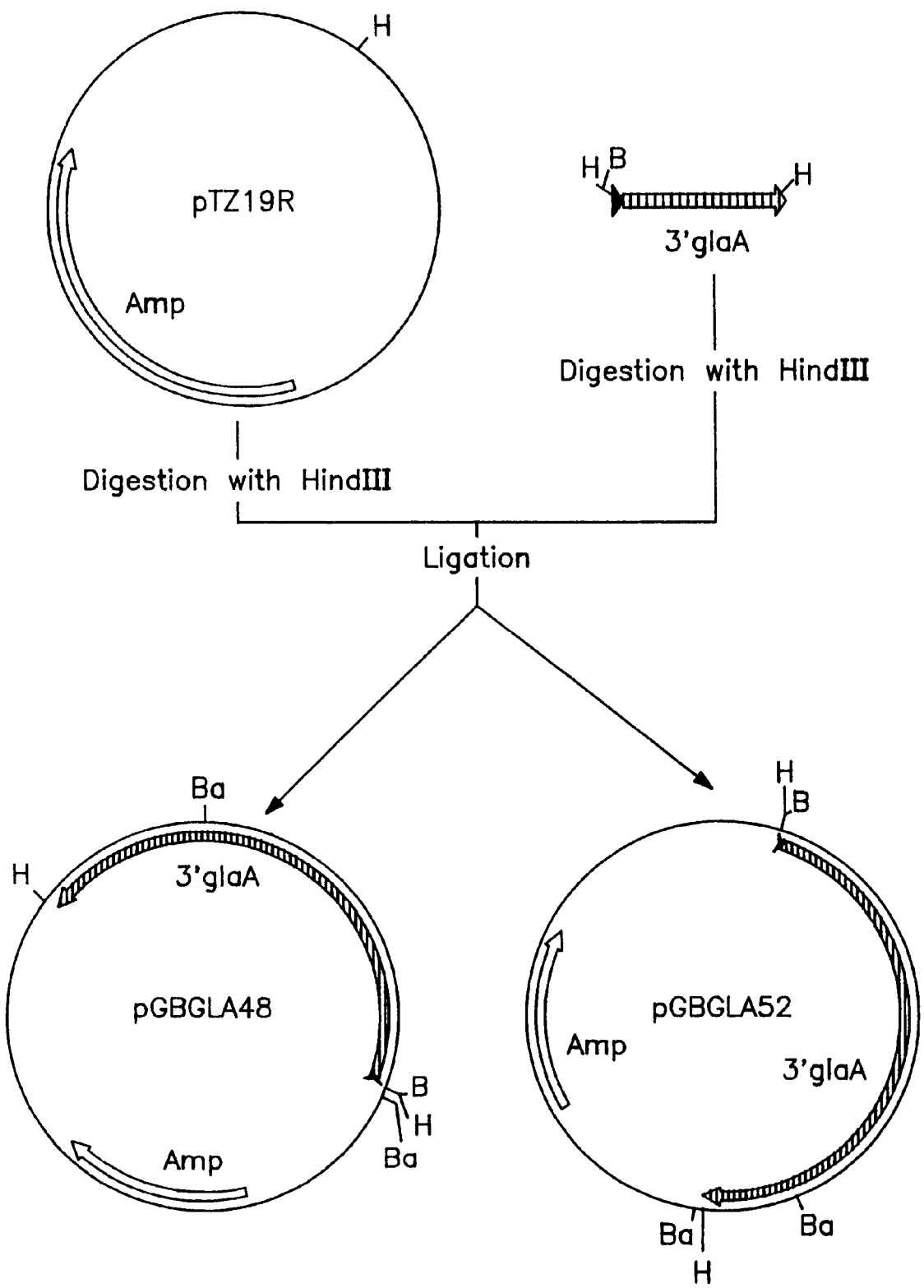

Twenty-five amplification cycles (each: 1 minute 94° C.; 1 minute 55° C.; 1.5 minutes 72° C.) were carried out in a DNA-amplifier (Perkin-Elmer). A schematic representation of this amplification is shown in FIG. 32A. The thus obtained fragment was digested with HindIII, purified by agarose gel-electrophoresis and subcloned in both orientations into the HindIII site of pTZ19R. The resulting plasmids were designated pGBGLA48 and pGBGLA52 (FIG. 32B).

Figure 33:
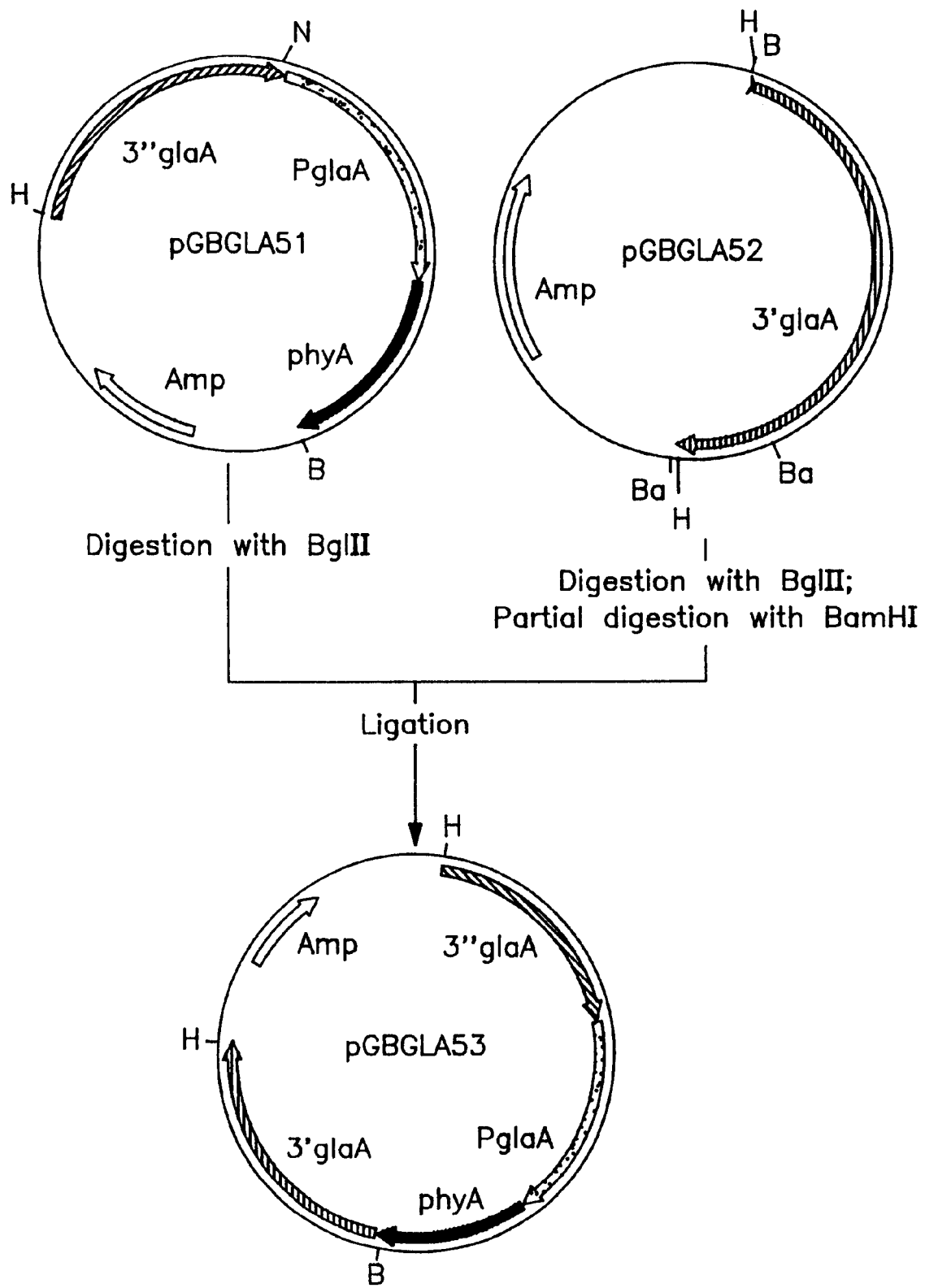

Plasmid pGBGLA52 was digested with BglII and partially digested with BamHI, the 2.2 kb phytase/3' glaA non-coding DNA fragment was isolated by agarose gel-electrophoresis and cloned into the BglII site of pGBGLA51. The derived plasmid with the 2.2 kb phytase/3' glaA non-coding DNA fragment in the correct orientation was designated pGBGLA53 (FIG. 33).

Transformation of *A. niger* GBA-107 with the Vectors pGBGLA50 and pGBGLA53

Prior to transformation, *E. coli* sequences were removed from pGBGLA50 and pGBGLA53 by respectively XhoI or HindIII digestion followed by agarose gel-electrophoresis. The *A. niger* GBA-107 strain was transformed with respectively 1 μg pGBGLA50 fragment plus 1 μg pGBGLA53 fragment, 1 μg pGBGLA50 fragment plus 5 μg pGBGLA53 fragment, or 1 μg pGBGLA50 fragment plus 10 μg pGBGLA53 fragment using the transformation procedure described in the experimental, section.

Single transformants were isolated, purified and Southern analysis was performed, using the same digests and probes as described in example 2, to verify integration of both pGBGLA50 and pGBGLA53. In about 10–20% of the analyzed transformants both pGBGLA5o and pGBGLA53 were integrated into the genome of the *A. niger* GBA-107 host strain. The transformant showing the correct integration pattern of a single copy pGBGLA50 and a single copy pGBGLA53, both integrated at the predefined 3' glaA non-coding region of the truncated glaA locus was used to remove subsequently the amdS selection marker gene.

Removal of the amdS Marker Gene by Counter-Selection on Fluoracetamide Containing Plates By performing the fluoracetamide counter-selection (as described in the experimental procedures), the amdS marker gene was deleted by an internal recombination event between the DNA repeats that were created by integration via a single cross-over event (i.e. the 3' glaA non-coding sequences). Proper removal of only the amdS marker gene was verified by Southern analysis using the same digests and probes as in example 2.

EXAMPLE 4

Marker Gene Free Introduction of the glaA Gene and the Phytase Gene in *A. oryzae*

This example describes the marker gene free introduction of the glaA gene or the phytase gene in *A. oryzae* NRRL3485. *A. oryzae* NRRL3485 was transformed as described in the experimental section using the same vectors and approach as described in examples 2 and 3. Single transformants were isolated, purified and Southern analysis of chromosomal DNA of several transformants was performed to verify integrations of respectively the pGBGLA30 vector or the pGBGLA50 and pGBGLA53 vectors. In the Southern analysis, the same digests and probes were used as described in example 2.

Removal of the amdS Gene by Counter-Selection on Fluoracetamide Containing Plates In case of integration of the pGBGLA30 vector, a transformant with a single copy of the pGBGLA30 integrated into the genome of the host strain *A. oryzae* NRRL3485 was used to remove the amdS gene properly. The counter-selection on fluoracetamide containing plates was performed as described in the experimental section. Correct removal of the amdS gene was verified by Southern analysis of chromosomal DNA of several fluoracetamide resistant strains. The same digests and probes were used as described in Example 2.

In case of co-transformation of the pGBGLA50 and pGBGLA53 vector, a transformant with a single copy of both pGBGLA50 and pGBGLA53 integrated into the host genome was used to remove the amdS marker gene properly. The counter-selection using fluoracetamide plates was performed as described in the experimental section. Correct removal of the amdS marker gene (e.g. the pGBGLA50 vector) was verified by Southern analysis of chromosomal DNA of several fluoracetamide resistant strains using the same digests and probes as described in example 2.

EXAMPLE 5

Marker Gene Free Introduction of the glaA Gene and the Phytase Gene in *T. reesei*

This example describes the marker gene free introduction of the glaA gene or the phytase gene in Trichoderma reesei strain QM9414 (ATCC 26921). *T. reesei* QM9414 was transformed as described in the experimental section using the same vectors and approach as described in examples 2 and 3. Single transformants were isolated, purified and Southern analysis of chromosomal DNA of several transformants was performed to verify whether integration of respectively the pGBGLA30 vector or the pGBGLA50 and pGBGLA53 vectors. In the Southern analysis, the same digests and probes were used as described in example 2.

Removal of the amdS Gene by Counter-Selection on Fluoracetamide Containing Plates In case of integration of the pGBGLA30 vector, a transformant with a single copy of the pGBGLA30 integrated into the genome of the host strain *T. reesei* QM9414 was used to remove the amdS gene properly. The counter-selection on fluoracetamide containing plates was performed as described in the experimental section. Correct removal of the amdS gene was verified by Southern analysis of chromosomal DNA of several fluoracetamide resistant strains.

In case of co-transformation of the pGBGLA50 and pGBGLA53 vector, a transformant with a single copy of both pGBGLA50 and pGBGLA53 integrated into the host genome was used to remove the amdS marker gene properly. The counter-selection using fluoracetamide plates was performed as described in the experimental section. Correct removal of the amdS marker gene (e.g. the pGBGLA50 vector) was verified by Southern analysis on chromosomal DNA of several fluoracetamide resistant strains using the same digests and probes as described in example 2.

EXAMPLE 6

Marker Gene Free Introduction into *P. chrysogenum* of a *P. chrysogenum* Gene by Co-Transformation Using the amdS-Gene as a Selection Marker In this example the marker gene free introduction of a gene into the genome of *P. chrysogenum* by co-transformation is described.

In the co-transformation procedure, 2 different pieces of DNA are offered to the protoplasts, one of them being the. amdS-selection marker, on the presence of which the first transformant selection takes place, as described in the experimental section, the second being another piece of DNA of interest, e.g. encoding a particular enzyme of interest. In a certain number of transformants both pieces of DNA will integrate into the chromosomes and will be stably maintained and expressed.

The amdS-selection marker gene can then be removed selectively from purified transformants by applying the counter-selection procedure as described in the experimental section, while the second piece of DNA will remain stably integrated into the chromosomes of the transformant. As an example to illustrate the general applicability of the method the stable, marker gene free introduction of a niaD-gene is described which enables a niaD$^-$-host to grow on nitrate as sole nitrogen-source.

Host for this co-transformation is a *P. chrysogenum* niaD$^-$-strain which lacks nitrate reductase and therefore is unable to grow on plates containing nitrate as sole nitrogen source. These strains can be easily obtained by well known procedures (Gouka et al., Journal of Biotechnology 20(1991), 189–200 and references there in).

During the co-transformation (procedure described in experimental section), two pieces of DNA are simultaneously offered to the protoplasts: the 7.6 kb EcoRI restriction fragment from pGBGLA28 containing the amdS selection marker gene and the 6.5 kb EcoRI restriction fragment from pPC1-1, containing the *P. chrysogenum* niaD-gene. Prior to transformation, both fragments have been separated from *E. coli* vector sequences by agarose gel-electrophoresis and purified from agarose gel by electro-elution. The first selection of transformants took place on selective plates containing acetamide as sole nitrogen source as described in the experimental section.

Among the transformants, co-transformants are found by replica plating spores of purified transformants to plates containing nitrate as sole nitrogen source. Typically about 20–60% of the replica plated transformants were able to grow on this medium, indicating that in these transformants not only the amdS selection marker gene but also the niaD-gene has integrated into the genome and is expressed. Removal of the amdS Gene by Counter-Selection on Fluoracetamide Containing Plates The amdS selection marker gene is subsequently removed from the co-transformants by counter-selection on fluoracetamide.

For direct selection on the amdS$^-$/niaD$^+$-phenotype the medium used contained 10 mM fluor-acetamide. Spores were plated at a density of $10^4$ spores per plate. After 5–7 days of incubation at 25° C., fluor-acetamide resistant colonies could be identified as solid colonies clearly distinct from the faint background. The niaD$^+$-phenotype of the recombinants is demonstrated by their growth on the fluoracetamide-medium containing nitrate as sole nitrogen source. The amdS$^-$-phenotype of the recombinants was confirmed by lack of growth of the recombinants on plates containing acetamide as sole nitrogen source. Typically, 0.1–2% of the original number of plated spores exhibited the desired phenotype.

Southern analysis on chromosomal DNA form several fluoracetamide resistant strains confirmed that the amdS selection marker gene was removed from the *P. chrysogenum* genome.

EXAMPLE 7

Test of the amdS-Minus Phenotype of the Yeast *Kluyveromyces lactis*

A prerequisite for the use of the amdS selection system in *K. lactis* is that this yeast does not contain any acetamidase activity. To test this we have plated the *K. lactis* strains CBS 683 and CBS 2360 on the following 3 different solid media:
I Yeast Carbon Base (YCB, Difco), containing all the essential nutritives and vitamins except a nitrogen-source.
II YCB supplemented with 5 mM acetamide.
III YCB supplemented with 0.1% (w/v) NH$_4$(SO$_4$)$_2$.
All 3 media contained 1.2% (w/v) Oxoid agar (Agar No. 1) and 30 mM Sodium Phosphate buffer at pH 7.0. Difco YCB was used at 1.17% (w/v).

Full grown *K. lactis* colonies were only observed on medium III, containing ammonium as nitrogen source. In plates without nitrogen-source or with acetamide as sole nitrogen-source no growth or, occasionally slight background growth was observed, which is most likely caused by trace amounts of nitrogen contaminating the agar or other medium components. We conclude that both *K. lactis* strains lack sufficient acetamidase activity to sustain growth on acetamide as sole nitrogen source. This should allow for the *A. nidulans* amdS gene to be used as selection marker in the yeast *K. lactis*.

EXAMPLE 8

Construction of Plasmids for Use of the amdS Gene in Yeasts Construction of pGBamdS1

We have previously used pGBHSA20 for the expression of human serum albumin (HSA) in *K. lactis* (Swinkels et al. 1993, Antonie van Leeuwenhoek 64, 187–201). In pGBHSA20 the HSA cDNA is driven from the *K. lactis* LAC4 promoter (FIG. 34 for the physical map of the plasmid pGBHSA20). At the 3'-end the HSA cDNA is flanked by LAC4 terminator sequences. For selection of transformants pGBHSA20 contains the Tn5 phosphotransferase gene which confers resistance to the antibiotic G418 (Geneticin, BRL) (Reiss et al. (1984) EMBO J. 3, 3317–3322) driven by the *S. cerevisiae* ADH1 promoter (Bennetzen and Hall (1982) J. Biol. Chem. 257, 3018–3025). In the unique SstII site of the LAC4 promoter

```
5'-GCTCTAGAGCGCGCTTATCAGCTTCCAGTTCTTCCCAGGATTGAGGCATTTTTAATGTTACTTCTCTTGC-3'
``` pGBHSA20 contains the *E. coli* vector pTZ19R which is used for amplification in, *E. coli*. Prior to transformation to *K. lactis* the pTZ19R sequences are removed from pGBHSA20 by SstII digestion and agarose gel purification. Transformation of pGBHSA20 linearized in the SstII site of the LAC4 promoter to *K. lactis*, results in integration into the genomic LAC4 promoter by homologous recombination. pGBamdS1 is derived from pGBHSA20 by substitution of the HSA cDNA for the amdS cDNA from pamdS1. Using PCR, SalI sites were introduced at the 5' and 3' ends of the amdS cDNA. In this PCR pamdS1 was used as template and oligo's AB3514 (SEQ ID NO:26) and AB3515 (SEQ ID NO:27) were used as primers.
Oligo AB3514 (SEQ ID NO:26):

5'-CTGCGAATTCGTCGACATGCCTCAATCCTGGG-3'

(an 5' end amdS-specific sequence with the introduced SalI site)
Oligo AB3515 (SEQ ID NO:27):

5'-GGCAGTCTAGAGTCGACCTATGGAGTCACCACATTTC-3'

(an 3' end amdS-specific sequence with the introduced SalI site).

The PCR fragment thus obtained was digested with SalI and cloned into the SalI/XhoI sites of pGBHSA20. Several clones were obtained containing either of the 2 possible orientations of the amdS cDNA as judged by restriction analysis. One of the clones with the amdS cDNA in the correct orientation is pGBamdS1, the physical map of which is shown in FIG. 34.

Construction of pGBamdS3

By heterologous hybridization using a probe derived from the *S. cerevisiae* elongation factor 1-α gene (EF1-α; Nagata et al. (1984) EMBO J. 3, 1825–1830), we have isolated a genomic clone containing the *K. lactis* homologue of the EF1-α gene, which we call KlEF1. In this example we have used a 813 bp fragment containing the KlEF1 promoter to express the amdS cDNA in *K. lactis*. Using oligonucleotides (3' KlEF1-specific promoter sequence fused to the 5'-sequences of the amdS cDNA with the restriction sites BssH2 and additional site XbaI).

The PCR was performed using standard conditions and the PCR-fragment obtained was digested with EcoRI and XbaI and subcloned into EcoRI/XbaI digested pTZ19R. The physical map of the resulting plasmid pTZKlEF1 is shown in FIG. 35. The remaining part of the amdS cDNA as well as part of the LAC4 terminator sequences were obtained from pGBamdS1 by digestion with BssH2 and SphI. This BssH2-SphI fragment was cloned into the BssH2 and SphI digested pTZKlEF1 and the resulting plasmid was designated pGBamdS2 (FIG. 35). For the final step in the construction of pGBamdS3, both pGBamdS2 and pTY75LAC4 (Das and Hollenberg (1982) Current Genetics 6, 123–128) were digested with SphI and HindIII. The 5.7 kb DNA fragment from pGBamdS2 and the 1.2 kb DNA fragment from pTY75LAC4, which contains the remaining LAC4 terminator sequences, were purified from agarose gels after fractionation and subsequently ligated and used to transform *E. coli*. The resulting expression vector, in which the amdS cDNA is driven from the *K. lactis* KlEF1 promoter, was, designated pGBamdS3 (FIG. 36).

Construction of pGBamdS5

Fusion of the *S. cerevisiae* alcohol dehydrogenase I (ADH1) promoter to the amdS cDNA was performed in a PCR using pGBHSA20 as template. One of the primers (AB3703; SEQ ID NO:31) contains sequences complimentary to the 3'-end of the ADH1-promoter sequence which are fused to sequences of the amdS cDNA. The other primer (AB3702; SEQ ID NO:30) contains the 5'-end of the ADH1 promoter:
Oligo AB3702 (SEQ ID NO:30):

5'-CTGCGAATTCGTCGACACTAGTGGTAC-CATCCTTTTGTTGTTTCCGGGTG-3'

(a 5' ADH1-specific promoter sequence with the additional restriction sites EcoRI, SalI, SpeI and KpnI at the 5' end of the promoter).
Oligo AB3703 (SEQ ID NO:31):

```
5'-GCTCTAGAGCGCGCTTATCAGCGGCCAGTTCTTCCCAGGATTGAGGCATTGTATATGAGATAGTTGATTG-3'
```

AB3701 (SEQ ID NO:28) and AB3700 (SEQ ID NO:29), this fragment was amplified in a PCR using genomic DNA from *K. lactis* strain CBS 683 as template. AB3700 (SEQ ID NO:29) is designed such that it contains 21 nucleotides of the KlEF promoter and 38 nucleotides upstream the ATG initiation codon of the amdS gene. The sequence of AB3701 (SEQ ID NO:28) and AB3700 (SEQ ID NO:29) is as shown:
Oligo AB3701 (SEQ ID NO:28):

5'-CTGCGAATTCGTCGACACTAGTGGTAC-CATTATAGCCATAGGACAGCAAG 3'

(a 5' KlEF1-specific promoter sequence with the additional restriction sites EcoRI, SalI, SpeI and KpnI at the 5' end of the promoter)
Oligo AB3700 (SEQ ID NO:29):

(a 3' ADH1-specific promoter sequence fused to the 5' amdS sequence with additional restriction sites BssH2 and XbaI).

The PCR reaction was performed using a "touchdown" protocol (Don et al., (1991) Nucleic Acids Res. 19, 4008). The reaction mixtures were subjected to 30 amplification cycles, while the annealing temperature was decreased 1° C. every two cycles, starting 55° C. down to a "touchdown" at 40° C., at which temperature 10 more cycles were carried out (cycles: 2' at 94° C., 2' annealing, 3' at 72° C.). The PCR-fragment obtained was digested with EcoRI and XbaI and subcloned into pTZ19R. The resulting plasmid pTZs.c.ADH1 is shown in FIG. 37. pTZs.c.ADH1 and pGBamdS3 were digested with KpnI and BssH2. The 6.8 kb fragment from pGBamdS3 and the 750 bp fragment from pTZs.c.ADH1 were purified by gel electrophoresis, ligated and used to transform E. coli JM109. The resulting expression vector was designated pGBamdS5 (FIG. 37).

Construction of pGBamdS6

Plasmid pGBamdS3 contains the amdS cDNA under control of the KlEF1 promoter and flanked at the 3' end by 1.5 kb of LAC4 terminator sequences (FIG. 36). pGBamdS6 is constructed by cloning a fragment which contains a fusion of the LAC4 promoter and terminator sequences upstream of the amdS expression-cassette in pGBamdS3 (FIG. 38). In order to fuse the LAC4 promoter and terminator sequences we have first constructed pPTLAC4 (FIG. 39). Using a PCR, additional restriction sites are introduced at the 5' and 3' end of a 600 bp LAC4 terminator fragment. In the PCR K. lactis CBS 683 chromosomal DNA was used as template and oligonucleotides AB3704 (SEQ ID NO:32) and AB3705 (SEQ ID NO:33) were used as primers:

Oligo AB3704 (SEQ ID NO:32):

5'-GCTCTAGAAGTCGACACTAGTCTGCTACGTACTCGAGAATTTATACTTAGATAAG-3'

(a LAC4 terminator-specific sequence starting at the LAC4 stop codon with the additional restriction sites XbaI, SalI, SpeI, SnaBI and XhoI).

Oligo AB3705 (SEQ ID NO:33):

5'-TGCTCTAGATCTCAAGCCACAATTC-3'

(3' LAC4 terminator-specific sequence with the additional restriction site XbaI).

The PCR was performed using standard conditions and the resulting DNA fragment was digested with XbaI and subcloned into the XbaI site of pTZ19R to give pTLAC4 (FIG. 39). The LAC4 promoter sequence is obtained by digestion of pKS105 van den Berg et al. (1990) Bio/Technology 8, 135–139) with XbaI and SnaBI. The XbaI-SnaBI LAC4 promoter fragment was cloned into the SpeI/SnaBI sites of pTLAC4 and designated pPTLAC4 (FIG. 39). For the final step in the construction of pGBamdS6, the plasmid pPTLAC4 was digested with XbaI. The 4.1 kb DNA fragment from pPTLAC4 was purified by gel-electrophoresis and cloned into SpeI site of pGBamdS3. The obtained gene-replacement vector was designated pGBamdS6 (FIG. 38)

Construction of pGBamdS8 pGBamdS7 was constructed by cloning a fragment, which contains part of the LAC4 promoter as well as the chymosin expression-cassette, in between the LAC4 promoter and terminator sequences as present in pGBamdS6 (FIG. 40). Plasmid pKS105 contains the prochymosin cDNA fused to the prepro-region of S. cerevisiae α-factor under control of the LAC4 promoter (van den Berg et al. (1990) Bio/Technology 8, 135–139). Using a PCR, additional restriction sites were introduced at the 5' and 3' end of the fusion LAC4 promoter and chymosin expression-cassette. In the PCR pKS105 DNA was used as template and oligonucleotides AB3965 (SEQ ID NO:34) and AB3966 (SEQ ID NO:35) were used as primers:

Oligo AB3965 (SEQ ID NO:34):

5'-CTGCTACGTAATGTTTTCATTGCTGTTTTAC-3'

(a LAC4 promoter-specific sequence starting at the restriction site SnaB1)

Oligo AB3966 (SEQ ID NO:35):

5'-CCGCCCAGTCTCGAGTCAGATGGCTTTGGCCAGCCCC-3'

(chymosin-specific sequence with the additional restriction site Xho1).

The PCR was performed using standard conditions and the obtained PCR fragment was digested with SnaB1 and Xho1. The plasmid pGBamdS6 was partially digested with XhoI and subsequently digested with SnaBI and the 10.9 kb DNA fragment was isolated and purified by gel-electrophoresis. The SnaB1-Xho1 fusion fragment LAC4 promoter/chymosin expression-cassette was cloned into the SnaB1/Xho1 sites of pGBamdS6. The resulting plasmid was designated pGBamdS7 (FIG. 40).

To destroy the HindIII site approximately 66 bp upstream the startcodon from the chymosin gene, pGBamdS7 was partially digested with HindIII and treated with the Klenow fragment of E. coli DNA polymerase I to generate blunt ends, subsequently ligated and transferred to E. coli for molecular cloning. The derived plasmid was designated pGBamdS8 and contains a LAC4 promoter fragment with a destroyed HindIII site.

EXAMPLE 9

Expression of the amdS cDNA from the LAC4 Promoter in the Yeast K. lactis

The expression vector, pGBamdS1, contains, apart from the amdS cDNA a second selection marker which confers resistance to the antibiotic G418. This allows to first select for transformants using G418 resistance which is a well established procedure (Sreekrishna et al. (1984) Gene 28, 73–81). The transformants obtained this way can subsequently be used to verify expression of the amdS cDNA and to optimize conditions for selection of the amdS$^+$ phenotype in K. lactis. Once these conditions have been established, direct selection for amdS$^+$ transformants can be performed, e.g. using expression cassettes without additional selection markers.

pGBamdS1 (FIG. 34) was linearized in the LAC4 promoter by SstII digestion. The pTZ19R sequences were removed by fractionation in and purification from agarose gels. 15 μg's of this DNA fragment were used to transform to the K. lactis strains CBS 2360 and CBS 683 as described by Ito H. et al. (1983) J. Bacteriol. 153, 163–168 with the modifications described under Experimental. The transformation plates were incubated at 30° C. for 3 days. G418-resistant transformants were obtained with both strains. Several independent transformants of both strains as well as the wild type strains were subsequently streaked onto plates containing different solid media (see Table 1). YEPD and YEPD/G418 have been described in Experimental. YCB, YCB/NH$_4$ and YCB/acetamide have been described in example 7 as media I, II and III, respectively. YNB-lac/NH$_4$ and YNB-lac/acetamide contain 0.17% (w/v) Yeast Nitrogen Base w/o Amino Acids and Ammonium Sulfate (Difco) supplemented with 1% (w/v) lactose, 30 mM Sodium Phosphate buffer at pH 7.0 and either 0.1% (w/v) NH4 (SO4) 2 or 5 mM acetamide, respectively.

The amdS$^+$ phenotype of the CBS 683/pGBamdS1 transformants was obvious on YCB/acetamide (see Table 1).

However, the CBS 2360 transformants containing the same expression vector did not show any growth on YCB/acetamide. We reasoned that this might be due to the lack of induction of the LAC4 promoter driving the amdS cDNA in the absence of lactose or galactose as carbon-source dependent differences in the regulation of the LAC4 promoter between different *K. lactis* strains have been described (Breunig (1989) Mol. Gen. Genet. 216, 422–427). Table 1 shows that this is indeed the case, on medium containing lactose as sole carbon-source and acetamide as sole nitrogen source the CBS 2360 transformants were able to grow. We can therefore conclude that, depending on the carbon-source used, these transformants sufficiently express the *A. nidulans* amdS cDNA in order to sustain growth of the yeast *K. lactis* on acetamide as sole nitrogen-source.

Southern analyses were performed to verify whether integration in the LAC4 promoter had occurred. High molecular weight DNA of several CBS 2360 and CBS 683 transformants was isolated, digested with HindIII and subsequently fractionated by electrophoresis on a 0.7% agarose gel. After transfer to nitrocellulose, hybridization was performed according to standard procedures. As probe a $^{32}$P-labelled approximately 1.5 kb SacII/HindIII LAC4 promoter fragment isolated from plasmid pGBHSA20 (FIG. 34) was used. We identified CBS 683 and CBS 2360 transformants containing a single pGBamdS1 expression cassette integrated in the LAC4 locus, one example of each is shown in FIG. 41 and is designated KAM-1 and KAM-2, respectively. Single copy integration of pGBamdS1 in the LAC4 promoter produces two new HindIII fragments of 4.2 and 8.6 kb, both of which are present in transformants KAM-1 and KAM-2. Since CBS 683 contains two LAC4 loci and pGBamdS1 has integrated in only one of them in KAM-1, the digest of KAM-1 also shows the 5.6 kb HindIII fragment derived from the second undisturbed LAC4 locus.

TABLE 1

Growth of *K. lactis* CBS 683 and CBS 2360 wild type and pGBamdS1 transformants on solid media containing different nitrogen- and/or carbon-sources.

| strain | CBS 683 | | CBS 2360 | |
| --- | --- | --- | --- | --- |
| transforming DNA | none | pGBamdS1 | none | pGBamdS1 |
| YEPD | + | + | + | + |
| YEPD-G418 | − | + | − | + |
| YCB | − | − | − | − |
| YCB/NH$_4$ | + | + | + | + |
| YCB/acetamide | − | + | − | − |
| YNB-lac/NH$_4$ | + | + | + | + |
| YNB-lac/acetamide | − | + | − | + |

EXAMPLE 10

Direct Selection of *K. lactis* CBS 683 and CBS 2360 Transformants Using Acetamide as Sole Nitrogen-Source SstII linearized pGBamdS1 (15 µg) was transformed into *K. lactis* CBS 683 and CBS 2360 using the transformation procedure as described by Ito H. et al. ((1983). J. Bact. 153, 163–168.) with the following modifications:

*K. lactis* cultures were harvested for transformation at OD$_{610}$=0.5–1.0.

After the 5 minutes heatshock of the DNA-cell suspension, the phenotypic expression prior to plating was performed for 150–180 minutes at 30° C. in volumes of 1 ml. Different media were used for both strains. For CBS 683 a YEPD/YNB solution (1*YNB (Yeast Nitrogen Base, Difco), 1% bacto-peptone, 1% yeast extract and 2% glucose) or YNB-glu (1*YNB (Yeast Nitrogen Base w/o Amino Acids and Ammonium Sulphate, Difco) supplemented with 1% (w/v) glucose and 30mM Sodium Phosphate buffer at pH 7.0) were used. After this incubation the cells were centrifuged at 2000 g at room temperature for 5 minutes and subsequently plated on YCB/acetamide (see example 7). For CBS 2360, YNB-lac (1*YNB (Yeast Nitrogen Base w/o Amino Acids and Ammonium Sulphate, Difco) supplemented with 1% (w/v) lactose and 30 mM Sodium Phosphate buffer at pH 7.0) was used. After this incubation the cells were centrifuged at 2000 g at room temperature for 5 minutes and subsequently plated on YNB-lac/acetamide (see example 9).

Figure 42:
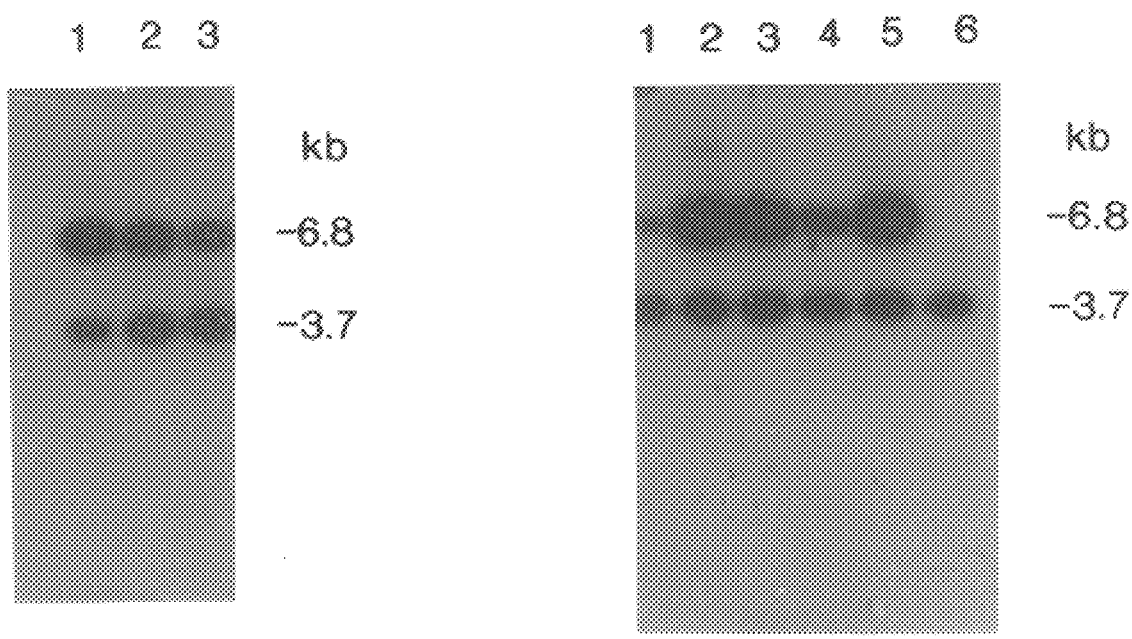

Growth was performed at 30° C. for 3 days. amdS$^+$ transformants were obtained for both strains. The transformation frequencies found were comparable to that found when using the G418 selection. The correct identity of the transformants was confirmed by subsequent plating on YEPD-plates containing G418 and by Southern analysis.

pGBamdS3 (FIG. 36), in which the amdS cDNA is driven from the KlEF1 promoter, was linearized in the LAC4 terminator by digestion with XhoI and 15 µg of the gel-isolated fragment was subsequently transformed into the *K. lactis* strain CBS 683 using direct selection on YCB/acetamide plates as described above for the transformation of pGBamdS1 into CBS 683. Some of the transformants obtained were analyzed by Southern blotting. High molecular weight DNA was isolated, digested with BamHI and subsequently separated by electrophoresis on a 0.7% agarose gel. Following transfer to nitrocellulose, hybridization was performed according to standard procedures. As probe the $^{32}$P-labelled 1.2 kb SphI/HindIII LAC4 terminator fragment isolated from plasmid pTY75LAC4 (described in Example 8) was used. The results of several CBS 683 transformants, containing the pGBamdS3 plasmid and from several transformants containing the pGBamdS5 plasmid are shown in FIG. 42A and 42B respectively. The reference strain CBS 683 is shown in FIG. 42B. In the CBS 683 transformants an additional 6.8 kb sized hybridizing fragment is present besides the 3.7 kb hybridizing fragment of the intact LAC4 terminator. This implicates a correct integration of the plasmids into the LAC4 terminator region.

In all of these transformants pGBamdS3 was integrated in one or more copies into the LAC4 terminator (the intensity of the 6.8 kb hybridizing fragment is an indication for the number of integrated copies of the vector). We conclude that also the constitutive KlEF1 promoter can drive the amdS cDNA for use as selection marker. Similar results were obtained with pGBamdS5 (FIG. 37), in which the amdS cDNA is driven from the *S. cerevisiae* ADH1 promoter.

EXAMPLE 11

Transformation of *S. cerevisiae* with pGBamdS5 by Direct Selection on Acetamide In this example we have tested whether the amdS cDNA can also be used as selection marker in other yeasts, e.g. *S. cerevisiae*. We have first established the amdS phenotype of *S. cerevisiae* strain D237-10B and its ability to use ammonium as sole nitrogen-source, using the same media and procedures as we have described for *K. lactis* in example 7. As observed in the case of *K. lactis*, full grown *S. cerevisiae* colonies were only observed on the plates containing ammonium as nitrogen source. In plates without nitrogen-source or with acetamide as sole nitrogen-source no growth or, occasionally a slight background growth was observed. Plasmid pGBamdS5 was linearized in the ADH1 promoter by partial digestion with SphI. The *S. cerevisiae* strain D273-10B (ATCC 25657) was transformed with 15 μg of gel-isolated linearized pGBamdS5 fragment, using transformation procedures as described in example 10 for the transformation of pGBamdS1 to *K. lactis* CBS 683. After transformation the cells were plated onto YCB/acetamide plates (see Example 9) and allowed to grow at 30° C. for 3 days. Several amdS$^+$ transformants were obtained with in this transformation. Subsequent Southern analysis of some of the amdS transformants confirmed that the amdS cDNA was stably integrated into the *S. cerevisiae* genome.

High molecular weight DNA was isolated and digested with BamHI, subsequently separated by electrophoresis on a 0.7% agarose gel and blotted onto nitrocellulose. As probe the $^{32}$P labelled 750 bp EcoRV amdS fragment was used isolated from pGBamdS1. The results of several D273-10B/pGBamdS5 transformants as well as the reference strain D273-10B (ATCC 25657) are shown in FIG. 43. Two hybridizing fragments are present in the D273-10B transformants respectively, a 6.6 kb fragment that represents the multicopy fragment and a hybridizing fragment of unknown size that represents the flanking. The reference strain D273-10B (ATCC 25657) as expected does not show any hybridizing fragment.

EXAMPLE 12

Removal of the amdS-Marker from *K. lactis* and *S. cerevisiae* amdS$^+$ Transformants Using Fluoracetamide Counter-Selection In the above described examples the amdS containing expression cassettes are integrated by a single cross-over homologous recombination in the *K. lactis* and *S. cerevisiae* genomes. This means that the amdS cDNA is flanked by direct repeats in the genomes of these amdS yeast transformants. Consequently, the amdS cDNA will be deleted in a small fraction of the transformant population by intra-chromosomal mitotic recombination events occurring at low frequency between the direct repeats flanking the cDNA. It should be possible to select for these events using media containing fluoracetamide, a compound which is toxic for amdS$^+$ cells but not for amdS$^-$ cells as has been shown for *A. nidulans* by Hynes and Pateman ((1970) Mol. Gen. Genet. 108, 107–116). In amdS$^+$ cells fluoracetamide is converted into ammonium and fluoracetate, the latter being toxic when activated by the enzyme acetyl-CoA-synthetase. Prerequisites for the fluoracetamide counter-selection to also work on amdS$^+$ yeasts are therefore 1) fluoracetamide should not be toxic for amdS$^-$ yeasts, 2) the yeast cellwall and plasmamembrane should be permeable to fluoracetamide and 3) the enzyme acetyl-CoA-synthetase should be active. To test this we have used a *K. lactis* CBS 683 transformant containing a single copy of pGBamdS1 integrated in the LAC4 promoter, designated KAM-1 and a *S. cerevisiae* D273-10B transformant containing a single copy of pGBamdS5 integrated in the ADH1 promoter, designated SAM-1. Both KAM-1 and SAM-1 were subjected to at least 3 rounds of genetic purification on selective medium (YCB/acetamide) to exclude contamination with the amdS$^-$ parental strains. KAM-1 and SAM-1 were each plated at a density of approximately 103 CFU per plate onto YCB/NH$_4$ supplemented with 10 mM fluoracetamide. For both KAM-1 and SAM-1, 5 to 20 fluoracetamide resistant colonies appeared after 3 to 6 days at 30° C. Southern analysis on chromosomal DNA from several independent KAM-1 and SAM-1 derived amdS$^-$ colonies confirmed that the amdS cDNA was correctly removed from the *K. lactis* and *S. cerevisiae* genomes by homologous recombination between the flanking direct repeats (FIG. 41). In fact, in one of the KAM-1 amdS recombinants the crossover-point of the recombination was located between a polymorphic HindIII site and the amdS cDNA. This polymorphic HindIII is present 92 bp upstream of the LAC4 reading frame in the LAC4 promoter of pgBamdS1, however, this site is not present in the CBS 683 LAC4 promoter. The recombination event has left the HindIII site in the genome of this particular KAM-1 recombinant which could otherwise not be discriminated from the parent strain CBS 683 (see the extra 4.2 kb fragment in FIG. 41, lane 6). This KAM-1 recombinant therefore excludes the possibility the we would have isolated CBS 683 contaminants in stead of KAM-1 amdS$^-$ recombinants. We conclude from the above that the amdS cDNA can be removed from yeast genomes when flanked by direct repeats using fluoracetamide counter-selection. In the present example the amdS$^-$ *K. lactis* and *S. cerevisiae* recombinants occur at a frequency of about 0.1%.

We have noted that for some yeast strains efficient counter-selection on fluoracetamide cannot be performed on YCB/NH$_4$, probably due to strong carbon-catabolite repression of the acetyl-CoA-synthetase. In those instances we have successfully used YNB-galactose/NH$_4$ (this medium is identical to YNB-lac/NH$_4$ described in example 9 but contains 1% galactose in stead of 1% lactose) supplemented with 10 mM fluoracetamide for counter-selection.

EXAMPLE 13

Marker Gene Free Deletion of a *K. lactis* Gene Using the amdS-Marker

A frequently used technique for the manipulation of yeast genomes is "one-step gene disruption", a method which allows to disrupt (or modify) genes in a single transformation step (Rothstein et al. (1983) Methods Enzymol. 101, 202–211). In this method a transforming plasmid with a copy of a target gene disrupted by a yeast selectable marker integrates into the yeast genome via a double cross-over homologous recombination, resulting in the replacement of the wild-type target gene by the disrupted copy. Combination of "one-step gene disruption" and the fluoracetamide counter-selection of amdS$^+$-yeast-transformants as we have described in Example 12, should enable the deletion of genes from yeast genomes without leaving selectable markers. In this example we have used this combination to delete the LAC4 gene from the *K. lactis* CBS 2360 genome. For one-step gene transplacement of the *K. lactis* LAC4 gene pGBamdS6 (FIG. 38) was constructed, which contains the amdS expression-cassette flanked by LAC4 promoter and terminator sequences. An additional LAC4 terminator fragment is present directly upstream of the amdS expression-cassette such that the amdS expression-cassette is flanked by direct repeats which will allow the excision of the amdS sequences from the *K. lactis* genome by intrachromosomal recombination between these direct repeats. Plasmid pGBamdS6 was digested with SpeI and HindIII and a 6.6 kb DNA fragment was isolated after gel electrophoresis. This SpeI-HindIII fragment, containing the gene replacement vector, was used to transform *K. lactis* CBS 2360 using transformation procedures described in Example 10. amdS$^+$ transformants were plated onto on YEPD plates containing 0.008% X-gal (5-bromo-4-chloro-3-indolyl β-D- galactopyranoside) in order to screen for transformants with a transplaced LAC4 gene.

The amdS+ transformants were analyzed on Southern blot. High molecular weight DNA was isolated, digested with HindIII, subsequently separated by electrophoresis on a 0.7% agarose gel and blotted onto nitrocellulose. As probe a $^{32}$P-labelled 600 bp XbaI LAC4 terminator fragment isolated from plasmid pPTLAC4 (described in example 8) was used. The results of an amdS+ CBS 2360 transformant with a transplaced LAC4 gene as well as the reference strain CBS 2360 are shown in FIG. 44. In case of the amdS+ CBS 2360 transformant, a 7.4 kb hybridizing fragment is present that implicates a correctly transplaced LAC4 gene. The reference strain CBS 2360 shows a 2.0 kb hybridizing fragment that represents the intact LAC4 locus.

Subsequent fluoracetamide counter-selection of these amdS+ transformants as described in Example 12, yielded recombinants with an amdS− phenotype. Southern analysis was performed on the chromosomal DNA of the amdS− recombinants. High molecular weight DNA was isolated, digested with HindIII, subsequently separated on a 0.7% agarose gel and blotted onto nitrocellulose. The same $^{32}$P-labelled probed as described above was used. The results of the amdS− CBS 2360 recombinants are shown in FIG. 44. In case of the amdS− recombinants, a 5.4 kb hybridizing fragment is present, which confirmed the absence of the LAC4 gene as well as the correct removal of the amdS marker from the yeast genome. The absence of the amdS marker from these K. lactis LAC4− strains offers the possibility to reuse the amdS marker for additional deletions and/or modifications of genes.

EXAMPLE 14

Marker Gene Free Insertion of a Gene Into the K. lactis Genome Using the amdS Marker For the marker gene free insertion of genes into the yeast genome we have used the chymosin cDNA as a model-gene. In this example we have inserted the chymosin cDNA at the K. lactis LAC4 locus while replacing the LAC4 gene and without leaving a selection marker. The principle of marker-free gene insertion is the same as that for marker-free deletion of genes as described in example 13 except that in this case the transplacement vector pGBamdS8 contains a gene of interest, the chymosin cDNA (FIG. 40). Plasmid pGBamdS8 was digested with SpeI and HindIII and the 8.0 kb DNA fragment was gel-isolated. 10 μg of this fragment was transformed to K. lactis CBS 2360 as described in Example 10. amdS+ transformants with a transplaced LAC4 gene and chymosin activity were obtained. Chymosin activity was measured as described (van den Berg et al. (1990) Bio/technology i, 135–139). By subsequent counter-selection of these transformants on fluoracetamide as described in example 12 recombinants were isolated with an amdS− phenotype but which still produced chymosin. Southern analysis of the chromosomal DNA of the amdS−, Chymosin+ recombinants confirmed the replacement of the LAC4 gene by the chymosin cDNA as well as the correct removal of the amdS marker from the K. lactis genome. The amdS−/chymosin+ phenotype of these recombinants was also confirmed by lack of growth on YCB/acetamide plates and by the presence of chymosin activity (see above). The amdS− phenotype of these recombinants allows further manipulation of these strains using the amdS marker, e.g. integration of additional copies of the chymosin expression-cassette and/or deletion of K. lactis genes as described in example 13.

EXAMPLE 15

Test of the amdS-Minus Phenotype of Bacilli and E. coli

A prerequisite for the use of the amdS selection system in Bacilli is that these Gram-positive bacteria do not contain any acetamidase activity. In order to test this we have plated the B. subtilis strain BS-154 (CBS 363.94) on a minimal Bacillus medium containing all the essential nutritives and vitamins except a nitrogen-source (28.7 mM $K_2HPO_4$, 22 mM $KH_2PO_4$, 1.7 mM sodium citrate, 0.4 mM $MgSO_4$, 0.75 μM $MnSO_4$, 0.5% (w/v) glucose and 1.5% agar. No growth was observed on this medium as such or when supplemented with 20 mM acetamide as nitrogen-source. Growth was only observed in the case that the minimal medium was supplemented with either 20 mM $(NH_4)_2SO_4$ or 20 mM $KNO_3$ as nitrogen source. We conclude that Bacillus BS-154 (CBS 363.94) lacks sufficient acetamidase activity to sustain growth on acetamide as sole nitrogen source. This phenomenon should allow for the A. nidulans amdS gene to be used as selection marker in Gram-positive bacteria.

Similarly we have tested the lack of acetamidase activity in a Gram-negative bacterium, in this case E. coli, in order to establish whether the A. nidulans amdS gene can also be used as selection marker in these micro-organisms. In this case we used M9 minimal medium (Sambrook et al. (1989) "Molecular Cloning: a laboratory manual", Cold Spring Harbour Laboratories, Cold Spring Harbour, N.Y.) supplemented with 0.02 μg (w/v) thiamine. Full grown colonies of E. coli JM109 were observed on when plated on M9 plates. No growth or only slight background growth was observed, however, when the $NH_4Cl$ was omitted from the M9 plates or replaced by 20 mM acetamide. We conclude that the E. coli JM109 strain lacks sufficient acetamidase activity to sustain growth on acetamide as sole nitrogen source. This should allow for the A. nidulans amdS gene to be also used as selection marker in Gram-negative bacteria.

EXAMPLE 16

Construction of amdS Expression-Vectors for Use in Bacteria

Construction of pGBamdS22

To express the A. nidulans amdS gene in different Bacilli species, we have cloned the amdS cDNA from pamdS-1 into the basic Bacillus expression vector pBHA-1 (European Patent Application 89201173.5; FIG. 45 for physical map). At the ATG initiation-codon of the amdS cDNA gene an NdeI site was introduced in pamdS-1 using oligonucleotides AB3825 (SEQ ID NO:36) and AB3826 (SEQ ID NO:37) with the following sequences:

Oligo AB3825 (SEQ ID NO:36):

5'-CGCGCTTATCAGCGGCCAGTTCTTC-
CCAGGATTGAGGCATATGT-3'

Oligo AB3826 (SEQ ID NO:37):

5'-CTAGACATATGCCTCAATCCTGGGAA-
GAACTGGCCGCTGATAAG-3'

Annealing of these oligonucleotides was carried out using standard procedures. The resulting double stranded DNA fragment was ligated into BssHII/XbaI digested pamdS-1 and transferred to E. coli. From one of the transformants pGBamdS21 was isolated and characterized by restriction-enzyme analysis (FIG. 47). pGBamdS21 was digested with KpnI and HindIII and the amdS cDNA containing fragment was cloned into pBHA-1 digested with KpnI and HindIII. The resulting plasmid was designated pGBamdS22 (FIG. 48).

Construction of pGBamdS25

To demonstrate site specific integration of a desired DNA sequence into the B. licheniformis genome using amdS as selection marker, the amdS cDNA was cloned in the expression/integration-vector pLNF (FIG. 46). This vector containing the 5' and 3' non-coding sequences of the *B. licheniformis* amylase gene enables site specific integration at the corresponding chromosomal amylase locus. pGBamdS21 (described above, FIG. 47) was digested with NdeI and PvuII and the amdS cDNA containing fragment was ligated with pLNF digested with NdeI and ScaI. The ligation mixture was transformed to *B. subtilis* BS-154 (CBS 363.94). Transformants were selected on minimal medium supplemented with 20 μg/ml neomycin. From one of the transformants, designated BAA-101, the plasmid pGBamdS25 (FIG. 50) was isolated.

Construction of pGBamdS41

For the expression of the *A. nidulans* amdS cDNA in *E. coli* we have used pTZ18R/N, a derivative of pTZ18R which is described in the European Patent Application 0 340 878 A1 pTZ18R/N differs from pTZ18R in that an NdeI site was created at the ATG start-codon of the lacZ reading frame in pTZ18R using in vitro site directed mutagenesis. pGBamdS21 was digested with NdeI and HindIII and the gel-isolated fragment containing the amdS cDNA was ligated into pTZ18R/N digested with NdeI and HindIII. This ligation mixture was used to transform *E. coli* JM109 and from one of the transformants pGBamdS41 (FIG. 51) was isolated.

EXAMPLE 17

Transformation of Bacilli Using the amdS Gene as Selection Marker

In order to delete the *E. coli* sequences from pGBamdS22 and to place the "hpa2"-promoter immediately upstream of the amdS cDNA, pGBamdS22 was digested with NdeI, recircularized by ligation and used to transform *B. subtilis* BS-154 (CBS 363.94). Transformants were selected on acetamide minimal plates and checked for neomycin resistance. From one of these transformants expression-vector pGBamdS23 (FIG. 49) was isolated and characterized by restriction enzyme analysis. These results show that 1) the *A. nidulans* amdS cDNA under the control of a Bacillus promoter sequence is expressed well and 2) that the amdS gene can be used as a selection marker in the transformation of Bacilli.

*B. licheniformis* T5 (CBS 470.83) was transformed with vector pGBamdS25. Transformation was performed as described in Experimental and amdS⁻ transformants were obtained by direct selection on modified protoplast regeneration plates supplemented with 20 mM acetamide as sole nitrogen source (described in Experimental). The presence of pGBamdS25 in the transformants was confirmed by their neomycin resistance phenotype as well as the fact that the plasmid could be reisolated from the transformants. One of these transformants designated BAA-103 was used to achieve integration of plasmid pGBamdS25 into the *B. licheniformis* genome targeted at the amylase locus. Plasmid integration was performed by growing transformants at 50° C. on minimal medium agar containing acetamide as sole nitrogen source. Several colonies were transferred repeatedly (2 to 3 times) to fresh plates followed by incubation at 50° C. Isolated colonies were tested for their ability to grow on acetamide as sole nitrogen source and for resistance to neomycin at 1 μg/ml. The absence of autonomously replicating plasmid DNA was established by re-transformation of DNA isolated from the integrants to the host strain. No neomycin resistant colonies could be obtained.

This result is a clear evidence that the amdS gene is a suitable marker to select Bacillus species containing a single amdS gene copy.

EXAMPLE 18

Transformation of *E. coli* Using the amdS Gene as Selection Marker

*E. coli* JM109 was transformed with the vector pGBamdS41 using standard procedures. Selections were performed on either M9 plates supplemented with 0.02 μg/ml thiamine and 50 μg/ml ampicillin or M9 plates without ammonium but supplemented with 20 mM acetamide, 0.02 μg/ml thiamine and 0.05 mm IPTG. Several amdS⁺/ampicillin resistant transformants were obtained from which pGBamdS41 could be reisolated. The transformation frequencies using selection on ampicillin or acetamide were comparable. This demonstrates that the *A. nidulans* amdS gene is functional as selection marker for the transformation of Gram-negative bacteria as well.

EXAMPLE 19

Fluoracetamide Counter-Selection of amdS⁺ Bacterial Transformants

Counter-selection of bacterial amdS⁺ transformants using fluoracetamide requires the activity of the enzyme acetyl-CoA synthetase for the conversion of fluoracetate to fluoracetyl-CoA. To avoid catabolite repression of acetyl-CoA synthase, as has been observed in *E. coli* (Brown et al., 1977), bacterial amdS⁺ transformants or single copy integrants were grown on defined media containing $NH_4Cl$ as nitrogen source and acetate as carbon and energy source.

Many organisms including *B. subtilis* (Freese, E. and Fortnagel, P. (1969) J. Bacteriol 90, 745–756) lack a functional glyoxylate shunt and therefore metabolize acetate only when the medium is supplemented with a source of TCA cycle intermediates, such as glutamate or succinate. Bacillus amdS⁺ strains were grown on TSS medium with 0.01% glutamate and 50 mM acetate as described by Grundy, F. J. et. al. (1993) Molecular Microbiology 10, 259–271. To this medium solidified with agar, fluoracetamide was added in concentrations ranging from 1 to 50 mM. *B. subtilis* BAA-101 or *B. licheniformis* BAA-103 (single copy integrant) were plated at a density of $10^2$ cells per plate. At a certain fluoracetamide concentration only a few colonies appeared. The absence of pGBamdS25 in these colonies was demonstrated by plasmid and chromosomal DNA analysis, sensitivity towards neomycin, and inability to grow on acetamide as sole nitrogen-source. Counter-selection of BAA-103 in some cases led to the loss of the amylase gene as indicated by activity assays and Southern blots. This shows that fluoracetamide counter-selection can be used to select amdS⁻ cells from a population containing a majority of amdS⁺ Bacillus cells and the simultaneous deletion of a specific target gene.

Similarly we have used minimal medium #132 as described by Vanderwinkel E. and De Vlieghere M., European J. Biochem, 5 (1968) 81–90 supplemented with fluoracetamide in concentrations ranging from 1 to 50 mM and 0.05 mM IPTG to select amdS⁻ *E. coli* JM109 cells from a population of pGBamdS41 transformants. Cells were plated at a density of $10^2$ cells per plate. At a certain fluoracetamide concentration only a few colonies appeared. The absence of pGBamdS41 from the fluoracetamide selected colonies was confirmed by isolation of DNA, sensitivity toward ampicillin and inability to grow on acetamide as sole nitrogen-source. This demonstrates that the fluoracetamide counter-selection is can be used to select amdS⁻ cells from a population containing a majority of amdS⁺ *E. coli* cells.

We claim:

1. A recombinant yeast strain wherein said recombinant yeast strain has been transformed with a first DNA molecule comprising a recombinant expression system comprising an Aspergillis acetamidase gene operably linked to one or more expression control sequences and functionally expressed resulting in acetamidase activity.

2. The recombinant yeast strain of claim 1, wherein said recombinant yeast strain has been transformed with a second DNA molecule that encodes a protein, wherein said protein is selected from the group consisting of: a chymosin, a phytase, a xylanase, a lipase, an amylase, a protease, and a β-galactosidase.

3. The recombinant yeast strain of claim 1, wherein said yeast is selected from the group consisting of Kluyveromyces and Saccharomyces.

4. The recombinant yeast strain of claim 3, wherein said acetamidase gene is integrated into the chromosome of said yeast strain.

5. The recombinant yeast strain of claim 4, wherein said recombinant yeast strain has been transformed with a second DNA molecule that encodes a protein.

6. The recombinant yeast strain of claim 5, wherein second DNA molecule contains a sequence encoding a chymosin, a phytase, a xylanase, a lipase, an amylase, a protease, or a β-galactosidase.

7. The recombinant yeast strain of claim 3, wherein said recombinant yeast strain has been transformed with a second DNA molecule that encodes a protein.

8. The recombinant yeast strain of claim 7, wherein said second DNA molecule contains a sequence encoding a chymosin, a phytase, a xylanase, a lipase, an amylase, a protease, or a β-galactosidase.

9. The recombinant yeast strain of claim 1, wherein said acetamidase gene is integrated into the chromosome of said yeast strain.

10. The recombinant yeast strain of claim 9, wherein said recombinant yeast strain has been transformed with a second DNA molecule that encodes a protein.

11. The recombinant yeast strain of claim 10, wherein said second DNA molecule contains a sequence encoding a chymosin, a phytase, a xylanase, a lipase, an amylase, a protease, or a β-galactosidase.

12. The recombinant yeast strain of claim 1, wherein said recombinant yeast strain has been transformed with a second DNA molecule that encodes a protein.

13. The recombinant yeast strain of claim 12, wherein said second DNA molecule contains a sequence encoding a chymosin, a phytase, a xylanase, a lipase, an amylase, a protease, or a β-galactosidase.

14. A recombinant bacterial host strain, wherein said recombinant bacterial host strain has been transformed with a first DNA molecule comprising a recombinant expression system comprising an Aspergillus acetamidase gene operably linked to one or more expression control sequences and functionally expressed resulting in acetamidase activity.

15. The recombinant bacterial host strain of claim 14, wherein said recombinant bacterial host strain is selected from the group consisting of: Gram-positive bacteria and Gram-negative bacteria.

16. The recombinant bacterial host strain of claim 15, wherein said recombinant bacterial host strain has been transformed with a second DNA molecule that encodes a protein.

17. The recombinant bacterial host strain of claim 16, wherein said second DNA molecule contains a sequence encoding a chymosin, a phytase, a xylanase, a lipase, an amylase, a protease, or a β-galactosidase.

18. The recombinant bacterial host strain of claim 15, wherein said recombinant bacterial host strain is selected from the group consisting of: Bacillus species and Escherichia species.

19. The recombinant bacterial host strain of claim 18, wherein said recombinant bacterial host strain has been transformed with a second DNA molecule that encodes a protein.

20. The recombinant bacterial host strain of claim 19, wherein said second DNA molecule contains a sequence encoding a chymosin, a phytase, a xylanase, a lipase, an amylase, a protease, or a β-galactosidase.

21. The recombinant bacterial host strain of claim 18, wherein said recombinant bacterial host strain is selected from the group consisting of: *Bacillus licheniformis; Bacillus subtilis;* and *Escherichia coli.*

22. The recombinant bacterial host strain of claim 21, wherein said recombinant bacterial host strain has been transformed with a second DNA molecule that encodes a protein.

23. The recombinant bacterial host strain of claim 22, wherein said second DNA molecule contains a sequence encoding a chymosin, a phytase, a xylanase, a lipase, an amylase, a protease, or a β-galactosidase.

24. The recombinant bacterial host strain of claim 14, wherein said recombinant bacterial host strain has been transformed with a second DNA molecule that encodes a protein.

25. The recombinant bacterial host strain of claim 24, wherein said second DNA molecule contains a sequence encoding a chymosin, a phytase, a xylanase, a lipase, an amylase, a protease, or a β-galactosidase.

* * * * *

SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
      (B) CLONE: AB3100

(xi) SEQUENCE DESCRIPTION: SEQ ID NO:1:

CTAATCTAGA ATGCCTCAAT CCTGAA                                          26

(2) INFORMATION FOR SEQ ID NO:2:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: YES (vii) IMMEDIATE SOURCE:
      (B) CLONE: AB3101

(xi) SEQUENCE DESCRIPTION: SEQ ID NO:2:

GACAGTCGAC AGCTATGGAG TCACCACA                                      28

(2) INFORMATION FOR SEQ ID NO:3:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
      (B) CLONE: TN0001

(xi) SEQUENCE DESCRIPTION: SEQ ID NO:3:

TCGATTAACT AGTTAA                                                            16

(2) INFORMATION FOR SEQ ID NO:4:

(i) SEQUENCE CHARACTERISTICS:
      (A) LENGTH: 35 base pairs
      (B) TYPE: nucleic acid

```
        (C) STRANDEDNESS: single
        (D) TOPOLOGY: linear (ii) MOLECULE TYPE: DNA (genomic)

(iii) HYPOTHETICAL: NO (vii) IMMEDIATE SOURCE:
        (B) CLONE: AB2154

(xi) SEQUENCE DESCRIPTION: SEQ ID NO:4:

AACCATAGGG TCGACTAGAC AATCAATCCA TTTCG                              35

(2) INFORMATION FOR SEQ ID NO:5:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vii) IMMEDIATE SOURCE:
        (B) CLONE: AB2155

(xi) SEQUENCE DESCRIPTION: SEQ ID NO:5:

GCTATTCGAA AGCTTATTCA TCCGGAGATC CTGAT                              35

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: AB2977

(xi) SEQUENCE DESCRIPTION: SEQ ID NO:6:

TATCAGGAAT TCGAGCTCTG TACAGTGACC                                    30

(2) INFORMATION FOR SEQ ID NO:7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vii) IMMEDIATE SOURCE:
        (B) CLONE: AB2992

(xi) SEQUENCE DESCRIPTION: SEQ ID NO:7:

GCTTGAGCAG ACATCACCAT GCCTCAATCC TGGGAA                             36
```

(2) INFORMATION FOR SEQ ID NO:8:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: AB2993

(xi) SEQUENCE DESCRIPTION: SEQ ID NO:8:

TTCCCAGGAT TGAGGCATGG TGATGTCTGC TCAAGC                      36

(2) INFORMATION FOR SEQ ID NO:9:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vii) IMMEDIATE SOURCE:
        (B) CLONE: AB2994

(xi) SEQUENCE DESCRIPTION: SEQ ID NO:9:

CTGATAGAAT TCAGATCTGC AGCGGAGGCC TCTGTG                      36

(2) INFORMATION FOR SEQ ID NO:10:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: AB3657

(xi) SEQUENCE DESCRIPTION: SEQ ID NO:10:

AGCTTGACGT CTACGTATTA ATGCGGCCGC T                             31

(2) INFORMATION FOR SEQ ID NO:11:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO

```
        (iv) ANTI-SENSE: YES (vii) IMMEDIATE SOURCE:
             (B) CLONE: AB3658

(xi) SEQUENCE DESCRIPTION: SEQ ID NO:11:

TCGAAGCGGC CGCATTAATA CGTAGACGTC A                                    31

(2) INFORMATION FOR SEQ ID NO:12:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
             (B) CLONE: AB3779

(xi) SEQUENCE DESCRIPTION: SEQ ID NO:12:

AATTGGGGCC CATTAACTCG AGC                                             23

(2) INFORMATION FOR SEQ ID NO:13:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: YES (vii) IMMEDIATE SOURCE:
             (B) CLONE: AB3780

(xi) SEQUENCE DESCRIPTION: SEQ ID NO:13:

AATTGCTCGA GTTAATGGGC CC                                              22

(2) INFORMATION FOR SEQ ID NO:14:

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
             (B) CLONE: AB3448

(xi) SEQUENCE DESCRIPTION: SEQ ID NO:14:

GTGCGAGGTA CCACAATCAA TCCATTTCGC                                      30

(2) INFORMATION FOR SEQ ID NO:15:
```

```
       (i) SEQUENCE CHARACTERISTICS:
           (A) LENGTH: 36 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: YES (vii) IMMEDIATE SOURCE:
           (B) CLONE: AB3449

(xi) SEQUENCE DESCRIPTION: SEQ ID NO:15:

ATGGTTCAAG AACTCGGTAG CCTTTTCCTT GATTCT                                36

(2) INFORMATION FOR SEQ ID NO:16:

(i) SEQUENCE CHARACTERISTICS:
           (A) LENGTH: 36 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
           (B) CLONE: AB3450

(xi) SEQUENCE DESCRIPTION: SEQ ID NO:16:

AGAATCAAGG AAAAGGCTAC CGAGTTCTTG AACCAT                                36

(2) INFORMATION FOR SEQ ID NO:17:

(i) SEQUENCE CHARACTERISTICS:
           (A) LENGTH: 42 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: YES (vii) IMMEDIATE SOURCE:
           (B) CLONE: AB3520

(xi) SEQUENCE DESCRIPTION: SEQ ID NO:17:

ATCAATCAGA AGCTTTCTCT CGAGACGGGC ATCGGAGTCC CG                         42

(2) INFORMATION FOR SEQ ID NO:18:

(i) SEQUENCE CHARACTERISTICS:
           (A) LENGTH: 18 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
```

(B) CLONE: AB3781

(xi) SEQUENCE DESCRIPTION: SEQ ID NO:18:

AATTGGGGCC CAGCGTCC                                                    18

(2) INFORMATION FOR SEQ ID NO:19:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vii) IMMEDIATE SOURCE:
        (B) CLONE: AB3782

(xi) SEQUENCE DESCRIPTION: SEQ ID NO:19:

AATTGGACGC TGGGCCCC                                                    18

(2) INFORMATION FOR SEQ ID NO:20:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: AB3746

(xi) SEQUENCE DESCRIPTION: SEQ ID NO:20:

TGACCAATAA AGCTTCTCGA GTAGCAAGAA GACCCAGTCA ATC                         43

(2) INFORMATION FOR SEQ ID NO:21:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vii) IMMEDIATE SOURCE:
        (B) CLONE: AB3747

(xi) SEQUENCE DESCRIPTION: SEQ ID NO:21:

CTACAAACGG CCACGCTGGA GATCCGCCGG CGTTCGAAAT AACCAGT                    47

(2) INFORMATION FOR SEQ ID NO:22:

(i) SEQUENCE CHARACTERISTICS:
        (A) LENGTH: 26 base pairs
        (B) TYPE: nucleic acid
        (C) STRANDEDNESS: single (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: AB4234

(xi) SEQUENCE DESCRIPTION: SEQ ID NO:22:

GAAGACCCAG TCAAGCTTGC ATGAGC                                              26

(2) INFORMATION FOR SEQ ID NO:23:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vii) IMMEDIATE SOURCE:
        (B) CLONE: AB4235

(xi) SEQUENCE DESCRIPTION: SEQ ID NO:23:

TGACCAATTA AGCTTGCGGC CGCTCGAGGT CGCACCGGCA AAC                           43

(2) INFORMATION FOR SEQ ID NO:24:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: AB4236

(xi) SEQUENCE DESCRIPTION: SEQ ID NO:24:

TGACCAATAA AGCTTAGATC TGGGGGTGAT TGGGCGGAGT GTTTTGCTTA GACAATCAAT         60

CCATTTCGC                                                                69

(2) INFORMATION FOR SEQ ID NO:25:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vii) IMMEDIATE SOURCE:
        (B) CLONE: AB4233

(xi) SEQUENCE DESCRIPTION: SEQ ID NO:25:

TGACCAATAG ATCTAAGCTT GACTGGGTCT TCTTGC                                    36

(2) INFORMATION FOR SEQ ID NO:26:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
         (B) CLONE: AB3514

(xi) SEQUENCE DESCRIPTION: SEQ ID NO:26:

CTGCGAATTC GTCGACATGC CTCAATCCTG GG                                        32

(2) INFORMATION FOR SEQ ID NO:27:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vii) IMMEDIATE SOURCE:
         (B) CLONE: AB3515

(xi) SEQUENCE DESCRIPTION: SEQ ID NO:27:

GGCAGTCTAG AGTCGACCTA TGGAGTCACC ACATTTC                                   37

(2) INFORMATION FOR SEQ ID NO:28:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
         (B) CLONE: AB3701

(xi) SEQUENCE DESCRIPTION: SEQ ID NO:28:

CTGCGAATTC GTCGACACTA GTGGTACCAT TATAGCCATA GGACAGCAAG                     50

(2) INFORMATION FOR SEQ ID NO:29:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vii) IMMEDIATE SOURCE:
              (B) CLONE: AB3700

(xi) SEQUENCE DESCRIPTION: SEQ ID NO:29:

GCTCTAGAGC GCGCTTATCA GCTTCCAGTT CTTCCCAGGA TTGAGGCATT TTTAATGTTA      60

CTTCTCTTGC      70

(2) INFORMATION FOR SEQ ID NO:30:

(i) SEQUENCE CHARACTERISTICS:
              (A) LENGTH: 50 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
              (B) CLONE: AB3702

(xi) SEQUENCE DESCRIPTION: SEQ ID NO:30:

CTGCGAATTC GTCGACACTA GTGGTACCAT CCTTTTGTTG TTTCCGGGTG      50

(2) INFORMATION FOR SEQ ID NO:31:

(i) SEQUENCE CHARACTERISTICS:
              (A) LENGTH: 70 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: YES (vii) IMMEDIATE SOURCE:
              (B) CLONE: AB3704

(xi) SEQUENCE DESCRIPTION: SEQ ID NO:31:

GCTCTAGAGC GCGCTTATCA GCGGCCAGTT CTTCCCAGGA TTGAGGCATT GTATATGAGA      60

TAGTTGATTG      70

(2) INFORMATION FOR SEQ ID NO:32:

(i) SEQUENCE CHARACTERISTICS:
              (A) LENGTH: 55 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
              (B) CLONE: AB3704

(xi) SEQUENCE DESCRIPTION: SEQ ID NO:32:

GCTCTAGAAG TCGACACTAG TCTGCTACGT ACTCCAGAAT TTATACTTAG ATAAG    55

(2) INFORMATION FOR SEQ ID NO:33:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vii) IMMEDIATE SOURCE:
        (B) CLONE: AB3705

(xi) SEQUENCE DESCRIPTION: SEQ ID NO:33:

TGCTCTAGAT CTCAAGCCAC AATTC    25

(2) INFORMATION FOR SEQ ID NO:34:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: AB3965

(xi) SEQUENCE DESCRIPTION: SEQ ID NO:34:

CTGCTACGTA ATGTTTTCAT TGCTGTTTTA C    31

(2) INFORMATION FOR SEQ ID NO:35:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vii) IMMEDIATE SOURCE:
        (B) CLONE: AB3966

(xi) SEQUENCE DESCRIPTION: SEQ ID NO:35:

CCGCCCAGTC TCGAGTCAGA TGGCTTTGGC CAGCCCC    37

(2) INFORMATION FOR SEQ ID NO:36:

(i) SEQUENCE CHARACTERISTICS:
        (A) LENGTH: 44 base pairs
        (B) TYPE: nucleic acid
        (C) STRANDEDNESS: single
        (D) TOPOLOGY: linear -continued

```
    (ii) MOLECULE TYPE: DNA (genomic)

(iii) HYPOTHETICAL: NO (iv) ANTI-SENSE: NO (vii) IMMEDIATE SOURCE:
         (B) CLONE: AB3825

(xi) SEQUENCE DESCRIPTION: SEQ ID NO:36:

CGCGCTTATC AGCGGCCAGT TCTTCCCAGG ATTGAGGCAT ATGT                    44

(2) INFORMATION FOR SEQ ID NO:37:

(i) SEQUENCE CHARACTERISTICS:
         (A) LENGTH: 44 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: YES (vii) IMMEDIATE SOURCE:
         (B) CLONE: AB3826

(xi) SEQUENCE DESCRIPTION: SEQ ID NO:37:

CTAGACATAT GCCTCAATCC TGGGAAGAAC TGGCCGCTGA TAAG                    44
```